US008039208B2

(12) United States Patent
Dwek et al.

(10) Patent No.: US 8,039,208 B2
(45) Date of Patent: *Oct. 18, 2011

(54) AUTOMATED STRATEGY FOR IDENTIFYING PHYSIOLOGICAL GLYCOSYLATION MARKERS(S)

(75) Inventors: Raymond A. Dwek, Oxford (GB); Louise Royle, Oxon (GB); Nicole Zitzmann, Oxford (GB); Catherine M. Radcliffe, Reading (GB); Pauline Rudd, Abingdon (GB)

(73) Assignee: National Institute for Bioprocessing Research and Training Limited (NIBRT), Dublin (IE)

( * ) Notice: Subject to any disclaimer, the term of this patent is extended or adjusted under 35 U.S.C. 154(b) by 1143 days.

This patent is subject to a terminal disclaimer.

(21) Appl. No.: 11/411,232

(22) Filed: Apr. 26, 2006

(65) Prior Publication Data

US 2006/0270048 A1   Nov. 30, 2006

Related U.S. Application Data

(60) Provisional application No. 60/674,723, filed on Apr. 26, 2005, provisional application No. 60/674,724, filed on Apr. 26, 2005.

(30) Foreign Application Priority Data

Jun. 24, 2005  (WO) .................. PCT/IB2005/002531
Jun. 24, 2005  (WO) .................. PCT/IB2005/002995

(51) Int. Cl.
   *C12Q 1/00*   (2006.01)
(52) U.S. Cl. .......................................................... 435/4
(58) Field of Classification Search .................. None
   See application file for complete search history.

(56) References Cited

U.S. PATENT DOCUMENTS

| | | | |
|---|---|---|---|
| 4,659,659 | A | 4/1987 | Dwek et al. |
| 7,700,745 | B2 | 4/2010 | Kakehi |
| 2004/0147033 | A1 | 7/2004 | Shriver et al. |
| 2004/0253651 | A1 | 12/2004 | Saarinen et al. |
| 2006/0269974 | A1 | 11/2006 | Dwek et al. |
| 2006/0269979 | A1 | 11/2006 | Dwek et al. |

FOREIGN PATENT DOCUMENTS

| | | |
|---|---|---|
| EP | 1 635 174 A1 | 3/2006 |
| WO | WO 02/08760 A1 | 1/2002 |
| WO | WO 03/016464 A2 | 2/2003 |
| WO | WO 2004/019040 A1 * | 3/2004 |
| WO | WO 2004/063753 A2 | 7/2004 |
| WO | WO 2004/066808 A2 * | 8/2004 |
| WO | WO 2004/077048 A1 | 9/2004 |

OTHER PUBLICATIONS

Kannicht et al (Glycobiology, 1999, 9(9): 897-906).*

Amano, J. et. al., "Quantitative Conversion of Mucin-Type Sugar chains to Radioactive Oligosaccharides," Methods Enzymol 179: 261-70, 1989.
Amess et al., "Programmed cell death in sympathetic neurons: a study by two-dimensional polyacrylamide gel electrophoresis using computer image analysis," Electrophoresis 16: 1255-1267, 1995.
Anumula et al., "Characterization of carbohydrates using highly fluorescent 2-aminobenzoic acid tag following gel electrophoresis of glycoproteins." Analytical Biochemistry, 275: 236-42, (1999).
Anumula, K. R., "Thematic Review: High-sensitivity and high-resolution methods for glycoprotein analysis," Analytical Biochemistry, 2000, 283: 17-26.
Axford, John S., "Glycosylation and rheumatic disease," Biochimica et Biophysica Acta, Oct. 8, 1999, vol. 1455, No. 2-3, pp. 219-229.
Bigge, J. C., et. al. "Nonselective and efficient fluorescent labeling of glycans using 2-amino benzamide and anthranilic acid," Analytical Biochemistry, 230: 229-38, 1995.
Blass, S., "Novel 68 kDa autoantigen detected by rheumatoid arthritis specific antibodies," Annals of the Rheumatic Diseases, 54:355-360, 1995.
Block et al., "Use of targeted glycoproteomics to identify serum glycoproteins that correlate with liver cancer in woodchucks and humans." Proc Natl Acad Sci U S A, 2005, 102: 779-84.
Brawer MK, "Prostate-specific antigen: current status," CA Cancer J Clin, 49, 264-281, 1999.
Burlingame, A. L., "Characterization of protein glycosylation by mass spectrometry." Curr Opin Biotechnol 7: 4-10, (1996).
Butler, M., et al. "Detailed glycan analysis of serum glycoproteins of patients with congenital disorders of glycosylation indicates the specific defective glycan processing step and provides an insight into pathogenesis." Glycobiology 13: 601-22, 2003.
Caesar et al., "Femtomole oligosaccharide detection using a reducing-end derivative and chemical ionization mass spectrometry," Analytical Biochemistry, 191: 247-52 (1990).
Callewaert et al., "Total serum protein N-glycome profiling on a capillary electrophoresis-microfluidics platform," Electrophoresis, 2004, 25: 3128-31.

(Continued)

*Primary Examiner* — Sean Aeder
(74) *Attorney, Agent, or Firm* — Foley & Lardner LLP

(57) ABSTRACT

One can identify and quantify one or more glycosylation markers of a physiological condition such as a disease or a stage of disease by utilizing quantitative HPLC analysis of glycans which have been released from unpurified glycoproteins. The unpurified glycoproteins can be total glycoproteins or a selection of the total glycoproteins. The identified glycosylation marker can be a native glycan or a digestion product which has been segregated and amplified by exoglycosidase digestions. This strategy is compatible with a high throughput format and glycan data base searching. One can utilize the identified glycosylation marker, for example, for monitoring the physiological condition in a subject. One can also use the glycosylation marker to identify glycoproteins that carry the glycosylation marker which can also be used to monitor the physiological condition. The biomarker may also be a subset of glycoforms of a glycoprotein that are separated in trains of spots on 2D gel.

28 Claims, 25 Drawing Sheets

OTHER PUBLICATIONS

Callewaert et al., "Increased fucosylation and reduced branching of serum glycoprotein N-glycans in all known subtypes of congenital disorder of glycosylation I." Glycobiology, 2003, 13: 367-375.

Chan et al., "Alpha-fetoprotein variants in a case of pancreatoblastoma," Ann Clin Biochem 37 ( Pt 5): 681-5, 2000.

Ciolczyk-Wierzbicka et al., "The structure of the oligosaccharides of N-cadherin from human melanoma cell lines," Glycoconjugate Journal, 2004, vol. 20, No. 7-8, pp. 483-492.

Costello, C. E., "Bioanalytic applications of mass spectrometry." Curr Opin Biotechnol 10: 22-8, 1999.

Davies et al., "Comparison of separation modes of high-performance liquid chromatography for the analysis of glycoprotein- and proteoglycan-derived oligosaccharides." J Chromatogr A 720: 227-33, 1996.

Despres et. al., "The Sa system: a novel antigen-antibody system specific for rheumatoid arthritis," J Rheumatol 21:1027-33, 1994.

Diamandis E., "Prostate-Specific antigen: Its Usefulness in Clinical Medicine," TEM, 9:310-316, 1998.

Diamandis, *Clin. Lab. News* 1996, 22: 235-239.

Duffy, M.J., "CA15.3 and related mucins as circulating markers in breast cancer," Ann. Clin. Biochem., 36, 579-586, 1999.

Edwards et. al., "Efficacy of B-cell-targeted therapy with rituximab in patients with rheumatoid arthritis," N Engl J Med, 350:2572, 2004.

El Rassi, Z., "Recent developments in capillary electrophoresis and capillary electrochromatography of carbohydrate species." Electrophoresis 20: 3134-44, 1999.

Ey et. al. "Isolation of pure $IgG_1$, $IgG_{2a}$ and $IgG_{2b}$ Immunoglobulins from mouse serum using protein A-Sepharose," *Molecular Immunology*, vol. 15, pp. 429, 1978.

Görg et al., "Current two-dimensional electrophoresis technology for proteomics," Proteomics, 4, 3665-3685, 2004.

Görg et al., "Horizontal SDS-PAGE for IGP-Dalt," Methods Mol. Biol, 112, 235-244, 1999.

Guile et al., "Analytical and preparative separation of anionic oligosaccharides by weak anion-exchange high-performance liquid chromatography on an inert polymer column." Analytical Biochemistry, 1994, 222: 231-5.

Guile et al., "Identification of highly fucosylated N-linked oligosaccharides from the human parotid gland," European Journal of Biochemistry, 1998, 258: 623-656.

Guile et. al., "A rapid high-resolution high-performance liquid chromatographic method for separating glycan mixtures and analyzing oligosaccharide profiles," Anal. Biochem. 240: 210-26, 1996.

Hardy et al., "High-pH anion-exchange chromatography of glycoprotein-derived carbohydrates," Methods Enzymol, 230: 208-25, 1994.

Harvey et al., "Proteomic analysis of glycosylation: structural determination of N- and O-linked glycans by mass spectrometry," Expert Review of Proteomics 2005, Apr. 1, 2005, vol. 2, No. 1, pp. 87-101.

Harvey, D. J., "Matrix-assisted laser desorption/ionization mass spectrometry of carbohydrates," Mass Spectrom Rev, 1999, 18: 349-450.

Harvey, D. J., "Electrospray mass spectrometry and fragmentation of N-linked carbohydrates derivatized at the reducing terminus," J Am Soc Mass Spectrom, 2000, 11: 900-915.

Harvey, DJ, "Fragmentation of negative ions from carbohydrates: Part 1; Use of nitrate and other anionic adducts for the production of negative ion electrospray spectra from N-linked carbohydrates," J. Am. Soc. Mass Spectrom., 2005, 16, 622-630.

Harvey, DJ, "Fragmentation of negative ions from carbohydrates: Part 2, Fragmentation of high-mannose N-linked glycans," J. Am. Soc. Mass Spectrom., 2005, 16, 631-646.

Harvey, DJ, "Fragmentation of negative ions from carbohydrates: Part 3, Fragmentation of hybrid and complex N-linked glycans," J. Am. Soc. Mass Spectrom., 2005, 16, 647-659.

Hassfeld et al., "Demonstration of a new antinuclear antibody (anti-RA33) that is highly specific for rheumatoid arthritis," Arthritis Rheum, 32:1515-1520, 1989.

Huang et al., "Microscale nonreductive release of O-linked glycans for subsequent analysis through MALDI mass spectrometry and capillary electrophoresis." Analytical Chemistry, 2001, 73: 6063-6069.

Jackson et al., "The use of polyacrylamide gel electrophoresis for the analysis of acidic glycans labeled with the fluorophore 2-aminoacridone," Electrophoresis, 15: 896-902, 1994.

Johnson et al., "Structures of disease-specific serum alpha-fetoprotein isoforms," *Br J Cancer* 83(10):1330-7, 2000.

Kassahn et. al., "Few human autoimmune sera detect GPI," Nat Immunol 3:411-412, 2002.

Keesee et. al., "Utilization of Nuclear Matrix Proteins for Cancer Diagnosis," Crit. Rev. Eukaryotic Gene Expr, 1996, 6(2&3): 189-214.

Klee et al., "MUC1 gene-derived glycoprotein assays for monitoring breast cancer (CA 15-3), CA 27.29, BR): Are They Measuring the Same Antigen?", Arch. Pathol. Lab. Med., 128, 1131-1135, 2004.

Kozak et. al., "Identification of biomarkers for ovarian cancer using strong anion-exchange ProteinChips: Potential use in diagnosis and prognosis," PNAS, 100:12343-12348, 2003.

Kuster et al., "Sequencing of N-linked oligosaccharides directly from protein gels: in-gel deglycosylation followed by matrix-assisted laser desorption/ionization mass spectrometry and normal-phase high-performance liquid chromatography." Anal-Biochem, 1997, 250: 82-101.

Laemmli, UK, "Cleavage of structural proteins during the assembly of the head of bacteriophage T4," Nature, 227, 680-685, 1970.

Lillemoe et al., "Pancreatic cancer: state-of-the art care," Cancer J. Clin., 50, 241-268, 2000.

Mattu et al., "O-glycan analysis of natural human neutrophil gelatinase B using a combination of normal phase-HPLC and online tandem mass spectrometry: implications for the domain organization of the enzyme," Biochemistry 39: 15695-704, 2000.

Mattu et al., "The glycosylation and structure of human serum IgA1, Fab, and Fc regions and the role of N-glycosylation on Fc alpha receptor interactions," Journal of Biological Chemistry 273: 2260-72, 1998.

Mazor et al., "Humanization and epitope mapping of the H23 anti-MUC1 monoclonal antibody reveals a dual epitope specificity," Mol Immunol., Jan. 2005, 42(1):55-69.

Mor et al., "Serum protein markers for early detection of ovarian cancer," PNAS, 102:7677-7682, 2005.

Nienhuis et al., "A new serum factor in patients with rheumatoid arthritis. The antiperinuclear factor," Annals of Rheumatic Disease, 23:302, 1964.

Papac et. al., "A high-throughput microscale method to release N-linked oligosaccharides from glycoproteins for matrix-assisted laser desorption/ionization time-of-flight mass spectrometric analysis," Glycobiology, 8: 445-54, 1998.

Parekh et al., "A comparative analysis of disease-associated changes in the galactosylation of serum IgG," J. Autoimmunity, 2:101-114, 1989.

Parekh et al., "Galactosylation of IgG associated oligosaccharides: Reduction in patients with adult and juvenile onset rheumatoid arthritis and relation to disease activity," Lancet, pp. 966-969, Apr. 1988.

Parekh et al., "N-Glycosylation and in vitro Enzymatic Activity of Human Recombinant Tissue Plasminogen Activator Expressed in Chinese Hamster Ovary Cells and a Murine Cell line" Biochemistry, 1989, 28, 7670-7679.

Parekh et al., $3_{rd}$ Jenner International Immunoglycobiology Meeting Abstract, *Glycoconjugate Journal* (1994) 1, 3 195-227.

Parekh et. al. "Association of Rheumatoid Arthritis and Primary Osteoarthritis with Changes in the Glycosylation Pattern of Total Serum IgG," Nature, 316, pp. 452-457, 1985.

Peracaula et al., "Altered glycosylation pattern allowes the distinction between prostate-specific antigen (PSA) from normal and tumor origins." Glycobiology, 13: 457-70, 2003.

Peracaula et al., "Glycosylation of human pancreatic ribonuclease: differences between normal and tumor states," Glycobiology, Apr. 1, 2003, vol. 13, No. 4, pp. 227-244.

Perkins et al., "Serum tumor markers," American Family Physician, 68, 1075-1082, 2003.

Reinhold et al., "Carbohydrate sequence analysis by electrospray ionization-mass spectrometry," Methods Enzymol, 271: 377-402, 1996.

Rønningen et. al., "Rheumatoid arthritis may be primarily associated with HLA-DR4 molecules sharing a particular sequence at residues 67-74," Tissue Antigens 36:235-240, 1990.

Rooney et.al., "The immunohistologic features of synovitis, disease activity and in vitro IgM rheumatoid factor synthesis by blood mononuclear cells in rheumatoid arthritis," Journal of Rheumatology, 16:459-467, 1989.

Royle et. al., "An analytical and structural database provides a strategy for sequencing O-glycans from microgram quantities of glycoproteins," Anal. Biochem. 304: 70-90, 2002.

Sanchez et al., "Improved and simplified in-gel sample application using reswelling of dry immobilized pH gradients," Electrophoresis, 18: 324-327, 1997.

Schaller et. al., "Autoantibodies to GPI in rheumatoid arthritis: linkage between an animal model and human disease," Nat Immunol, 2:746-753, 2001.

Schubert et. Al, "Autoantibodies to GPI and creatine kinase in RA," Nat Immunol, 3:411; discussion 412, 2002.

Smith et. al., "Measurement of protein using bicinchoninic acid," Analytical Biochemistry, 150: 76-85, 1985.

Stein et. al., "Prognostic markers in bladder cancer: a contemporary review of the litearture," J. Urol, 1998, 160(3, pt 1):645-659.

Taylor-Papadimitriou et al., "MUC1 and cancer," Biochem. Biophys. Acta., 1455:301-313, 1999.

Townsend et al., "High-performance anion-exchange chromatography of oligosaccharides using pellicular resins and pulsed amperometric detection," Analytical Biochemistry, 174: 459-70, 1988.

van Boekel et. al., "Autoantibody systems in rheumatoid arthritis: specificity, sensitivity and diagnostic value," Arthritis Res, 4:87-93, 2002.

Van Boxel et al., "Predominantly T-cell infiltrate in rheumatoid synovial membranes," New England Journal of Medicine, 293:517-520, 1975.

Watkins et al., "Detection of early-stage cancer by serum protein analysis," American Laboratory. Jun. 2001, 32-36.

Watson et al., "Sugar Printing Rheumatic Diseases: A Potential Method for Disease Differentiation Using Immunoglobulin G Oligosaccharides," Arthritis and Rheumatism, 42(8):1682-1690, 1999.

Wittwer et al., "Effects of N-Glycosylation on in vitro Activity of Bowes Melanoma and Human Colon Fibroblast Derived Tissue Plasminogen Activator," Biochemistry, 1989, 28, 7662-7669.

Wordsworth et al., "HLA-DR4 subtype frequencies in rheumatoid arthritis indicate that DRB1 is the major susceptibility locus within the HLA class II region," Proceedings of the National Academy of Sciences of the United States of America, 86:10049-10053, 1989.

Yeo et al., "Epidemiology and Risk Factors," Current Problems in Cancer 26(4):176-275, 2002.

Young et. Al, "Anti-keratin antibodies in rheumatoid arthritis", Br Med J, 2:97-99, 1997.

Fukuda et al., "Structures of O-linked Oligosaccharides Isolated from Normal Granulocytes, Chronic Myelogenous Leukemia Cells, and Acute Myelogenous Leukemia Cells," J. Biol. Chem., Sep. 25, 1986, 261(27):12796-12806.

Kannicht et al., "N-Glycosylation of the carcinoembryonic antigen related cell adhesion molecule, C-CAM, from rat liver: detection of oversialylated bi- and triantennary structures," Glycobiology, 1999, 9(9):897-906.

Tockman et al., "Considerations in Bringing a Cancer Biomarker to Clinical Application," Cancer Research (Suppl.), May 1, 1992, 52:2711s-2718s.

Office Action mailed Dec. 16, 2008 in U.S. Appl. No. 11/411,246 (US Publication 2006-0269974), 30 pages.

Office Action mailed Aug. 19, 2009 in U.S. Appl. No. 11/411,231 (US Publication 2006-0269979), 11 pages.

DeGroot et al., "Molecular markers for osteoarthritis: the road ahead," Current Opinion in rheumatology, 2002, 14:585-589.

Lebrilla et al., "The prospects of glycan biomarkers for the diagnosis of diseases," Molecular Biosystems, 2009, 5:17-20.

Scofield, R.H., "Autoantibodies as predictors of disease," The Lancet, 2004, 363:1544-1546.

Villalta et al., "The laboratory approach to the diagnosis of autoimmune diseases: Is it time to change?" Autoimmunity Reviews, 2007, 6:359-365.

Wollheim et al., "Markers of disease in rheumatoid arthritis," Current Opinion in Rheumatology, 2000, 12:200-204.

Non-final Office Action mailed Dec. 3, 2009 in U.S. Appl. No. 11/411,246 (US Publication No. 2006-0269974), 24 pages.

Final Office Action mailed Mar. 30, 2010, in U.S. Appl. No. 11/411,231.

Final Office Action mailed May 13, 2010, in U.S. Appl. No. 11/411,246.

Karlsson et al., "Analysis of O-Linked Reducing Oligosaccharides Released by an In-line Flow System," Analytical Biochemistry, 2002, 305:173-185.

* cited by examiner

Multi-dimensional glycan structural analysis and profiling

Figure 5.
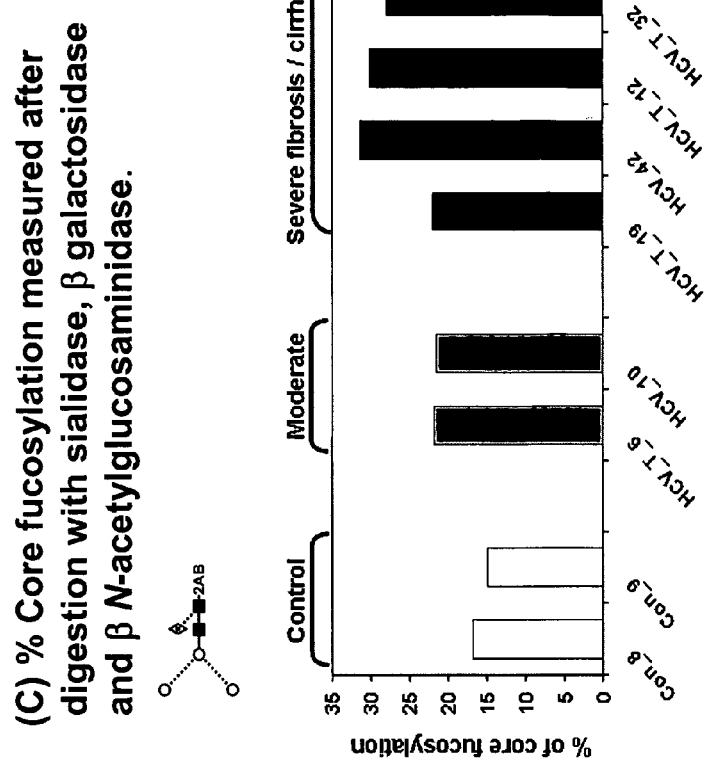
(C) % Core fucosylation measured after digestion with sialidase, β galactosidase and β N-acetylglucosaminidase.
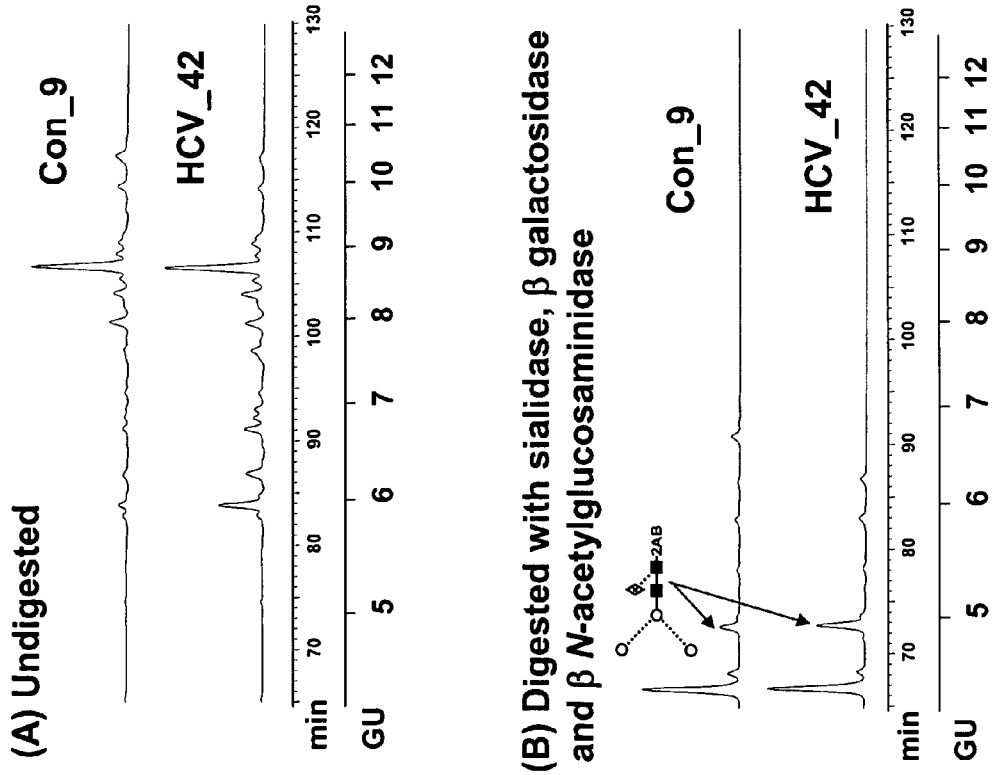
(A) Undigested
(B) Digested with sialidase, β galactosidase and β N-acetylglucosaminidase

Figure 10c.

| | GLYCOBASE A glycan information resource from the P. M. Rudd group, Oxford Glycobiology Institute, Director Raymond A. Dwek | | | |
|---|---|---|---|---|
| Glycan List | Nomenclature | | Enzymes | Personnel |

| Glycan Listing & Export | | |
|---|---|---|
| Export Selected | Printer-Friendly Format | Admin Menu |

Use the control palette, below right, to manipulate the glycan list, below left. Click the "Refresh List" button to enact any changes you have made to the controls. You may download your selected glycans or group them using the "Export Selected" button above. # Paper number refer to Glycobiology Institute Publications List. Currently listing 297 glycan records.

| Image | Glycan Structure *(Click for info!)* | GU | Export? | List Columns |
|---|---|---|---|---|
| | | | | ☑ Schematic diagram |
| ←•• | GalNAc | 0.91 | ☑ | ☑ Structural abbreviation |
| •••• | Glucose | 1.00 | ☑ | ☑ Consensus GU value |
| •••• | BA | 1.01 | ☑ | ☑ Export checkbox |
| | | | | List Order |
| ••• | BB | 1.58 | ☑ | GU Value ▼ |
| ••• | 322 | 1.70 | ☑ | ☐ Reverse list order |
| •••• | GalNAc-A(6) | 1.79 | ☑ | Visible Glycoforms |
| ••• | Core I | 1.81 | ☑ | ☑ N-linked [+] |
| ••• | BC | 1.82 | ☑ | ☑ O-linked [+] |
| •••• | lactose | 2.00 | ☑ | ☑ GSL [+] |
| | | | | ☑ Misc [+] |
| •••• | Galbeta1-4GalNAc | 2.03 | ☑ | Glycan Groupings |
| •••• | Galbeta1-6GalNAc | 2.10 | ☑ | No Group Selected ▼ |

Figure 12. N-glycan profiles obtained from individual or pooled protein spots from control human serum.

Exoglycosidase digestion of whole serum glycans highlights differences in breast cancer glycosylation ated Apr. 26, 2005 and 60/674,723 to Dwek et. al. filed Apr. 26, 2005, which are both incorporated herein by reference in their entirety. The present application also claims priority to PCT applications Nos. PCT/IB2005/002995 to Dwek et. al. filed Jun. 24, 2005 and PCT/IB2005/002531 to Dwek et. al. filed Jun. 24, 2005, which are both incorporated herein by reference in their entirety.

AUTOMATED STRATEGY FOR IDENTIFYING PHYSIOLOGICAL GLYCOSYLATION MARKERS(S)

PRIORITY CLAIM

The present application claims priority to U.S. provisional patent applications No. 60/674,724 to Dwek et. al. filed Apr. 26, 2005 and 60/674,723 to Dwek et. al. filed Apr. 26, 2005, which are both incorporated herein by reference in their entirety. The present application also claims priority to PCT applications Nos. PCT/IB2005/002995 to Dwek et. al. filed Jun. 24, 2005 and PCT/IB2005/002531 to Dwek et. al. filed Jun. 24, 2005, which are both incorporated herein by reference in their entirety.

FIELD

This invention relates to methods of identifying markers of physiological conditions, and, in particular, of identifying markers of physiological conditions based on detailed glycosylation analysis.

BACKGROUND

Specific disease related glycosylation changes for glycans released from purified serum IgG were first reported for rheumatoid arthritis, see Parekh et. al. "Association of Rheumatoid Arthritis and Primary Osteoarthritis with Changes in the Glycosylation Pattern of Total Serum IgG," *Nature*, 316, pp. 452-457, 1985, incorporated herein by reference. Subsequent work demonstrated that these changes were not only diagnostic of rheumatoid arthritis (RA), but could also be used as prognostic indicators as well as monitors of RA disease activity, see e.g. "Galactosylation of IgG associated oligosaccharides: Reduction in patients with adult and juvenile onset rheumatoid arthritis and relation to disease activity," R. B. Parekh, D. A. Isenberg, B. M. Ansell, I. M. Roitt, R. A. Dwek and T. W. Rademacher (1988) Lancet, 1(8592), 966-969; "A comparative analysis of disease-associated changes in the galactosylation of serum IgG" R. B. Parekh, D. Isenberg, G. Rook, I. Roitt, R. A. Dwek and T. W. Rademacher (1989) J. Autoimmunity, 2, 101-114; 3$^{rd}$ Jenner International Immunoglycobiology Meeting Abstract R. B. Parekh, Isenberg, D., Dwek, R. A. and Rademacher, T. W. Glycoconjugate Journal (1994) 1, 3 195-227, all incorporated herein by reference in their entirety. Later, it was demonstrated that specific glycosylation changes in total serum glycosylation can be also bio-markers of other diseases. For example, Block et. al. determined specific glycosylation changes in total serum of hepatocellular carcinoma woodchucks infected with hepatitis B virus by performing a glycosylation analysis on glycans enzymatically released from a total serum solution, i.e. by a method not compatible with a high throughput format, see Block, T. M., Comunale, M. A., Lowman, M., Steel, L. F., Romano, P. R., Fimmel, C., Tennant, B. C., London, W. T., Evans, A. A., Blumberg, B. S., Dwek, R. A., Mattu, T. S. and Mehta, A. S. (2005). "Use of targeted glycoproteomics to identify serum glycoproteins that correlate with liver cancer in woodchucks and humans." *Proc Natl Acad Sci USA* 102: 779-84, incorporated herein by reference in its entirety. Glycosylation analysis of whole serum glycoproteins from patients and healthy controls using a combination of high-performance liquid chromatography (HPLC) (see Guile, G. R., et. al., "A rapid high-resolution high-performance liquid chromatographic method for separating glycan mixtures and analyzing oligosaccharide profiles." *Anal. Biochem.* 240: 210-26, 1996; Royle, L., et. al. "An analytical and structural database provides a strategy for sequencing O-glycans from microgram quantities of glycoproteins." *Anal. Biochem.* 304: 70-90, 2002) and Mass Spectrometry (MS) technology was first used to confirm the diagnosis of a patient with congenital disorders of glycosylation (CDGs) type II and to establish the faulty glycosylation processing step in an undiagnosed patient, see Butler, M., et. al. "Detailed glycan analysis of serum glycoproteins of patients with congenital disorders of glycosylation indicates the specific defective glycan processing step and provides an insight into pathogenesis." *Glycobiology* 13: 601-22, 2003. The glycan profile and analysis were flawed because hydrazinolysis was used to release the glycans. The use of hydrazinolysis results in the desialylation of a significant proportion of the sugars and the introduction of a number of artifacts such as loss of N-acetyl and N-glycolyl groups from the amino sugar residues (which are subsequently re-N-acetylated and this can result in both under and over acetylation), as well as loss of O-acetyl substitutions in sialic acids. Callewaert et al. used enzymatic release in whole serum glycosylation analysis by capillary electrophoresis on a microfluidic platform, see Callewaert, N., Contreras, R., Mitnik-Gankin, L., Carey, L., Matsudaira, P. and Ehrlich, D. (2004). "Total serum protein N-glycome profiling on a capillary electrophoresis-microfluidics platform." *Electrophoresis* 25: 3128-31 and Callewaert, N., Schollen, E., Vanhecke, A., Jaeken, J., Matthijs, G., and Contreras, R. (2003). "Increased fucosylation and reduced branching of serum glycoprotein N-glycans in all known subtypes of congenital disorder of glycosylation I." Glycobiology 13: 367-375. Although enzymatic release of Callewaert et. al. is compatible with a high throughput format, their analyses determined only major desialylated structures. Thus, a need still exists to develop a high throughput fully automated method for determining robust glycosylation markers of diseases based on a detailed glycosylation analysis of total glycoproteins in samples of body fluid or body tissue.

SUMMARY

According to one embodiment, one can identify and/or quantify one or more glycosylation markers of a physiological condition by a method, comprising (A) obtaining a biological sample of a subject affected by the physiological condition; (B) immobilizing total glycoproteins from the biological sample; (C) releasing glycans of the immobilized glycoproteins; (D) measuring a glycosylation profile of the glycans by quantitative high performance liquid chromatography, mass spectrometry or a combination thereof; and (E) comparing the glycosylation profile with a control profile to determine the one or more glycosylation markers. According to another embodiment, one can identify and/or quantify one or more biomarkers of a physiological condition by a method, comprising (A) obtaining a biological sample of a subject affected with the condition; (B) separating proteins of the biological sample into a plurality of spots using 2-dimensional electrophoresis, wherein each spot of the plurality corresponds to one or more glycoforms of the proteins; (C) releasing from one or more spots of said plurality; and (D) measuring a glycoprofile of the glycans using quantitative high performance liquid chromatography, mass spectrometry or a combination thereof for an altered level of one or more glycosylation markers of the physiological condition.

BRIEF DESCRIPTION OF THE DRAWINGS

FIG. 5 demonstrates the percentage of core fucosylated glycans in whole serum from HCV patients.

Figure 10D:
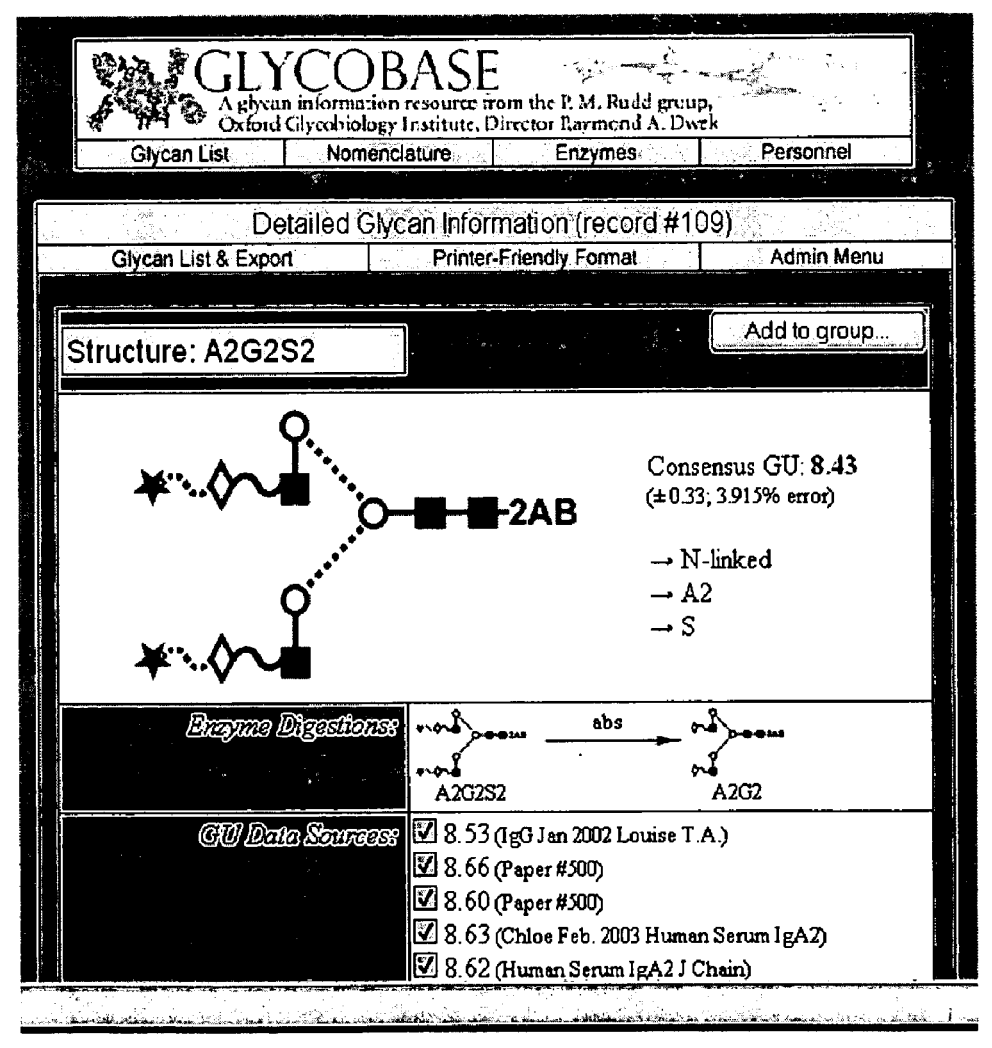
Figure 10E:
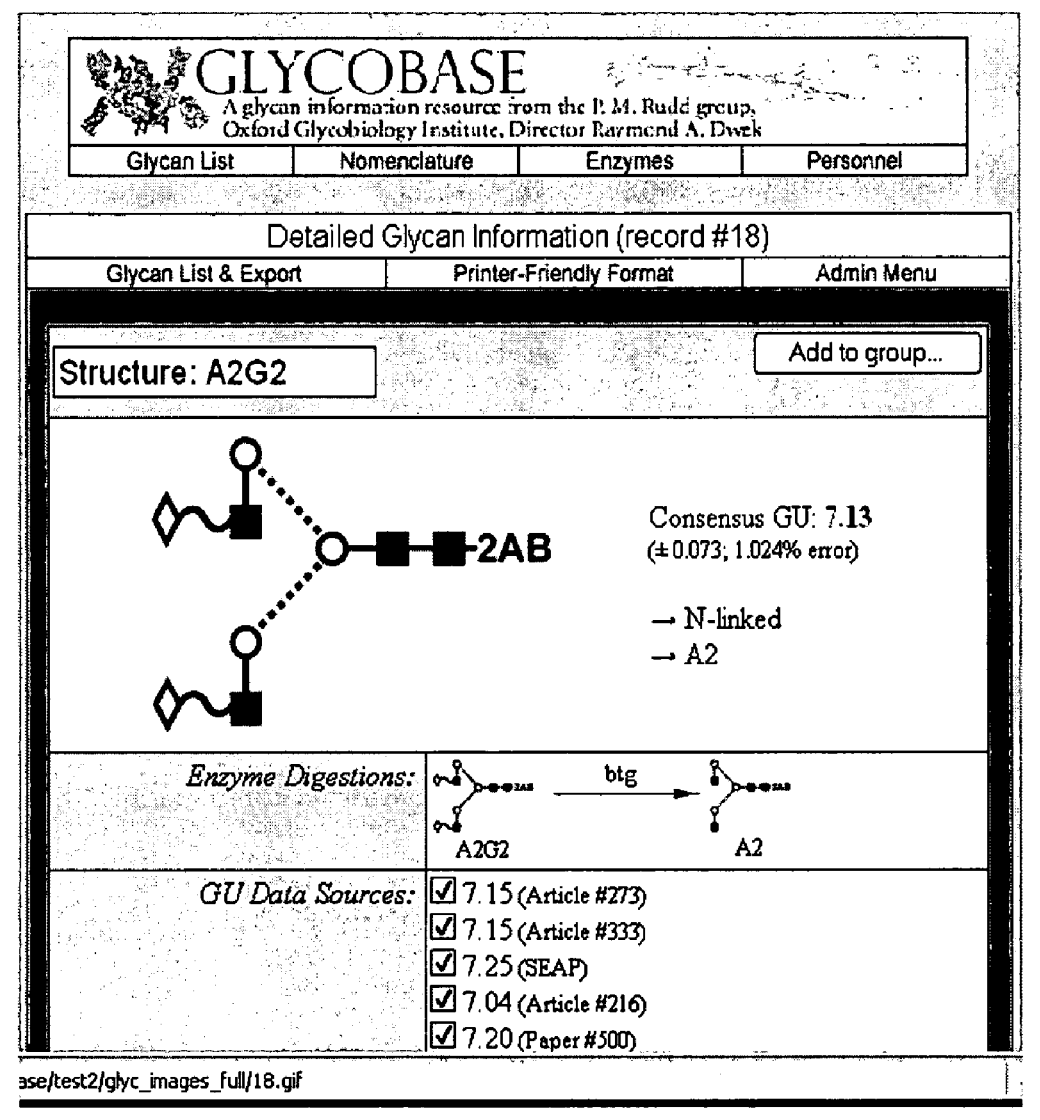

FIG. 10a-g illustrate a glycan database at Oxford Glycobiology Institute: (a) & (b) show the nomenclature used to draw the glycan structures and explain the exoglycosidase digestions; (c) shows some of the structures with GU values listed in the database; (d) to (g) follow the structure A2G2S2 (d) thorough a series of digestions, in each case the consensus GU value (which is calculated from the experimentally determined GU values listed) is given along with possible digestions and products.

DETAILED DESCRIPTION

This invention relates to methods of identifying markers of physiological conditions, and, in particular, to methods of identifying markers of physiological conditions based on detailed glycan analysis.

Unless otherwise specified, "a" or "an" means "one or more."

"Glycoprotein" designates an amino acid sequence and one or more oligosaccharide (glycan) structures associated with the amino acid sequence.

Glycoprotein can have one or more glycoforms. Each of the glycoforms of the particular glycoprotein has the same amino acid sequence, however, glycan structures associated with distinct glycoforms differ by at least one glycan.

"Glycoprofile" or "glycosylation profile" means a presentation of glycan structures (oligosaccharides) present in a pool of glycans. A glycoprofile can be presented, for example, as a plurality of peaks each corresponding to one or more glycan structures present in a pool of glycans.

"Glycosylation marker" means a particular difference in glycosylation in a biological sample affected by a physiological condition and a control sample.

"Biological sample" can be any sample that contains glycoproteins. The biological sample can be a sample from any species including animal, yeast, fungus, fish, insect, reptile, plant, bacteria, parasite, cell culture or product thereof. In some embodiments, the biological sample can be a sample of a body fluid or a body tissue of a mammal such as a human. The body fluid can be whole serum, blood plasma, urine, seminal fluid, seminal plasma, feces or saliva. A variety of techniques are available for obtaining a biological sample.

The methods of the present invention can be used for any physiological condition that can affect glycosylation of glycoproteins. For example, the physiological condition can be a disease or a stage of disease.

"Control profile" means a glycosylation profile of a biological sample not affected by the physiological condition.

The term "subject" means any subject from a biological sample containing glycoproteins can be obtained. For example, the subject can be an animal such as a mammal including a human. The subject can also be yeast, fungus, fish, insect, reptile, plant, bacteria, parasite or cell culture.

A high throughput format can mean a standard multiwell format such 48 well plate or 96 well plate.

The present application incorporates by reference US application "Glycosylation markers for cancer diagnosing and monitoring" to Dwek et. al. filed Apr. 26, 2006 and US application "High Throughput Glycan Analysis for Diagnosing and Monitoring Rheumatoid Arthritis and Other Autoimmune Diseases" to Dwek et. al. filed Apr. 26, 2006

Strategy

Figure 1:
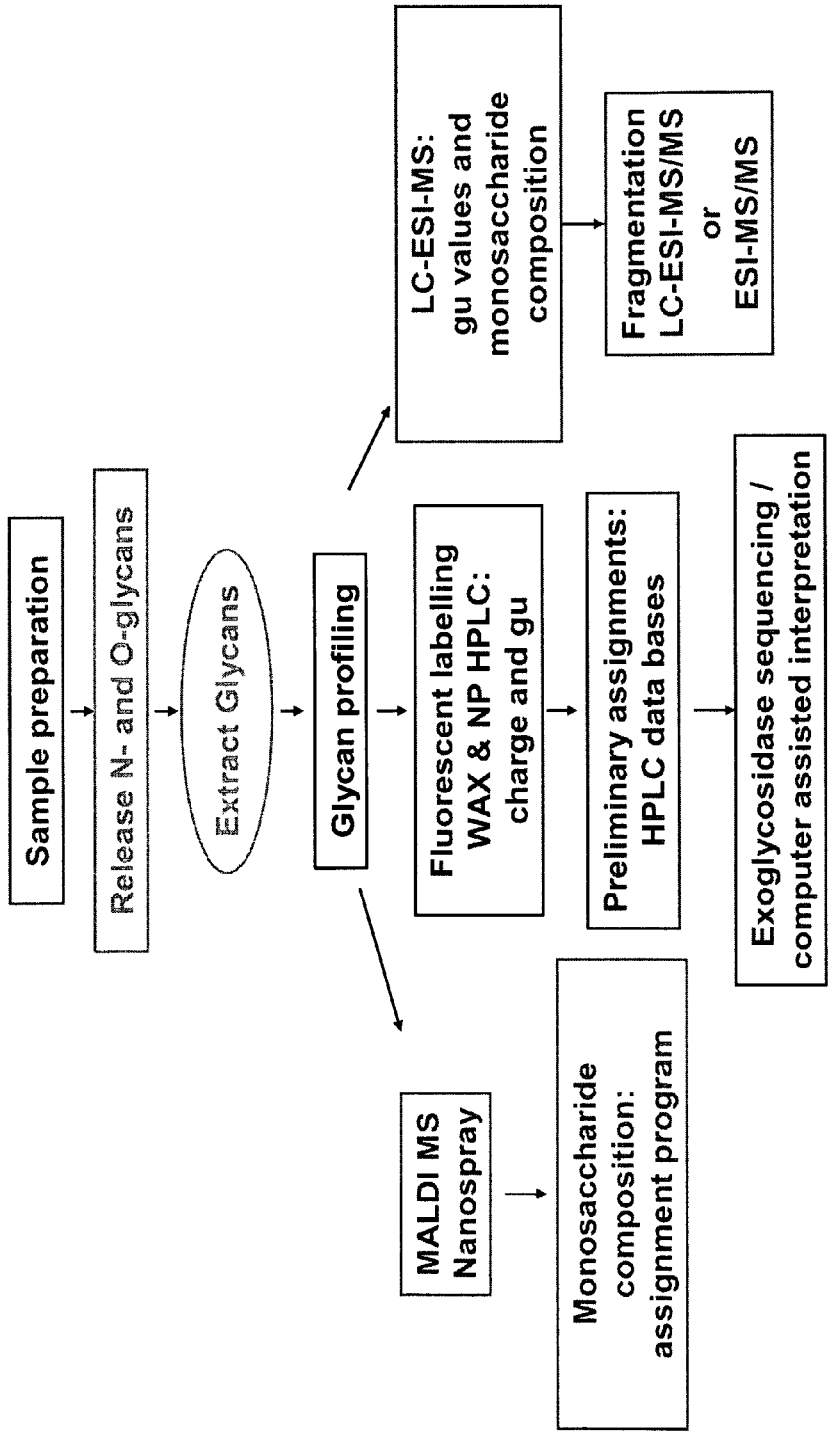
FIG. 1 illustrates a strategy for multidimensional glycan structural analysis.

The present invention is directed to development of a fully automated system based on a detailed glycosylation analysis. The general methodology of the detailed glycosylation analysis is illustrated on FIG. 1. In particular, a sample of a body fluid or body tissue can be obtained from a subject. A glycan pool (of N-linked glycans and/or O-linked glycans) of total glycoproteins, i.e. of all or substantially all glycoproteins, can be released from the sample. Releasing of the glycan pool can be carried out without exposing the sample to hydrazinolysis and without purifying specific glycoproteins. The detailed analysis of the glycan pool can be carried out by high performance liquid chromatography, mass spectrometry or a combination thereof. The released glycans can be fluorescently labeled prior to analysis. The detailed analysis can include separating the glycan pool into several aliquots based on the charge of glycans in each aliquot by weak anion exchange chromatography or a related technique. The NP-HPLC analysis can be performed on each aliquot. The NP-HPLC analysis performed on the total glycan pool or WAX aliquot of the glycan pool can result in a glycoprofile which can comprise a plurality of peaks. Each peak in the glycoprofile can be preliminary assigned to a particular glycan structure using a database of known glycan structures. The database can recommend particular exoglycosidase treatment to establish a final assignment of each peak in the glycoprofile.

Figure 2:
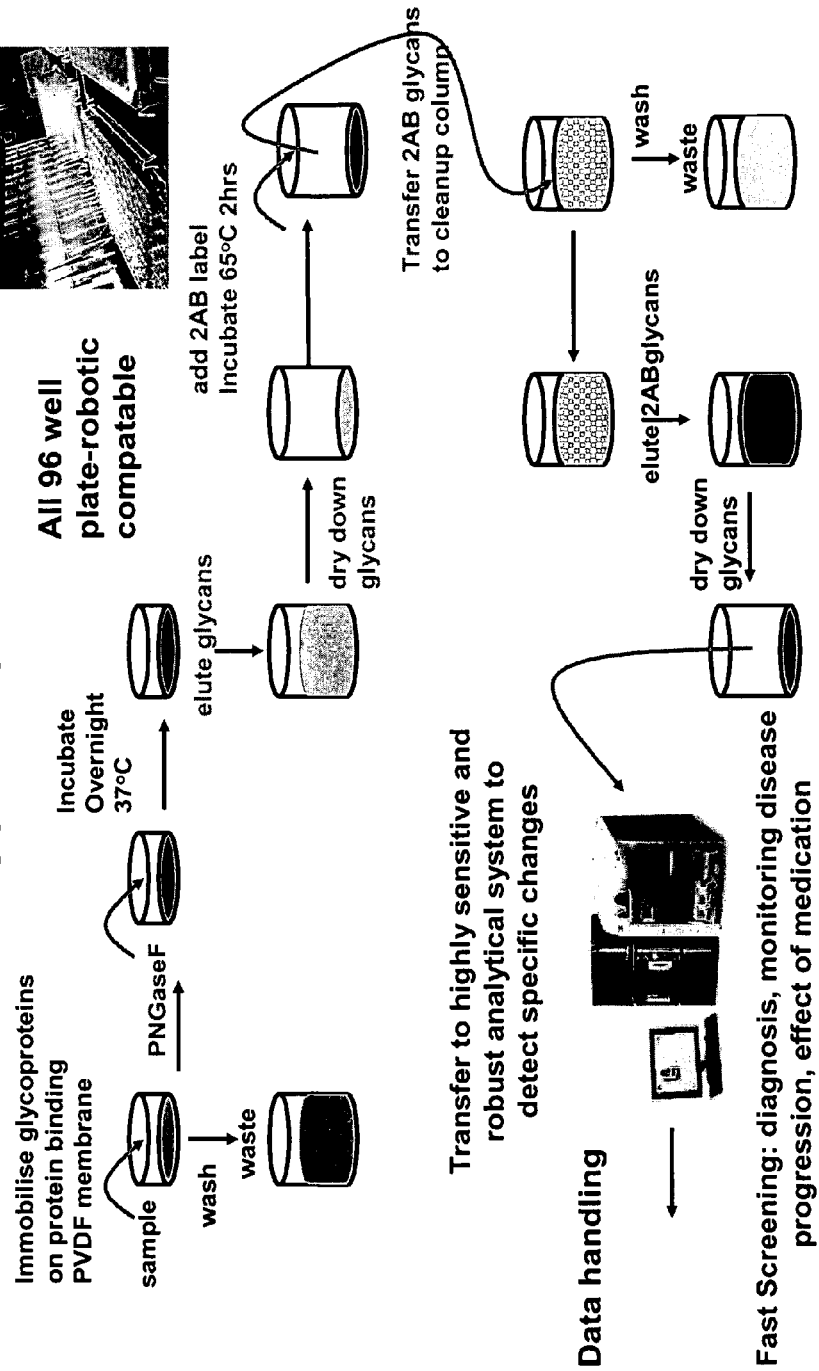
FIG. 2 illustrates for high throughput analysis of glycans from serum glycoproteins.

FIG. 2 illustrates one possible embodiment of a high throughput fully automated system based on the detailed quantitative glycan analysis. The fully automated high throughput system can, for example, use glycan release methods fully compatible with a high throughput format such as standard multiwell format and can include computer assisted data analysis suitable for clinical screening. Accordingly, the present invention provides methods of glycan releasing compatible with a high throughput format, databases and methods of using databases in automated glycan analysis. The present invention also provides methods of determining glycosylation markers of disease based on the detailed glycosylation analysis and related methods for using the glycosylation markers of disease for diagnosing and monitoring the disease.

Identification of One or More Glycosylation Markers

According to one embodiment, one can identify one or more glycosylation markers of the physiological condition in a provided biological sample by first immobilizing total glycoproteins from the sample. The total glycoproteins can be immobilizied in a non-selective format i.e. in a format that does not preferably immobilize a particular type of protein. The example of the non-selective format can be a gel block discussed infra. In some embodiments, the total glycoproteins can be immobilized in a high throughput format such as 96 well format. Upon immobilizing, glycans of the immobilized glycoproteins can be released. Preferably, glycans are released in such a way so that they are not modified, i.e. the released glycans are native glycans of the glycoproteins of the biological sample. The released glycans can then be subjected to a glycosylation analysis which includes measuring the glycosylation profile of the released glycans. The glycosylation profile is determined by quantitative high performance liquid chromatography (HPLC), mass spectrometry or their combination. Preferably, the glycosylation profile is measured by quantitative HPLC alone or in combination with mass spectrometry. The measured glycosylation profile can be then compared with a control profile to identify one or more glycosylation markers of the physiological condition. In some cases, comparing the measured glycosylation profile and the control profile can involve comparing peak ratios in the profiles. When more than one glycosylation marker is identified, one can select one or more of the markers that have the highest correlation with parameters of the physiological condition as the best marker. When the physiological condition is a disease and the sample is a sample from a human, illustrative examples of such parameters can be diagnosis, age, sex, disease stage, response to therapy and medical history.

In some embodiments, the released glycans can be subjected to a digestion with one or more exoglycosidases in order to amplify and/or segregate the one or more glycosylation markers which may or may not be a glycan digestion product. The digestion can be a sequential digestion. The digestion can be also a digestion with an array comprising one or more glycosidases. The details of exoglycosidase digestion are provided infra.

According to another embodiment, one can identify one or more glycosylation markers of a physiological condition in a biological sample by immobilizing unpurified glycoproteins from the biological sample and performing a detailed glycosylation analysis of glycans of the immobilized glycoproteins by quantitative HPLC alone or in combination with mass spectrometry. In some embodiments, the unpurified glycoproteins can be total glycoproteins in the biological sample immobilized in a non-selective format. Yet in some embodiments, the unpurified glycoproteins can be a selection of total glycoproteins in the biological sample. The selection of total glycoproteins is not limited to a single type of glycoprotein from the biological sample but still represents a pool or plurality of different types of glycoproteins. In some embodiments, a selection of total glycoproteins can be immobilized on a protein binding membrane such as PVDF membrane. Yet in some embodiments, a selection of total glycoproteins can be immobilized in a gel piece such as a gel band or a gel spot. Upon immobilizing the unpurified glycoproteins, one can release unmodified, i.e. native glycans of the glycoproteins and subject the glycans to glycosylation analysis by measuring a glycosylation profile of the glycans. The measured glycosylation profile can then be compared with a control profile to identify and/or quantify one or more glycosylation marker of the physiological condition which can be a native glycan or a product of digesting the glycans with one or more exoglycosidases.

According to yet another embodiment, one can identify and/or quantify one or more glycosylation markers of a physiological condition in a biological sample by releasing unmodified, i.e. native glycans of unpurified glycoproteins of the biological sample, measuring a detailed glycosylation profile; comparing the glycosylation profile with a control profile and digesting the glycans with one or more exoglycosidases to segregate and amplify the glycosylation marker. In this embodiment, measuring can be performed by quantitative HPLC, mass spectrometry or a combination thereof. Preferably, the measurement is carried out by quantitative HPLC alone or in combination with mass spectrometry. The glycosylation marker identified by this method may not be a native glycan but a digestion product, i.e. it comprises one or more digested glycans.

The identified glycosylation marker(s) can be used for diagnosing, monitoring and/or prognosticating a physiological condition such as a disease in a subject by either the experimental techniques used to identify the marker or by any other suitable technique such as capillary electrophoresis or lectin chromatography. The identified glycosylation marker can be also used for determining a clinical status of subject from a level of glycosylation marker. The glycosylation marker(s) can be also used for monitoring an effect of a therapy on a subject by comparing a level of the marker before and after a treatment of the subject with a therapy. One can use also use the glycosylation markers for adjusting and/or optimizing a dose of a therapeutic agent or for testing a new therapy or a new therapeutic agent for treating the physiological condition such as disease.

The identified glycosylation marker(s) can be also used for identification and/or isolation of one or more glycoprotein biomarkers of a physiological condition in a biological sample, i.e. for identification and/isolation of glycoprotein(s) that carry the glycosylation marker(s). In some embodiments, identification of such biomarkers utilizes 2 dimensional electrophoresis to separate proteins, including glycoproteins, in the biological sample into a plurality of spots. The spots of the plurality can be organized into individual spots or trains of spots. Each of the spots comprises one or more glycoforms of the proteins in the biological sample. Upon the separation, one can release glycans from one or more spots, i.e. unmodified glycans of the protein glycoforms of the one or more spots. Then, one can measure a glycosylation profile of the released glycoproteins searching for an altered level of the glycosylation marker(s). One then can select one or more glycoforms that correspond to the one or more spots, for which an altered level of the glycosylation marker(s) is found, as a biomarker of the physiological condition. The measuring of the glycosylation profile can be carried out by quantitative HPLC alone or in combination with mass spectrometry. In some embodiments, the one or more tested spots can correspond to glycoforms of highly abundant glycoprotein(s) such as IgG. Yet in some embodiments, the tested spots can correspond to glycoforms of glycoprotein(s) other than IgG. The glycoprofiles can be measured from the low abundant spot(s) such that each spot contains glycoprotein(s) in a quantity of less than about 100 ng, less than about 50 ng, less than about 10 ng, less than about 5 ng, less than about 2 ng or less than about 1 ng.

The identified biomarker(s) can be used for the same purposes as the glycosylation marker(s) such as diagnosing and monitoring a physiological condition such as a disease in a subject, monitoring an effect of a therapy on a subject by comparing a level of the marker before and after a treatment of the subject with a therapy. The methods of the invention can be directed to identification of one or more glycosylation markers of a disease associated with glycosylation changes such as an autoimmune disease, congenital disorder of glycosylation or cancer. The autoimmune disease can be, for example, rheumatoid arthritis, osteoarthritis, juvenile chronic arthritis, systematic lupus erythematosus, Sjögren's syndrome, ankylosing spondylitis, psoriatic arthritis, multiple sclerosis, inflammatory bowel disease, graft-vs-host disease or scleroderma. The cancer can be, for example, prostate cancer, pancreatic cancer, breast cancer, bladder cancer, renal cancer, colon cancer, ovary cancer, hepatocellular carcinoma, stomach cancer, or lung cancer. The methodology of the present invention as directed to rheumatoid arthritis and other autoimmune diseases is described in the U.S. provisional patent application No. 60/674,724 filed Apr. 26, 2005 "High throughput glycan analysis for diagnosing and monitoring rheumatoid arthritis and other autoimmune diseases" to Dwek et. al., and PCT application No. PCT/IB2005/002995 filed Jun. 24, 2005, which are both incorporated herein by reference in its entirety. The methodology of the present invention as directed to cancer is described in the U.S. provisional application No. 60/674,723 filed Apr. 26, 2005 "Glycosylation markers for cancer diagnostics and monitoring," to Dwek et. al. and PCT application No. PCT/IB2005/002531 filed Jun. 24, 2005 incorporated herein by reference in its entirety.

Releasing Glycans

Glycans can be released from a biological sample of a subject. The released glycans can be N-glycans or O-glycans. In some embodiments, releasing a glycan pool from glycoproteins of the biological sample can be carried out without purifying the glycoproteins. In other words, the released glycans are glycans of all or substantially all of the glycoproteins present in the sample rather than of one or more purified and isolated glycoproteins. In some embodiments, substantially all of the glycoproteins can mean all the glycoproteins that are recovered, yet in some embodiments substantially all of the glycoproteins can mean all the glycoproteins except those that are specifically removed. Releasing glycans can be carried out without exposing the sample to hydrazinolysis. In some embodiments, releasing glycans can be carried out from a very small sample of a body fluid. In some embodiments, the sample can be less than 100 microliters, or less than 50 microliters, or less than 20 microliters, or less than 10 microliters, or less than 5 microliters. The present methods of releasing can be optimized to work with samples of less than 1 microliters.

In some embodiments, releasing glycans can comprise releasing glycans from total glycoproteins from the biological sample in solution. Yet in some embodiments, releasing glycans can comprise immobilizing total glycoproteins of the sample, for example, on protein binding membrane or in a gel. The protein binding membrane can be any protein binding membrane, for example, polyvinylidene fluoride (PVDF) membrane, nylon membrane or Polytetrafluoroethylene (PTFE) membrane. In some embodiments, releasing glycans can further comprise releasing glycans from the total glycoproteins immobilized on the protein binding membrane or in the gel. When released glycans are N-linked glycans, releasing glycans from the immobilized glycoproteins can be carried out using enzymatic release with, for example, peptide N glycosidase F. When the glycoproteins are immobilized in the gel, releasing glycans can comprise separating the gel into a plurality of bands and selecting one or more bands from the plurality of bands from which the glycans are subsequently released (in gel band method). In some embodiments, releasing glycans from the gel can be carried out from the total gel, i.e. without separating gel into the bands. In some embodiments, releasing glycans is carried out by chemical release methods, such as β-elimination or ammonia-based β-elimination, which can be used for releasing N-linked or O-linked glycans from glycoproteins in solution or from glycoproteins immobilized on protein binding membrane. For using the methods of this invention in a high throughput format, it may be preferred to release a glycan pool from total glycoproteins immobilized in a gel or on a protein binding membrane as it can allow the use of smaller samples of body fluid or body tissue.

The details of some of the release methods and their applicability to both N-glycans and O-glycans are discussed below, however, it should be understood that the present invention is not limited to the discussed below release methods.

In-gel-band: This method can be used for N-glycan release from single glycopeptides in sodium dodecyl sulphate polyacrylamide gel electrophoresis (SDS PAGE) gel bands and is based on the method described in Kuster, B., Wheeler, S. F., Hunter, A. P., Dwek, R. A. and Harvey, D. J. (1997) "Sequencing of N-linked oligosaccharides directly from protein gels: in-gel deglycosylation followed by matrix-assisted laser desorption/ionization mass spectrometry and normal-phase high-performance liquid chromatography." *Anal-Biochem* 250: 82-101, incorporated herein by reference in its entirety. Samples can be reduced and alkylated by adding 4 µl of 5× sample buffer (5× sample buffer: 0.04 g Bromophenol blue, 0.625 ml 0.5M Tris (6 g for 100 ml) adjusted to pH 6.6 with HCl, 1 ml 10% SDS, 0.5 ml glycerol, in 2.875 ml water), 2 µl of 0.5M dithiothreitol (DTT) and water to make up to 20 µl in total, incubated at 70° C. for 10 min, then alkylated by addition of 2µl of 100 mM iodoacetamide and incubated for 30 min in the dark at room temperature. Samples can be then separated on SDS-PAGE gels after which the proteins are stained with Coomassie brilliant blue, the band of interest is excised and destained. Subsequently, the gel band can be cut into 1 $mm^3$ pieces and frozen for 2 hours or more (this can help break down the gel matrix). This gel band can be then washed alternatively with 1 ml of acetonitrile then 1 ml of digestion buffer (20 mM $NaHCO_3$ pH 7), which can be repeated twice before the gel plug can be then dried. PNGase F buffer solution (30 µl of 100 U/ml) is added (this is enough for 10-15 $mm^3$ gel), more enzyme solution is added if larger gel bands can be used. The PNGaseF and gel pieces can be incubated overnight at 37° C. The supernatant can be recovered along with 3×200 µl water washes (with sonication with gel pieces for 30 mins each) followed by an acetonitrile wash (to squeeze out the gel), another water wash and a final acetonitrile wash. Samples can be filtered through a 0.45 µm LH Millipore filter and dried down for fluorescent labeling.

In-gel-block: To avoid the problems with clean up of samples following solution phase enzymatic glycan release an in-gel-block release from protein mixtures can be used. Briefly, the whole protein mixture (e.g. serum or plasma) can be reduced and alkylated as in the In-gel band oligosaccharide release described above, then set into 15% SDS-gel mixture but without bromophenol blue. A total volume of gel of 185 µl can be used (initially set into a 48 well plate, then removed for cutting up) with 300 µl of 100 U/ml of PNGaseF. The washing procedures can be similar to those used for in-gel-band release. Washing of gel can allow separation of the glycan pool from the parent proteins and thus provides glycans suitable for fluorescent labeling and further HPLC analysis. The in-gel-block procedure can be more suitable for automated glycan release than in-solution PNGaseF release, and can be the preferred method for high throughput glycan analysis.

This in-gel-block method has been further modified to work with smaller amounts of gel set into a 96 well plate. One can reduce and alkylate 5 µl of serum, in a polypropylene 96 well flat bottomed microplate, then set the sample into a gel-block by adding 30% (w/w) acrylamide: 0.8% (w/v) bis-acrylamide stock solution (37.5:1) (Protogel ultrapure protein and sequencing electrophoresis grade, gas stabilised; National Diagnostics, Hessle, Hull, UK), 1.5M Tris pH 8.8, 10% SDS, 10% APS (ammonium peroxodisulphate) and finally TEMED (N,N,N,N'-Tetramethyl-ethylenediamine) mixing then leave it to set. The gel blocks can be then transferred to a filter plate (Whatman protein precipitation plate) then washed with acetonitrile followed by 20 mM $NaHCO_3$. The gel pieces can be then dried in a vacuum centrifuge, incubated with 1% formic acid at for 40 min and then re-dried. The N-glycans can be released incubating with PNGaseF solution (Roche Diagnostics GmbH, Mannheim, Germany. The released glycans can be collected into a 2 ml square tapered polypropylene 96 well plate by washing the gel pieces with water followed by acetonitrile. The released glycans can be dried then labeled by incubating with 2-AB labelling solution (LudgerTag 2-AB labelling kit), for 2 hours at 65° C. Excess 2AB can be removed using a HILIC solid phase extraction (SPE) micro-elution plate (Waters) in a vacuum manifold. The labeled glycans can then eluted into a 2 ml 96 well then dried and redissolved them in 50 mM ammonium formate and acetonitrile ready for HPLC.

Enzymatic release of N-glycans from PVDF membranes. The glycoproteins in reduced and denatured serum samples can be attached to a hydrophobic PVDF membrane in a 96 well plate by simple filtration. The samples can be then washed to remove contaminates, incubated with PNGaseF to release the glycans based on the methods described in Papac, D. I., et. al. *Glycobiology* 8: 445-54, 1998, and in Callewaert, N., et. al. *Electrophoresis* 25: 3128-31, 2004, both incorporated herein by reference in their entirety. The N-glycans can be then washed from the bound protein, collected and dried down ready for fluorescent labeling. N-glycans can be released in situ from the glycoproteins by incubation with PNGaseF and by chemical means. The 2AB labeled N-glycans can be cleaned by SPE as in the in-gel-block method.

Chemical release of N- and O-glycans. In contrast to the advantages that enzymatic release of N-glycans can afford to N-glycan analysis, no enzymatic methodology currently exists for the release of structurally intact O-glycans. Chemical release by reductive β-elimination can require the concomitant reduction of the released oligosaccharides to their alditol derivatives (Amano, J. et. al. *Methods Enzymol* 179: 261-70, 1989) to prevent degradation (peeling). This reduction precludes the use of any post-release labeling so that detection is limited to mass spectrometry, pulsed amperometric detection and/or radioactivity.

Ammonia-based β-elimination can be used to release both N- and O-glycans by a modification of the classical β-elimination (Huang, Y. et. al. *Analytical Chemistry* 73: 6063-6069, 2001) which can be applied to glycoproteins in solution or on PVDF membranes. Ammonia-based β-elimination can be done from PVDF membranes. This strategy, can be optimized for high throughput, and can provide a powerful approach for releasing both N- and O-glycans in their correct molar proportions and in an open ring form suitable for post-release labeling.

Release of N- and O-glycans from protein binding PVDF membranes by ammonia based beta-elimination. Samples of glycoprotein, mixtures of glycoproteins, whole serum or other body fluids can be reduced and alkylated as in the in-gel-band method. Protein binding PVDF membranes (Durapore 13 mm×0.45 µm HVHP, Millipore) in Swinnex filter holders (Millipore) can be pre-washed with 2×2.5 ml water using an all-polypropylene 2.5 ml syringe (Sigma), followed by a syringe full of air to remove most of the liquid from the membrane. The reduced and alkylated sample can be then applied directly to the membrane and left to bind for 5 min before washing by pushing through 2×2.5 ml water slowly with a syringe, followed by a syringe full of air to remove most of the liquid from the membrane. The filter with the bound glycoprotein samples can be then carefully removed from the filter holder and placed in a 1.5 ml screw capped polypropylene tube with a molded PTFE cap. 1 ml of ammonium carbonate saturated 29.2% aqueous ammonium hydroxide, plus 100 mg ammonium carbonate can be added to the tube. This can be incubated for 40 hours at 60° C., then cooled in the fridge. The liquid can be then transferred to a clean tube and evaporated to dryness. The released glycans can be re-dissolved in water and re-dried until most of the salts are removed. 100 µl of 0.5M boric acid can be added to the glycans and incubated at 37° C. for 30 min. The glycans can be then dried under vacuum, 1 ml methanol added, re-dried, a further 1 ml methanol can be added and re-dried to remove the boric acid.

Quantitatively Analyzing the Glycans

Labeling of glycans. In some embodiments, upon releasing, the glycans can be labeled with, for example, a fluorescent label or a radioactive label. The fluorescent label can be, for example, 2-aminopyridine (2-AP), 2-aminobenzamide (2-AB), 2-aminoanthranilic acid (2-AA), 2-aminoacridone (AMAC) or 8-aminonaphthalene-1,3,6-trisulfonic acid (ANTS). Labeling of glycans with fluorescent labels is described, for example, by Bigge, J. C., et. al. "Nonselective and efficient fluorescent labeling of glycans using 2-amino benzamide and anthranilic acid." *Anal Biochem* 230: 229-38, 1995, incorporated herein reference in its entirety, and Anumula, K. R. (2000). High-sensitivity and high-resolution methods for glycoprotein analysis. Analytical Biochemistry 283: 17-26, incorporated herein by reference in its entirety. Fluorescent labels can label all glycans efficiently and non-selectively and can enable detection and quantification of glycans in the sub picomole range. The choice of fluorescent label depends on the separation technique used. For example, a charged label is specifically required for capillary electrophoresis. In particular, 2-AB label can be preferred for chromatographic, enzymatic and mass spectroscopic processes and analyses, while 2-AA label can be preferred for electrophoretic analyses. Unlabelled glycans can be also detected by, for example, mass spectrometry, however, fluorescent labelling may aid glycan ionisation, see e.g. Harvey, D. J. (1999). "Matrix-assisted laser desorption/ionization mass spectrometry of carbohydrates." *Mass Spectrom Rev* 18: 349-450; Harvey, D. J. (2000). Electrospray mass spectrometry and fragmentation of N-linked carbohydrates derivatized at the reducing terminus. J Am Soc Mass Spectrom 11: 900-915.

Measuring glycoprofile of the released glycans. Glycoprofile of the glycans means a presentation of particular glycan structures in the glycan pool. For example, when measured by HPLC, a glycoprofile can be a chromatogram comprising a plurality of peaks corresponding to glycan structures in the glycan pool. When measured by mass spectrometry, a glycoprofile can be a mass spectrum comprising a plurality of fragmentation patterns corresponding to glycan structures in the glycan pool. Measuring the glycoprofile of the glycans can be carried out by quantitative analytical technique, such as chromatography, mass spectrometry, electrophoresis or a combination thereof. In particular, the chromatographic technique can be high performance anion exchange chromatography (HPAEC), weak ion exchange chromatography (WAX), gel permeation chromatography (GPC), high performance liquid chromatography (HPLC), normal phase high performance liquid chromatography (NP-HPLC), reverse phase HPLC (RP-HPLC), or porous graphite carbon HPLC (PGC-HPLC). The mass spectrometry technique can be, for example, matrix assisted laser desorption/ionization time of flight mass spectrometry (MALDI-TOF-MS), electrospray ionization time of flight mass spectrometry (ESI-TOF-MS), positive or negative ion mass spectrometry or liquid chromatography mass spectrometry (LC-MS). The electrophoretic technique can be, for example, gel electrophoresis or capillary electrophoresis. The use of these quantitative analytical techniques for analyzing glycans is described, for example, in the following publications:

1) Guile, G. R., Wong, S. Y. and Dwek, R. A. (1994). "Analytical and preparative separation of anionic oligosaccharides by weak anion-exchange high-performance liquid chromatography on an inert polymer column." *Analytical Biochemistry* 222: 231-5 for HPLC, incorporated herein by reference in its entirety;
2) Butler, M., Quelhas, D., Critchley, A. J., Carchon, H., Hebestreit, H. F., Hibbert, R. G., Vilarinho, L., Teles, E., Matthijs, G., Schollen, E., Argibay, P., Harvey, D. J., Dwek, R. A., Jaeken, J. and Rudd, P. M. (2003). "Detailed glycan analysis of serum glycoproteins of patients with congenital disorders of glycosylation indicates the specific defective glycan processing step and provides an insight into pathogenesis." *Glycobiology* 13: 601-22, for MALDI-MS, NP-HPLC and ESI-liquid chromatography/MS, incorporated herein by reference in its entirety;
3) Jackson, P., Pluskal, M. G. and Skea, W. (1994). "The use of polyacrylamide gel electrophoresis for the analysis of acidic glycans labeled with the fluorophore 2-aminoacridone." *Electrophoresis* 15: 896-902, for polyacrylamide gel electrophoresis (PAGE), incorporated herein by reference in its entirety;
4) Hardy, M. R. and Townsend, R. R. (1994). "High-pH anion-exchange chromatography of glycoprotein-derived carbohydrates." *Methods Enzymol* 230: 208-25, for HPAEC using pulsed amperometric detection (PAD), incorporated herein by reference in its entirety;
5) Callewaert, N., Contreras, R., Mitnik-Gankin, L., Carey, L., Matsudaira, P. and Ehrlich, D. (2004). "Total serum protein N-glycome profiling on a capillary electrophoresis-microfluidics platform." *Electrophoresis* 25: 3128-31 for capillary electrophoresis, incorporated herein by reference in its entirety;
6) Guile, G. R., Rudd, P. M., Wing, D. R., Prime, S. B. and Dwek, R. A. (1996). "A rapid high-resolution high-performance liquid chromatographic method for separating glycan mixtures and analyzing oligosaccharide profiles." *Anal Biochem* 240: 210-26, for HPLC, incorporated herein by reference in its entirety;
7) Caesar, J. P., Jr., Sheeley, D. M. and Reinhold, V. N. (1990). "Femtomole oligosaccharide detection using a reducing-end derivative and chemical ionization mass spectrometry." *Anal Biochem* 191: 247-52, for LC-MS, incorporated herein by reference in its entirety;
8) Mattu, T. S., Royle, L., Langridge, J., Wormald, M. R., Van den Steen, P. E., Van Damme, J., Opdenakker, G., Harvey, D. J., Dwek, R. A. and Rudd, P. M. (2000). "O-glycan analysis of natural human neutrophil gelatinase B using a combination of normal phase-HPLC and online tandem mass spectrometry: implications for the domain organization of the enzyme." *Biochemistry* 39: 15695-704, for NP-HPLC and MS, incorporated herein by reference in its entirety;
9) Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90, for NP-HPLC and MS, incorporated herein by reference in its entirety;
10) Anumula, K. R. and Du, P. (1999). "Characterization of carbohydrates using highly fluorescent 2-aminobenzoic acid tag following gel electrophoresis of glycoproteins." *Anal Biochem* 275: 236-42, for gel electrophoresis, incorporated herein by reference in its entirety;
11) Huang, Y. and Mechref, Y. (2001). "Microscale nonreductive release of O-linked glycans for subsequent analysis through MALDI mass spectrometry and capillary electrophoresis." *Analytical Chemistry* 73: 6063-6069, for a combination of MALDI-MS and capillary electrophoresis, incorporated herein by reference in its entirety;
12) Burlingame, A. L. (1996). "Characterization of protein glycosylation by mass spectrometry." *Curr Opin Biotechnol* 7: 4-10, for mass spectrometry, incorporated herein by reference in its entirety;
13) Costello, C. E. (1999). "Bioanalytic applications of mass spectrometry." *Curr Opin Biotechnol* 10: 22-8, for mass spectrometry, incorporated herein by reference in its entirety;
14) Davies, M. J. and Hounsell, E. F. (1996). "Comparison of separation modes of high-performance liquid chromatography for the analysis of glycoprotein- and proteoglycan-derived oligosaccharides." *J Chromatogr A* 720: 227-33, for HPLC, incorporated herein by reference in its entirety;
15) El Rassi, Z. (1999). "Recent developments in capillary electrophoresis and capillary electrochromatography of carbohydrate species." *Electrophoresis* 20: 3134-44, for capillary electrophoresis and capillary electrochromatography, incorporated herein by reference in its entirety;
16) Kuster, B., Wheeler, S. F., Hunter, A. P., Dwek, R. A. and Harvey, D. J. (1997). "Sequencing of N-linked oligosaccharides directly from protein gels: in-gel deglycosylation followed by matrix-assisted laser desorption/ionization mass spectrometry and normal-phase high-performance liquid chromatography." *Anal-Biochem* 250: 82-101, for NP-HPLC and MALDI-MS, incorporated herein by reference in its entirety;
17) Reinhold, V. N., Reinhold, B. B. and Chan, S. (1996). "Carbohydrate sequence analysis by electrospray ionization-mass spectrometry." *Methods Enzymol* 271: 377-402, for ESI-MS, incorporated herein by reference in its entirety;
18) Mattu, T. S., Pleass, R. J., Willis, A. C., Kilian, M., Wormald, M. R., Lellouch, A. C., Rudd, P. M., Woof, J. M. and Dwek, R. A. (1998). "The glycosylation and structure of human serum IgA1, Fab, and Fc regions and the role of N-glycosylation on Fc alpha receptor interactions." *Journal of Biological Chemistry* 273: 2260-72, for WAX and NP-HPLC, incorporated herein by reference in its entirety.
19) Callewaert, N., Schollen, E., Vanhecke, A., Jaeken, J., Matthijs, G., and Contreras, R. (2003). Increased fucosylation and reduced branching of serum glycoprotein N-glycans in all known subtypes of congenital disorder of glycosylation I. Glycobiology 13: 367-375, incorporated herein by reference in its entirety.
20) Block, T. M. Comunale, M. A., Lowman, M., Steel, L. F., Romano, P. R., Fimmel, C., Tennant, B. C. London, A. A. Evans, B. S. Blumberg, R. A. Dwek, T. S. Mattu and A. S. Mehta, "Use of targeted glycoproteomics to identify serum glycoproteins that correlate with liver cancer in woodchucks and humans." PNAS USA (2005) 102, 779-784, incorporated herein by reference in its entirety.
21) D. J. Harvey, Fragmentation of negative ions from carbohydrates: Part 1; Use of nitrate and other anionic adducts for the production of negative ion electrospray spectra from N-linked carbohydrates, *J. Am. Soc. Mass Spectrom.*, 2005, 16, 622-630, incorporated herein by reference in its entirety.
22) D. J. Harvey, Fragmentation of negative ions from carbohydrates: Part 2, Fragmentation of high-mannose N-linked glycans, *J. Am. Soc. Mass Spectrom.*, 2005, 16, 631-646, incorporated herein by reference in its entirety;
23) D. J. Harvey, Fragmentation of negative ions from carbohydrates: Part 3, Fragmentation of hybrid and complex N-linked glycans, *J. Am. Soc. Mass Spectrom.*, 2005, 16, 647-659, incorporated, herein by reference in its entirety.

Although many techniques can be used for measuring glycoprofiles, in the method of determining one or more glycosylation markers of a physiological condition such as a disease or a stage of disease, it can be preferred to measure glycoprofiles by high performance liquid chromatography (HPLC) alone or in combination with mass spectrometry. For example, measuring glycoprofiles can be performed by gel electrophoresis (see Jackson, P., Pluskal, M. G. and Skea, W. (1994). "The use of polyacrylamide gel electrophoresis for the analysis of acidic glycans labeled with the fluorophore 2-aminoacridone." *Electrophoresis* 15: 896-902); HPAEC using pulsed amperometric detection (PAD) (Townsend, R. R., Hardy, M. R., Hindsgaul, O. and Lee, Y. C. (1988). "High-performance anion-exchange chromatography of oligosaccharides using pellicular resins and pulsed amperometric detection." *Anal Biochem* 174: 459-70; and Hardy, M. R. and Townsend, R. R. (1994). "High-pH anion-exchange chromatography of glycoprotein-derived carbohydrates." *Methods Enzymol* 230: 208-25); or capillary electrophoresis (see El Rassi, Z. (1999). "Recent developments in capillary electrophoresis and capillary electrochromatography of carbohydrate species." *Electrophoresis* 20: 3134-44), however, these techniques are not ideally suited to large-scale automation, nor do they provide full quantitative structural analysis. In general they have poor detection limits, low reproducibility and are restricted by the inherent difficulty of obtaining full structural characterization of the oligosaccharides and the lack of predictability that is required to enable the preliminary assignments to be made to novel structures.

Measuring a glycoprofile by quantitative HPLC, i.e. measuring a glycoprofile of fluorescently labeled glycans such as 2AB labeled glycans by HPLC can allow accurate quantification and structural assignment of the glycan structures in the glycan pool by integration of the peaks in the chromatogram. The fluorescent labeling is non-selective and adds one fluorescent label per glycan, thus, allowing a direct correlation between fluorescence measured as peak area or height and the amount of each glycan. For an HPLC measured glycoprofile, glycan structures present in the analyzed glycan pool are separated based on their elution time. For NP-HPLC, the elution times can be converted to glucose units by comparison with a standard dextran hydrolysate ladder. An HPLC measured glycoprofile can trace all glycan structures present in a glycan pool in correct molar proportions. Polar functional groups of stationary phase of HPLC can interact with the hydroxyl groups of the glycans in a manner that is reproducible for a particular monosaccharide linked in a specific manner. For example, the contribution of the outer arm fucose addition is much greater than the addition of a core fucose residue; a core fucose residue always contributes 0.5 glucose units (gu) to the overall elution position. The characteristic incremental values associated with different monosaccharide additions can allow the preliminary assignment of a predicted structure for a particular peak present in the glycoprofile. This structure can be then confirmed by digestion with exoglycosidase arrays and/or mass spectrometry. Other techniques, such as capillary electrophoresis are not as predictable as NP-HPLC. Although, CE migration times can be calibrated with standards, the migration times of unknown structures can not be easily predicted. Measuring glycoprofiles by NP-HPLC can be also preferred for the following reason. Digestion of a glycan pool with one or more exoglycosidases removes monosaccharide residues and, thus, decreases the retention times or associated gu values in the glycoprofile measured by NP-HPLC. In some embodiments, this can enable the segregation of the peaks that are associated with one or glycosylation markers by shifting away peaks that are not related to the glycosylation changes away from the measured region of the glycoprofile.

In some embodiments, measuring glycoprofiles can be carried out using reverse phase high performance liquid chromatography. For RP-HPLC measured glycoprofiles, the elution times can be converted into arabinose units using a standard arabinose ladder. The use of RP-HPLC for measuring glycosylation profiles is described, for example, in Guile, G. R., Harvey, D. J., O'Donnell, N., Powell, A. K., Hunter, A. P., Zamze, S., Fernandes, D. L., Dwek, R. A., and Wing, D. R. (1998). "Identification of highly fucosylated N-linked oligosaccharides from the human parotid gland. European Journal of Biochemistry" 258: 623-656; Royle, L., Mattu, T. S., Hart, E., Langridge, J. I., Merry, A. H., Murphy, N., Harvey, D. J., Dwek, R. A., and Rudd, P. M. (2002). An analytical and structural database provides a strategy for sequencing O-glycans from microgram quantities of glycoproteins. Analytical Biochemistry 304: 70-90, incorporated herein by reference. RP-HPLC measured glycoprofiles can be used to complement glycoprofiles measured by NP-HPLC. For example, RP-HPLC can separate bisected glycan structures from glycan structures that do not contain bisecting N-acetylglucoamine residue. In NP-HPLC measured glycoprofiles these structures can be too close to be resolved. In some embodiments, measuring glycoprofiles by RP-HPLC can comprise using one or more buffers. The mobile phase can be used, for example, to improve the reproducibility of the measurement. The buffer can be, for example, solvent A: 50 mM of ammonium formate adjusted to pH5 with triethylamine and solvent B: solvent A and acetonitrile mixed 50/50.

In some embodiments, HPLC can be used as a preparative method for collecting glycans, i.e. HPLC can be used to isolate unusual glycans for further analysis, by e.g. mass spectrometry, as well as for obtaining parameters for a glycan database.

In some embodiments, each of the glycoprofiles can be presented as a plurality of peaks corresponding to glycan structures in the glycans. In the method of determining one or more glycosylation markers, a peak ratio means a ratio between any one or more peaks and any other one or more peaks within the same glycosylation profile. In the method of determining a glycosylation marker, comparing peak ratios can mean comparing peaks intensities or comparing integrated areas under the peaks. In some embodiments of the method of determining glycosylation marker, comparing peak ratios can be carried for glycans of the tested and control samples which were not digested with one or more exoglycosidases. In some embodiments, comparing peak ratios can be carried out on the glycans which were digested with one or more exoglycosidases. In some embodiments, comparing peak ratios can be carried out for the glycans which were not digested with exoglycosidase and for the glycans digested with one or more exoglycosidases.

In some embodiments, measuring glycoprofiles with HPLC can be complemented with a mass spectrometry measurement. Complementary mass spectrometry data, such as MALDI, ESI or LC/MS) can serve, for example, for validation HPLC measured glycoprofiles as a separate orthogonal technique able to resolve the structures of more complex glycans when a sufficient amount of sample of a body fluid or a body tissue is available. Mass spectrometry used in combination with HPLC can be a powerful tool for structural analysis of glycoproteins. Mass spectrometry alone can be used for structural analysis of glycans providing monosaccharide composition of glycans. However, mass spectrometry used by itself does not distinguish isobaric monosaccharide (and hence oligosaccharides or glycans) and does not provide the information on monosaccharide linkage in glycans. The LC-MS/(MS) techniques can provide the most informative data out of the mass spectrometry technique, see Caesar, J. P., Jr., Sheeley, D. M. and Reinhold, V. N. (1990). "Femtomole oligosaccharide detection using a reducing-end derivative and chemical ionization mass spectrometry." *Anal Biochem* 191: 247-52; Mattu, T. S., Pleass, R. J., Willis, A. C., Kilian, M., Wormald, M. R., Lellouch, A. C., Rudd, P. M., Woof, J. M. and Dwek, R. A. (1998). "The glycosylation and structure of human serum IgA1, Fab, and Fc regions and the role of N-glycosylation on Fc alpha receptor interactions." *Journal of Biological Chemistry* 273: 2260-72; and Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90. In some embodiments, measuring glycoprofiles by LC/MS can comprise using the LC stage of LC/MS not only for cleanup and preliminary separation of glycans before they enter the MS stage of LC/MS but for obtaining preliminary assignment of glycan structures in the glycans. This can be accomplished, for example, by using NP-HPLC matrix, for example NP-HPLC with TSK gel amide 80 matrix, in the LC column of LC/MS. In NP-HPLC with TSK gel amide 80 matrix, hydroxyl groups of glycans interact with the amide functionality, therefore, the elution order is determined by the number of hydroxyl groups in a particular glycan, its molecular confirmation and its relative solubility in the mobile phase.

In some embodiments, when the glycan pool comprises charged glycans, the glycan pool can be fractioned into several aliquots based upon charge. Fractioning of the glycan pool can be carried out, for example, by weak ion exchange (WAX) chromatography. Each WAX aliquot can be then analyzed independently by NP-HPLC combined with exoglycosidase digestions. Measuring glycoprofiles by WAX HPLC is described, for example, in Guile, G. R., Wong, S. Y. and Dwek, R. A. (1994). "Analytical and preparative separation of anionic oligosaccharides by weak anion-exchange high-performance liquid chromatography on an inert polymer column." *Analytical Biochemistry* 222: 231-5.

Measuring glycoprofile of the glycans with the above described methods can allow detecting a particular glycan structure present in the glycans in subpicomole levels. Accordingly, in some of the embodiments, measuring glycoprofiles of the glycans is carried out using a technique able to detect a glycan structure present in the glycans in amount of 1 picomole, preferably 0.1 picomole, yet more preferably 0.01 picomole. Exoglycosidase digestion. In some embodiments, the released glycans can be subjected to further enzymatic digestion with one or more enzymes. The enzymatic digestion can be done using any suitable enzymes, such as glycosidases. Examples of suitable glycosidases include, but are not limited to sialidase, β-galactosidase, fucosidase α1-6, 2>>3,4, α1-3,4, α1-2 fucosidase, alpha-amylase, beta-amylase, glucan 1,4-alpha-glucosidase, cellulase, endo-1,3(4)-beta-glucanase, inulinase, endo-1,4-beta-xylanase, oligosaccharide alpha-1,6-glucosidase, dextranase, chitinase, polygalacturonase, lysozyme, exo-alpha-sialidase, alpha-glucosidase, beta-glucosidase, alpha-galactosidase, beta-galactosidase, alpha-mannosidase, beta-mannosidase, beta-fructofuranosidase, alpha,alpha-trehalase, beta-glucuronidase, xylan endo-1,3-beta-xylosidase, amylo-alpha-1,6-glucosidase, hyaluronoglucosaminidase, hyaluronoglucuronidase, xylan 1,4-beta-xylosidase, beta-D-fucosidase, glucan endo-1,3-beta-D-glucosidase, alpha-L-rhamnosidase, pullulanase, GDP-glucosidase, beta-L-rhamnosidase, fucoidanase, glucosylceramidase, galactosylceramidase, galactosylgalactosylglucosylceramidase, sucrose alpha-glucosidase, alpha-N-acetylgalactosaminidase, alpha-N-acetylglucosaminidase, alpha-L-fucosidase, beta-N-acetylhexosaminidase, beta-N-acetylgalactosaminidase, cyclomaltodextrinase, alpha-L-arabinofuranosidase, glucuronosyl-disulfoglucosamine glucuronidase, isopullulanase, glucan 1,3-beta-glucosidase, glucan endo-1,3-alpha-glucosidase, glucan 1,4-alpha-maltotetrahydrolase, mycodextranase, glycosylceramidase, 1,2-alpha-L-fucosidase, 2,6-beta-fructan 6-levanbiohydrolase, levanase, quercitrinase, galacturan 1,4-alpha-galacturonidase, isoamylase, glucan 1,6-alpha-glucosidase, glucan endo-1,2-beta-glucosidase, xylan 1,3-beta-xylosidase, licheninase, glucan 1,4-beta-glucosidase, glucan endo-1,6-beta-glucosidase, L-iduronidase, mannan 1,2-(1,3)-alpha-mannosidase, mannan endo-1,4-beta-mannosidase, fructan beta-fructosidase, agarase, exo-poly-alpha-galacturonosidase, kappa-carrageenase, glucan 1,3-alpha-glucosidase, 6-phospho-beta-galactosidase, 6-phospho-beta-glucosidase, capsular-polysaccharide endo-1,3-alpha-galactosidase, beta-L-arabinosidase, arabinogalactan endo-1,4-beta-galactosidase, cellulose 1,4-beta-cellobiosidase, peptidoglycan beta-N-acetylmuramidase, alpha, alpha-phosphotrehalase, glucan 1,6-alpha-isomaltosidase, dextran 1,6-alpha-isomaltotriosidase, mannosyl-glycoprotein endo-beta-N-acetylglucosamidase, glycopeptide alpha-N-acetylgalactosaminidase, glucan 1,4-alpha-maltohexaosidase, arabinan endo-1,5-alpha-L-arabinosidase, mannan 1,4-beta-mannobiosidase, mannan endo-1,6-beta-mannosidase, blood-group-substance endo-1,4-beta-galactosidase, keratan-sulfate endo-1,4-beta-galactosidase, steryl-beta-glucosidase, strictosidine beta-glucosidase, mannosyl-oligosaccharide glucosidase, protein-glucosylgalactosylhydroxylysine glucosidase, lactase, endogalactosaminidase, mucinaminylserine mucinaminidase, 1,3-alpha-L-fucosidase, 2-deoxyglucosidase, mannosyl-oligosaccharide 1,2-alpha-mannosidase, mannosyl-oligosaccharide 1,3-1,6-alpha-mannosidase, branched-dextran exo-1,2-alpha-glucosidase, glucan 1,4-alpha-maltotriohydrolase, amygdalin beta-glucosidase, prunasin beta-glucosidase, vicianin beta-glucosidase, oligoxyloglucan beta-glycosidase, polymannuronate hydrolase, maltose-6'-phosphate glucosidase, endoglycosylceramidase, 3-deoxy-2-octulosonidase, raucaffricine beta-glucosidase, coniferin beta-glucosidase, 1,6-alpha-L-fucosidase, glycyrrhizinate beta-glucuronidase, endo-alpha-sialidase, glycoprotein endo-alpha-1,2-mannosidase, xylan alpha-1,2-glucuronosidase, chitosanase, glucan 1,4-alpha-maltohydrolase, difructose-anhydride synthase, neopullulanase, glucuronoarabinoxylan endo-1,4-beta-xylanase, mannan exo-1,2-1,6-alpha-mannosidase, anhydrosialidase, alpha-glucosiduronase, lacto-N-biosidase, 4-alpha-D-{(1->4)-alpha-D-glucano}trehalose trehalohydrolase, limit dextrinase, poly(ADP-ribose) glycohydrolase, 3-deoxyoctulosonase, galactan 1,3-beta-galactosidase, beta-galactofuranosidase, thioglucosidase, ribosylhomocysteinase, beta-primeverosidase. Most preferably, enzymatic digestion is carried out with one or more exoglycosidases listed in table 1.

Figure 3:
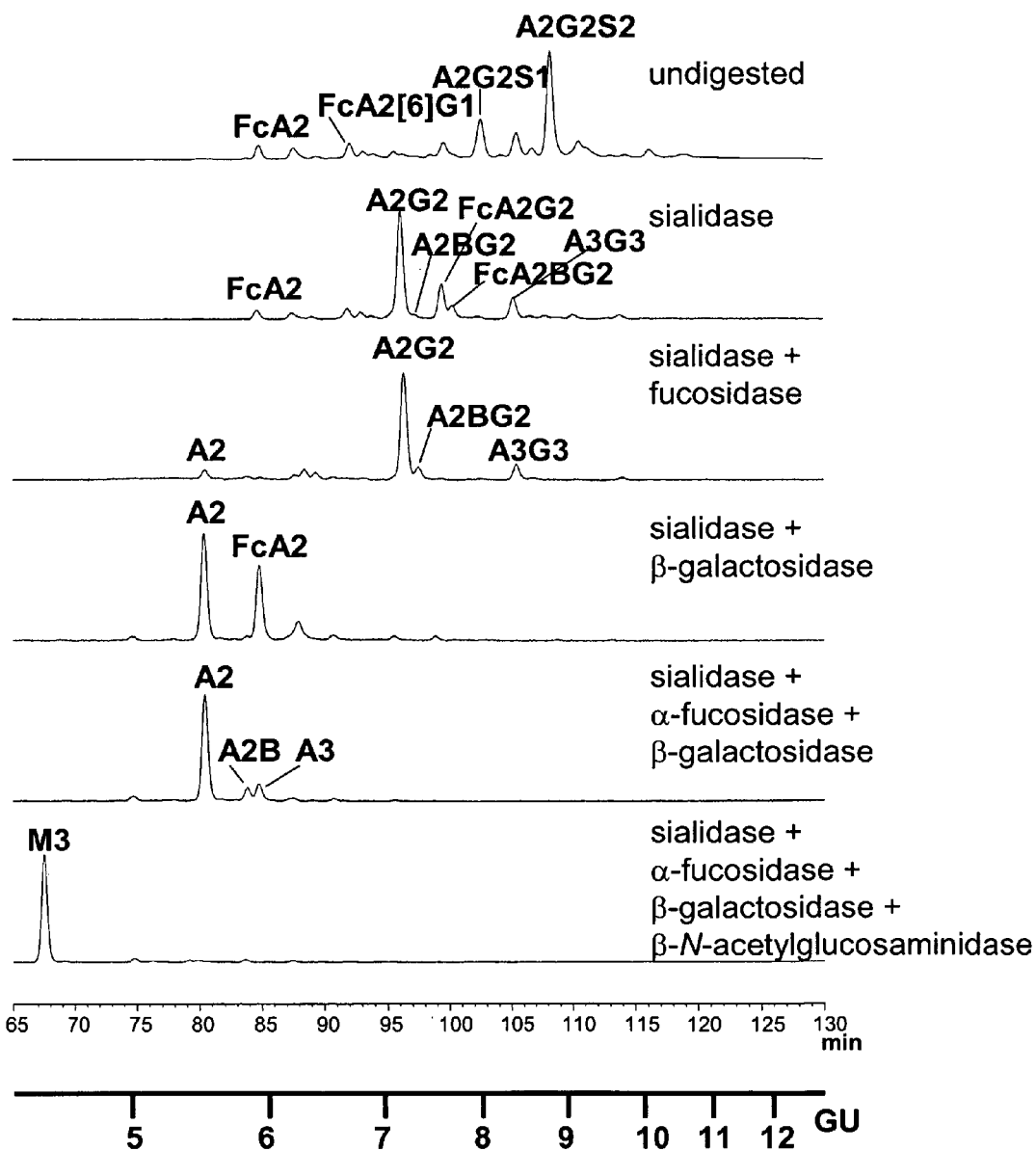
FIG. 3 shows normal phase high performance liquid chromatography (NP-HPLC) profiles of 2-AB labeled N-glycans released from whole serum following digestion with an array of exoglycosidases.

For example, FIG. 3 illustrates NP-HPLC measured glycoprofiles of 2-AB labeled N-linked glycans released from whole serum after following digestion with an array of exoglycosidases. Only major peaks are annotated on FIG. 3, abbreviations used correspond to Table 2. In some embodiments, the enzymatic digestion can be sequential, so not all monosaccharides are removed at once. The digested glycans can be analyzed after each digestion step to obtain a glycosylation profile. In some embodiments, the enzymatic digestion can be digestion with an array comprising one or more exoglycosidases. Digestion with an array means using a panel of exoglycosidases in various combinations to provide several digestion profiles on aliquots of a pool of glycans. Each exoglycosidase enzyme removes specific terminal monosaccharides attached in defined linkages. In an array, the exoglycosidase enzymes act sequentially depending on their specificity.

In some embodiments, digestion with one or more exoglycosidases in any combination can be used to segregate the glycosylation marker(s) by shifting glycan structures that do not contain the marker from the measured region of the glycoprofile. In some embodiments of the invention, digestion with one or more exoglycosidases in any combination can be used to amplify the glycosylation marker(s) by digesting away monosaccharides that are attached to some of the markers oligosaccharides but are not essential feature of the markers. In some embodiments of the invention, digestion with one or more exoglycosidases can be used to both amplify and segregate the glycosylation marker(s). The use of digestion with one or more exoglycosidases to segregate and/or amplify glycosylation markers is illustrated, for example, in the US provisional application "Glycosylation Markers for Cancer

TABLE 1

| Exoglycosidase Specificities | |
|---|---|
| Sialidase α-(2-3,6,8) | Cleaves all non-reducing terminal branched and unbranched sialic acids |
| Sialidase α-(2-3) | Cleaves the non-reducing terminal alpha-(2-3) unbranched sialic acid residues from complex carbohydrates and glycoproteins. |
| α-(1-3,4,6)-galactosidase | Cleaves α-(1-3)-, α-(1-4)-and α-(1-6)-linked, non-reducing terminal galactose from complex carbohydrates and glycoproteins. Fucose linked to the penultimate N-acetylglucosamine will block cleavage of the galactose. |
| β-(1-4)-galactosidase | Cleaves Non-reducing terminal β-(1-4)-galactose. Fucose linked to the penultimate N-acetylglucosamine will block cleavage of the galactose. |
| β-(1-3,4,6)-galactosidase | Cleaves all β1-3 and β1-4 linked non-reducing, terminal galactose. Fucose linked to the penultimate N-acetylglucosamine will block cleavage of the galactose. |
| β-(1-3,6)-galactosidase | Cleaves β-(1-3)- and β-(1-6)-linked, non-reducing terminal galactose from complex carbohydrates and glycoproteins. Fucose, but not sialic acid, linked to the penultimate N-acetylglucosamine will block cleavage. |
| β-N-acetylglucosaminidase | Cleaves all non-reducing terminal β-linked N-acetylglucosamine. Bisecting GlcNAc slows the reaction. |
| β-N-acetylhexosaminidase | Cleaves all non-reducing terminal β-linked N-acetylglucosamine and N-acetylgalacosamine. Bisecting GlcNAc slows the reaction |
| α-(1-2,3,6)-mannosidase | Cleaves all α-(1-2,3,6)-linked mannose. |
| α-(1-6)-core mannosidase | Cleaves unbranched, terminal non-reducing mannose linked alpha-(1-6) to the mannosyl chitobiose core. The presence of a branched mannose alpha-(1-3) will inhibit the removal of the 1-6 mannose. |
| α-(1-3,4)-fucosidase | Cleaves non-reducing terminal branched fucose when linked alpha-(1-3) or alpha-(1-4) to GlcNAc. |
| α-(1-6>2>>3,4)-fucosidase | Cleaves non-reducing terminal branched fucose when linked alpha-(1-6) to GlcNAc or Gal. Will also cleave alpha-(1-2) and alpha-(1-3,4) with reduced efficiency |
| α-(1-2)-fucosidase | Cleaves non-reducing terminal branched fucose when linked alpha-(1-2) to a Gal. |

Diagnostics and Monitoring" to Dwek et. al. filed Apr. 26, 2005, incorporated herein by reference in its entirety.

In some embodiments, measuring glycoprofiles can reveal one or more peaks which can not be assigned to previously reported glycan structures or structures that are not fully digested by the enzyme array panels. In this case, the digestion with one or more exoglycosidases can be used to segregate these one or peaks for further analysis. The HPLC based technology allows such glycans to be recovered from the HPLC eluate for further analysis.

Databases. Measuring glycoprofile of the glycans can comprise constructing a database of glycan structures of the glycans. The parameters of this database can be, for example, glycan structure along with: elution times (from HPLC data); mass and composition (from MS data); experimentally determined and/or predicted glycan structures, elution times, mass and composition, following treatment with exoglycosidase enzymes; experimentally determined and/or predicted glycan structures, mass and composition following MS fragmentation. The database can, for example, make preliminary and final assignments of the glycan structures as well as recommend the appropriate exoglycosidase arrays to confirm preliminary assignments. The use of databases in measuring glycoprofiles is described, for example, in the following references:

1) Mattu, T. S., Royle, L., Langridge, J., Wormald, M. R., Van den Steen, P. E., Van Damme, J., Opdenakker, G., Harvey, D. H., Dwek, R. A. and Rudd, P. M. (2000). "The O-glycan analysis of natural human neutrophil gelatinase B using a novel strategy combining normal phase-HPLC and on-line tandem mass spectrometry: implications for the domain organization of the enzyme." *Biochemistry* 39: 15695-704, incorporated herein by reference in its entirety;
2) Royle, L., Mattu, T. S., Hart, E., Langridge, J. I., Merry, A. H., Murphy, N., Harvey, D. J., Dwek, R. A. and Rudd, P. M. (2002). "An analytical and structural database provides a strategy for sequencing O-glycans from microgram quantities of glycoproteins." *Anal Biochem* 304: 70-90, incorporated herein by reference in its entirety;
3) Butler, M., Quelhas, D., Critchley, A. J., Carchon, H., Hebestreit, H. F., Hibbert, R. G., Vilarinho, L., Teles, E., Matthijs, G., Schollen, E., Argibay, P., Harvey, D. J., Dwek, R. A., Jaeken, J. and Rudd, P. M. (2003). "Detailed glycan analysis of serum glycoproteins of patients with congenital disorders of glycosylation indicates the specific defective glycan processing step and provides an insight into pathogenesis." *Glycobiology* 13: 601-22, incorporated herein by reference in its entirety;
4) Peracaula, R., Royle, L., Tabares, G., Mallorqui-Fernandez, G., Barrabes, S., Harvey, D. J., Dwek, R. A., Rudd, P. M. and de Llorens, R. (2003). "Glycosylation of human pancreatic ribonuclease: differences between normal and tumor states." *Glycobiology* 13: 227-44, incorporated herein by reference in its entirety;
5) Peracaula, R., Tabares, G., Royle, L., Harvey, D. J., Dwek, R. A., Rudd, P. M. and de Llorens, R. (2003). "Altered glycosylation pattern allows the distinction between prostate-specific antigen (PSA) from normal and tumor origins." *Glycobiology* 13: 457-70.

One example of a glycan database can be a database comprising glycan structures determined by negative ion mass spectrometry at Oxford Glycobilogy Institute. The use of negative ion mass spectrometry for glycan analysis is described, for example, in 1) D. J. Harvey, Fragmentation of negative ions from carbohydrates: Part 1; Use of nitrate and other anionic adducts for the production of negative ion electrospray spectra from N-linked carbohydrates, *J. Am. Soc. Mass Spectrom.*, 2005, 16, 622-630, incorporated herein by reference in its entirety.
2) D. J. Harvey, Fragmentation of negative ions from carbohydrates: Part 2, Fragmentation of high-mannose N-linked glycans, *J. Am. Soc. Mass Spectrom.*, 2005, 16, 631-646, incorporated herein by reference in its entirety
3) D. J. Harvey, Fragmentation of negative ions from carbohydrates: Part 3, Fragmentation of hybrid and complex N-linked glycans, *J. Am. Soc. Mass Spectrom.*, 2005, 16, 647-659, incorporated, herein by reference in its entirety.

The database currently includes fragmentation patterns of 60 glycan structures from the mass spectrometric profiles of individual oligosaccharides and of mixtures of oligosaccharides. The patterns of this database can be matched to experimental MS profiles by pattern matching using commercially available software.

Another example of a glycan database can be Glycobase, a Web-based glycan database at Oxford Glycobiology Institute (OGBI) illustrated on FIG. 10. Glycobase contains analytical data for over 290 glycan structures and can be used to assign both preliminary and final structures as well as to recommend the appropriate exoglycosidase arrays to confirm preliminary assignments as illustrated in FIG. 10. Panels (a) & (b) of FIG. 10 show the nomenclature that can be used to draw the glycan structures and explain the exoglycosidase digestions. Panel (c) shows some of the structures with GU values listed in the Glycobase; panels (d) to (g) follow the glycan structure A2G2S2 (the abbreviations used are explained in Table 2) thorough a series of digestions with exoglycosidases, in each case the consensus GU value (which is calculated from the experimentally determined GU values listed) is given along with possible digestions and products.

GU values for individual peaks can be generated, for example, using the PeakTime add on software package. The PeakTime software automatically can calculate, for example, the GU value for each sample peak based upon the comparison with dextran ladder standard and can list preliminary assignments to each peak using data from the standard database. Additional software, such as PeakShift or autoGU (a web based algorithm) at OGBI, can be used to assign structures to the products of enzyme digests and confirm which of the initial assignments, made by PeakTime or autoGU, is correct. The Peakshift software uses a combination of peak areas and the incremental values for individual monosaccharide residues.

Figure 11:
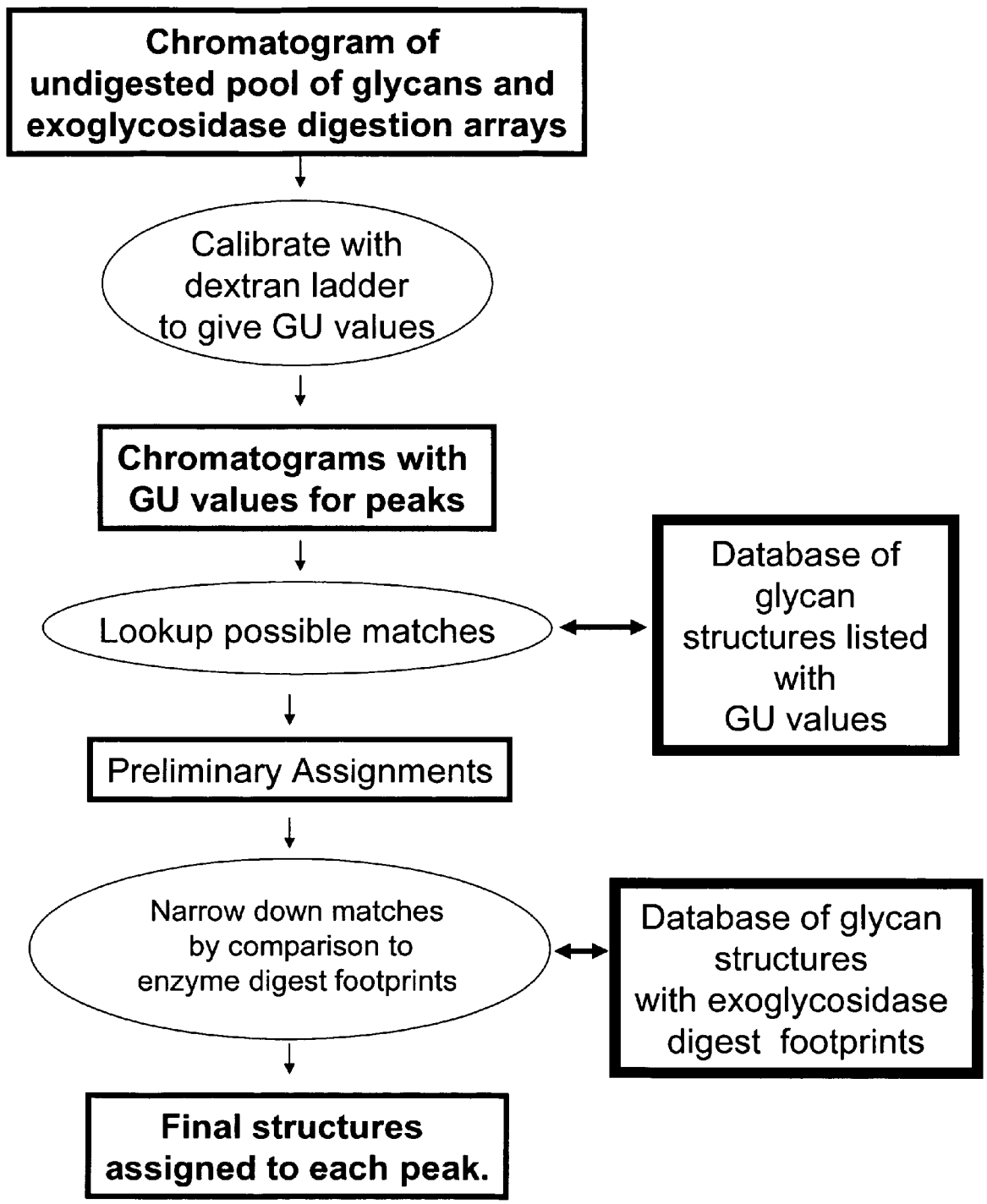
FIG. 11 illustrates an algorithm for assigning glycan structures in glycoprofiles using glycan databases.

An algorithm (FIG. 11) based on a model of generalized transformations on a set of chromatogram peaks with a given variance can be applied for further analyzing glycosylation profiles. In the field of glycobiology, these transformations may represent the action of enzymes, e.g. exoglycosidases; however the generality of the algorithm lends its applicability outside of the field to any area of chemistry or biochemistry in which similar methods are used. The algorithm can be resolved into components. Firstly, each chromatogram can be calibrated on a series of standard peaks using a polynomial curve fitting technique. A first list of possible assignments can be then determined for each peak by table lookup against a database of standard values. A statistically valid procedure can be used in the comparison, employing the known variance of both unknowns and standards. The final step can be a comparison with the stored enzyme digest footprints of the standards.

The database currently in use at OGBI is continually updated as new data are acquired. The database can display the structural abbreviation, schematic diagram, consensus GU value (having calculated an average from the data entered for that structure) and digestion products (which are entered for a range of exoglycosidase digestions). The subsections of the database can be N-links animal; N-links plants; N-links high mannose; O-links core 1&2; O-links core 3&4; O-links other; GSL; and miscellaneous. Further modifications of the database can enable a larger range of subsections to be chosen. The database can potentially allow the user to choose which glycans to view by choices such as: which sugar (e.g. fucose) they contain; or all N-glycan biantennary structures only.

Serum glycome data base. Separate database can be constructed for glycans released for whole serum without purifying the glycoproteins. For example, a specific database can be constructed containing NP-HPLC serum glycan profiles for both sialylated and neutral glycans with currently 38 glycans identified on FIG. 4 and in Table 2.

The following functionality has been completed, fully tested and is currently in use in the laboratory at the Oxford Glycobiology Institute:

1) A database which holds the specificities of enzymes and the standard GU values and variances. The structure of the database is flexible one, allowing different values to be stored for different columns and methods and allowing the store to be divided easily into areas for different chemical groups, or different users or projects.

2) Graphical display. The latest version of PeakTime is able to display multiple plots one above the other to the same scale, and to show the transformations due to enzymes as joins amongst their peaks.

3) The chromatogram may be drawn with the time axis recalculated to the calibrated scale. This allows direct comparisons to be made between multiple plots, especially as values from the database can be displayed as stick-graphs on the same scale.

4) The graphical functions provided include zooming-in, displaying as a stick-graph or the raw curve, switching between peak areas and heights, and annotating with such information as the chemical species name determined from sequencing.

5) Tabular display. Most of what is shown graphically can also be displayed in tabular form. The tables may be adjusted in the width and height of cells, and individual columns may be hidden in a manner that will be familiar to users of spreadsheets.

6) A security system of login names and passwords is provided, allowing the standard data to be protected against unauthorized alteration, and for individual users to restrict access to their private data.

7) A column calibration facility with a polynomial mapping. The range of different calibration types performed includes both the glucose units (GU) and the arabinose units (AU) scales.

8) Operations on chromatograms. A sum and a difference function are provided. Such plots would be hard to interpret without the calibration that PeakTime performs.

9) A rapid data entry mechanism by which experimental data may be added to the database by drag-and-drop with the mouse directly from a chromatogram. This is designed to encourage use of the database for ephemeral day-to-day values, and so to reduce dependence on paper note keeping.

10) Locking. Once calibrated the chromatogram can be locked so that inadvertent alterations may be avoided.

11) Export. Graphics may be exported to files in either bitmap or vector format, or as bitmaps to the windows clipboard. All tables can be exported to files in standard formats for transfer to such tools as Microsoft Access or Excel.

12) Printing. Both graphical and tabular displays can be printed from within PeakTime, and in some cases a print-preview facility is provided. Various display choices are provided, such as fonts, line thicknesses and column widths.

Using the glycosylation markers to identify and isolate glycoproteins. In some embodiments, the determined glycosylation marker of the physiological condition can be used for identifying and isolating one or more glycoprotein biomarkers, i.e. glycoproteins that are specific for the physiological condition. The glycoprotein biomarker of the physiological can carry the glycosylation marker of the condition. The isolation of the glycoprotein biomarker(s) can be carried out using lectins or monoclonal antibodies. For example, lectins were used to isolate gp73, a glycoprotein marker of hepatitis B associated with liver cancer in "Use of targeted glycoproteomics to identify serum glycoproteins that correlate with liver cancer in woodchucks and humans." T. M. Block, M. A. Comunale, M. Lowman, L. F. Steel, P. R. Romano, C. Fimmel, B. C. Tennant, W. T. London, A. A. Evans, B. S. Blumberg, R. A. Dwek, T. S. Mattu and A. S. Mehta (2005) Proc. Natl. Acad. Sci. USA, 102, 779-784.

The invention is further illustrated by, though in no way limited to, the following examples.

EXAMPLE 1

Hepatocellular Carcinoma in Hepatitis C Infected Patients

Figure 4:
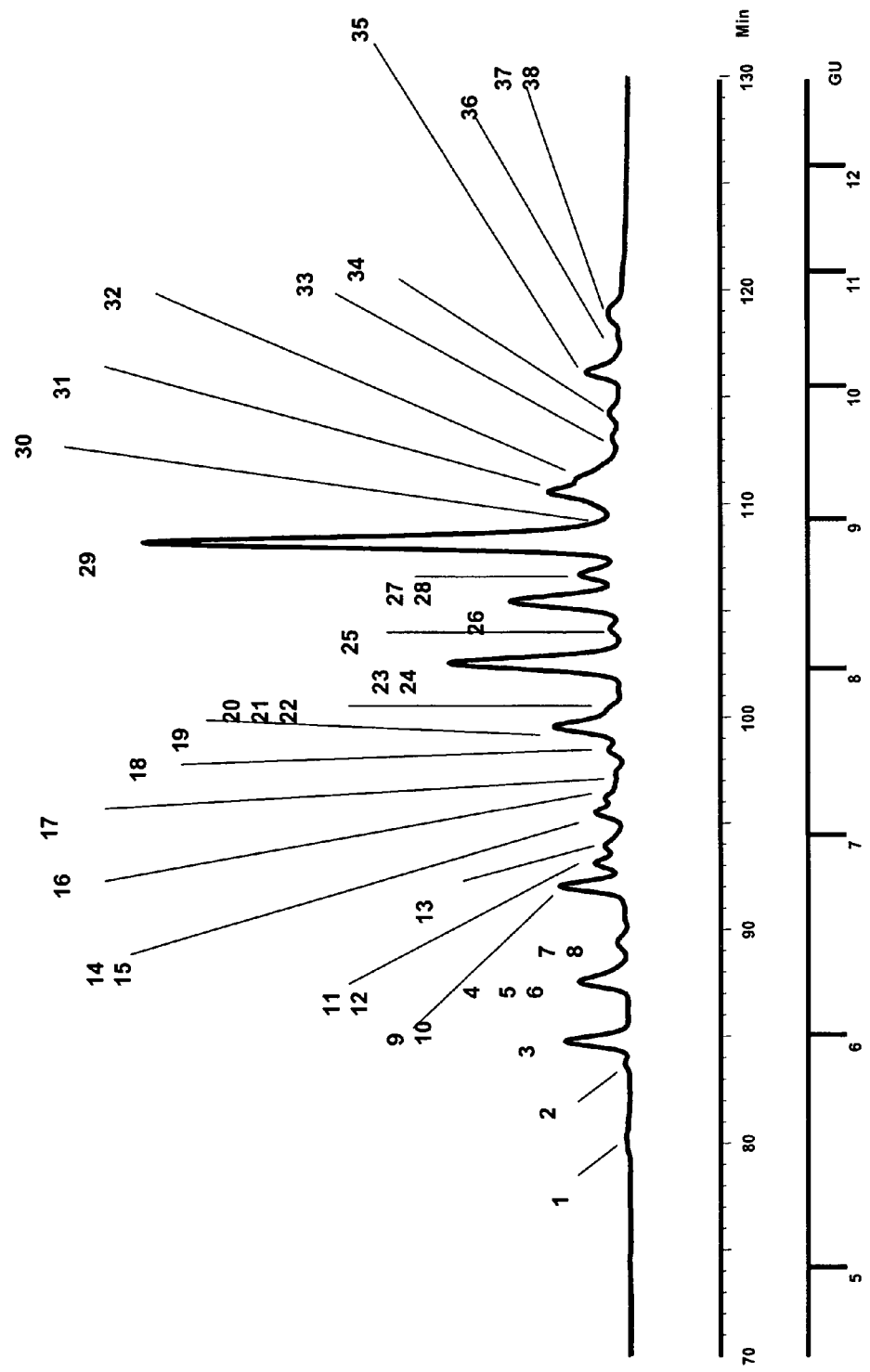
FIG. 4 demonstrates a glycoprofile of 2-AB labeled glycans released from whole serum analysed by NP-HPLC. The glycoprofile is presented as a chromatogram using both elution times and glucose units scales.

Glycosylation profiles of glycans released from whole serum of controls and hepatitis C virus (HCV) infected patients with hepatocellular carcinoma were compared to detect a potential glycosylation marker differentiating the two groups. Healthy control serum samples from two individuals, and one pooled sample were analyzed. A specific database containing NP-HPLC serum glycan profiles for both sialylated and neutral glycans was constructed and identified 38 glycans (FIG. 4, Table 2). The same procedure was applied to patient sera and the glycosylation marker of hepatocellular carcinoma in HCV patients was identified by comparison the database of glycans released from whole serum of HCV infected patients with the database of glycans released from whole serum of healthy controls.

Table 2. N-Glycan structures identified in serum of healthy control. Peak numbers correspond to peak numbers in FIG. 4. Abbreviations used: M5-9: $GlcNAc_2Man_x$, where x is the number of mannoses; Ax: number of antenna, i.e. A2 is biantennary; Gx: number of galactose, [3] and [6] indicate which arm (3 or 6 linked) the galactose is attached to; Sx: the number of sialic acids; B: a bisecting GlcNAc; Fc: α1-6 core fucose. For example, peak 5 with a GU of 6.17 is Man5, this can also be written as $GlcNAc_2Man_5$; peak 33 is Man9 can be also written as $GlcNAc_2Man_9$.

| Peak Number | Structure | GU |
|---|---|---|
| 1 | A2 | 5.47 |
| 2 | A2B | 5.76 |
| 3 | FcA2 | 5.90 |
| 4 | FcA2B | 6.15 |
| 5 | M5 | 6.17 |
| 6 | A2[6]G1 | 6.29 |
| 7 | A2B[6]G1 | 6.46 |
| 8 | A2[3]G1 | 6.48 |
| 9 | FcA2[6]G1 | 6.62 |

-continued

| Peak Number | Structure | GU |
|---|---|---|
| 10 | A2B[3]G1 | 6.63 |
| 11 | FcA2[3]G1 | 6.78 |
| 12 | FcA2B[6]G1 | 6.83 |
| 13 | FcA2B[3]G1 | 6.90 |
| 14 | M6 | 7.06 |
| 15 | A2G2 | 7.13 |
| 16 | A2G1S1 | 7.14 |
| 17 | A2BG2 | 7.25 |
| 18 | A2BG1S1 | 7.47 |
| 19 | FcA2G2 | 7.50 |
| 20 | FcA2BG2 | 7.60 |
| 21 | FcA2BG1S1 | 7.71 |
| 22 | FcA2G1S1 | 7.75 |
| 23 | M7 | 7.93 |
| 24 | A2G2S1 | 8.02 |
| 25 | A2BG2S1 | 8.24 |
| 26 | FcA2G2S1 | 8.42 |
| 27 | FcA2BG2S1 | 8.61 |
| 28 | M8 | 8.77 |
| 29 | A2G2S2 | 8.82 |
| 30 | A2BG2S2 | 8.90 |
| 31 | FcA2G2S2 | 9.18 |
| 32 | FcA2BG2S2 | 9.25 |
| 33 | M9 | 9.50 |
| 34 | A3G3S2 | 9.78 |
| 35 | A3G3S3 | 10.11 |
| 36 | A3BG3S3 | 10.43 |
| 37 | FcA3G3S3 | 10.60 |
| 38 | FcA3BG3S3 | 10.65 |

Samples of serum from HCV infected patients with hepatocellular carcinoma were obtained from HCV infected patients with moderate or severe fibrosis/cirrhosis. Samples of healthy control serum were obtained as discarded clinical material from individuals undergoing routine health screening.

Glycoproteins in reduced and denatured serum samples were attached to a hydrophobic PVDF membrane in a 96 well plate (Multiscreen_IP, 0.45 µm hydrophobic, high polyvinyldene fluoride (PVDF) membranes, Millipore, Bedford, Mass., USA) by simple filtration. The samples were then washed to remove contaminates, incubated with PNGaseF to release the glycans based on the methods described in Papac, D. I., et. al. *Glycobiology* 8: 445-54, 1998, and in Callewaert, N., et. al. *Electrophoresis* 25: 3128-31, 2004, both incorporated herein by reference in their entirety. The N-glycans were then washed from the bound protein, collected and dried down ready for fluorescent labeling.

Released glycans were labeled with 2-aminobenzamide (2-AB) fluorescent label with or without a commercial kit (from e.g. Ludger Ltd, Oxford, UK) as described in Bigge, J. C., Patel, T. P., Bruce, J. A., Goulding, P. N., Charles, S. M, and Parekh, R. B. (1995). *Nonselective and efficient fluorescent labeling of glycans using 2-amino benzamide and anthranilic acid. Analytical Biochemistry* 230: 229-238, incorporated herein by reference in its entirety, and run by normal phase high performance liquid chromatography (NP-HPLC) on a 4.6×250 mm TSK Amide-80 column (Anachem, Luton, UK) using a Waters 2695 separations module equipped with a Waters 2475 fluorescence detector (Waters, Milford, Mass., USA) as described in Guile, G. R., Rudd, P. M., Wing, D. R., Prime, S. B., and Dwek, R. A. (1996). *A rapid high-resolution high-performance liquid chromatographic method for separating glycan mixtures and analyzing oligosaccharide profiles. Analytical Biochemistry* 240: 210-226, incorporated herein by reference in its entirety. Prior to NP-HPLC analysis, glycans were sequentially digested with a series of exoglycosidases.

FIG. 5 presents NP-HPLC profiles of glycans released from control sample Con_9 and from sample of HCV infected patient with hepatocellular carcinoma HCV_42. On FIG. 5, panel (A) corresponds to glycoprofiles of whole serum glycans not exposed to any exoglycosidase digestion, panel (B) to glycoprofiles following digestion with an array of α2-3,6,8-sialidase, β1-4 galactosidase and β-N-acetylglucosaminidase. Panel (C) of FIG. 5 demonstrates that the marker correlated with the diagnosis of hepatocellular carcinoma in HCV patients is the percentage of core fucosylated glycans measured after digestion with α2-3,6,8-sialidase, β1-4 galactosidase and β-N-acetylglucosaminidase. Healthy control sera contains between 15 and 17% of these glycans, while sera of HCV infected patients with hepatocellular carcinoma contained more than 19% of these glycans. The correlation was also observed between the stage of the disease and the percentage of core fucosylated glycans measured after digestion with α2-3,6,8-sialidase, β1-4 galactosidase and β-N-acetylglucosaminidase. HCV infected patients in moderate stage of hepatocellular carcinoma had the percentage of core fucosylated glycans of 20-22% measured after digestion with α2-3,6,8-sialidase, β1-4 galactosidase and β-N-acetylglucosaminidase while patients in severe stages of disease, such as severe fibrosis/cirrhosis, had this glycan marker above 25% on average.

Conclusion: a glycosylation marker of hepatocellular carcinoma in HCV patients was identified by comparing glycosylation profiles of glycans released from whole serum of HCV patients with hepatocellular carcinoma and of glycans released from whole serum of healthy controls. The glycosylation marker of hepatocellular carcinoma in HCV patients is the percentage of core fucosylated glycans measured after digestion with α2-3,6,8-sialidase, β1-4 galactosidase and β-N-acetylglucosaminidase. The marker correlates with the disease diagnosis and the disease severity. Digestion of glycans with exoglycosidases amplifies/segregates the glycosylation marker of hepatocellular carcinoma in HCV patients.

EXAMPLE 2

Rheumatoid Arthritis

The measurement of the G0/triple-G1 ratio directly from undigested glycans released from whole serum was compared with the 'classic' measurement of the amount of G0 glycans as a percentage of the total glycans released from purified IgG after sialidase and fucosidase digestion. It has been established that G0 released from purified IgG is a disease (RA) specific marker that correlates with disease progression and that can be used as a prognostic indicator of the disease, see e.g. U.S. Pat. No. 4,659,659 "Diagnostic Method for Diseases Having an Arthritic Component" to Dwek et. al. issued on Apr. 21, 1987; Parekh et al., see "*Association of Rheumatoid Arthritis and Primary Osteoarthritis with Changes in the Glycosylation Pattern of Total Serum IgG*," Nature, 316, pp. 452-457, 1985; and Parekh. et. al. "*Galactosylation of IgG Associated Oligosaccharides Is Reduced in Patients with Adult and Juvenile Onset Rheumatoid Arthritis and Is Related to Disease Activity*," Lancet, No. 8592, vol. 1, pp. 966-969, 1988. This study is used to demonstrate that a direct measurement of glycans released from whole serum can be used as marker for rheumatoid arthritis without IgG purification by correlating G0/triple-G1 ratio from undigested glycans released from whole serum with the amount of G0 glycans as a percentage of the total glycans released from purified IgG.

Selection of patient sample. Control patient serum was pooled discarded clinical material from individuals undergoing routine employee health screening. RA patients were selected based on a combination of physician global activity score, rheumatoid factor seropositivity and active joint count.

IgG purification: IgG was isolated from whole serum via affinity chromatography employing protein-G sepharose as described in "*Antibodies: A laboratory manual*," Cold Spring Harbor Laboratory, Cold Spring Harbor, 1988, and P. L. Ey et. al. "*Isolation of pure $IgG_1$, $IgG_{2a}$ and $IgG_{2b}$ immunoglobulins from mouse serum using protein A-Sepharose*," Molecular Immunology, vol. 15, pp. 429, 1978, both incorporated herein by reference in their entirety. Briefly, 100 µl of whole serum was diluted with 300 µl of 100 mM Tris pH 8.0 and allowed to pass over a 1 ml column of protein-G sepharose beads (Amersham Biosciences). Bound material was washed with 15 column volumes of 100 mM Tris pH 8.0. IgG was eluted using 100 mM glycine pH 2.6 buffer directly into 1/10 volume 1M Tris pH 8.0 and collected in 1 ml fractions. Protein content of eluted fractions was determined by 280 nM (UV) absorbance (Beckman Coulter Model DU640 spectrophotometer). Protein containing eluted fractions were pooled and dialyzed into phosphate buffered saline. IgG presence in eluted fractions was confirmed via 10% polyacryl amide gel electrophoresis (PAGE) under reducing conditions (as described, e.g., in Laemmli, "*Cleavage of structural proteins during the assembly of the head of bacteriophage T4*," Nature: 227, 680-685, 1970, incorporated herein by reference in its entirety) and via western blot (*Current Protocols in Immunology*. John Wiley and Sons, 1994, incorporated herein by reference in its entirety) utilizing horseradish-peroxidase conjugated donkey-anti-human IgG (Jackson Immunochemicals) and visualized with Western Lightning Chemiluminescence Reagent Plus (Perkin Elmer). Quantitative depletion of serum IgG in column flow through material was confirmed via western blot analysis.

Glycans release: Glycans were released from purified IgG by running the reduced and alkylated sample on sodium-dodecyl sulphate polyacryl amide gel electrophoresis (SDS-PAGE), cutting out the heavy chain and digesting with peptide N-glycosidase F (PNGaseF) as described in Küster, B., Wheeler, S. F., Hunter, A. P., Dwek, R. A., and Harvey, D. J. (1997). *Sequencing of N-linked oligosaccharides directly from protein gels: in-gel deglycosylation followed by matrix-assisted laser desorption/ionization mass spectrometry and normal-phase high-performance liquid chromatography. Analytical Biochemistry* 250: 82-101, incorporated herein by reference in its entirety. Glycans were released with PNGaseF from 5 µl of whole sera after binding the reduced and alkylated serum to MultiScreen_IP, 0.45 µm hydrophobic, high protein binding polyvinylidene fluoride (PVDF) membranes in a 96 well plate format (Millipore, Bedford, Mass., USA). Released glycans were labeled with 2AB fluorescent label (Ludger Ltd, Oxford, UK) as described in Bigge, J. C., Patel, T. P., Bruce, J. A., Goulding, P. N., Charles, S. M., and Parekh, R. B. (1995). *Nonselective and efficient fluorescent labeling of glycans using 2-amino benzamide and anthranilic acid. Analytical Biochemistry* 230: 229-238, incorporated herein by reference in its entirety, and run by normal phase high performance liquid chromatography (NP-HPLC) on a 4.6× 250 mm TSK Amide-80 column (Anachem, Luton, UK) using a Waters 2695 separations module equipped with a Waters 2475 fluorescence detector (Waters, Milford, Mass., USA) as described in Guile, G. R., Rudd, P. M, Wing, D. R., Prime, S. B., and Dwek, R. A. (1996). *A rapid high-resolution high-performance liquid chromatographic method for separating glycan mixtures and analyzing oligosaccharide profiles. Analytical Biochemistry* 240: 210-226. Purified, 2AB labeled IgG heavy chain glycans were also digested with sialidase and fucosidase to reduce all the structures to G0, G1 or G2 +/− bisect, then run on NP-HPLC. [G0 denotes no galactose; G1, one galactose; and, G2 two galactose, all on biantennary complex N-glycans.]

Figure 6:
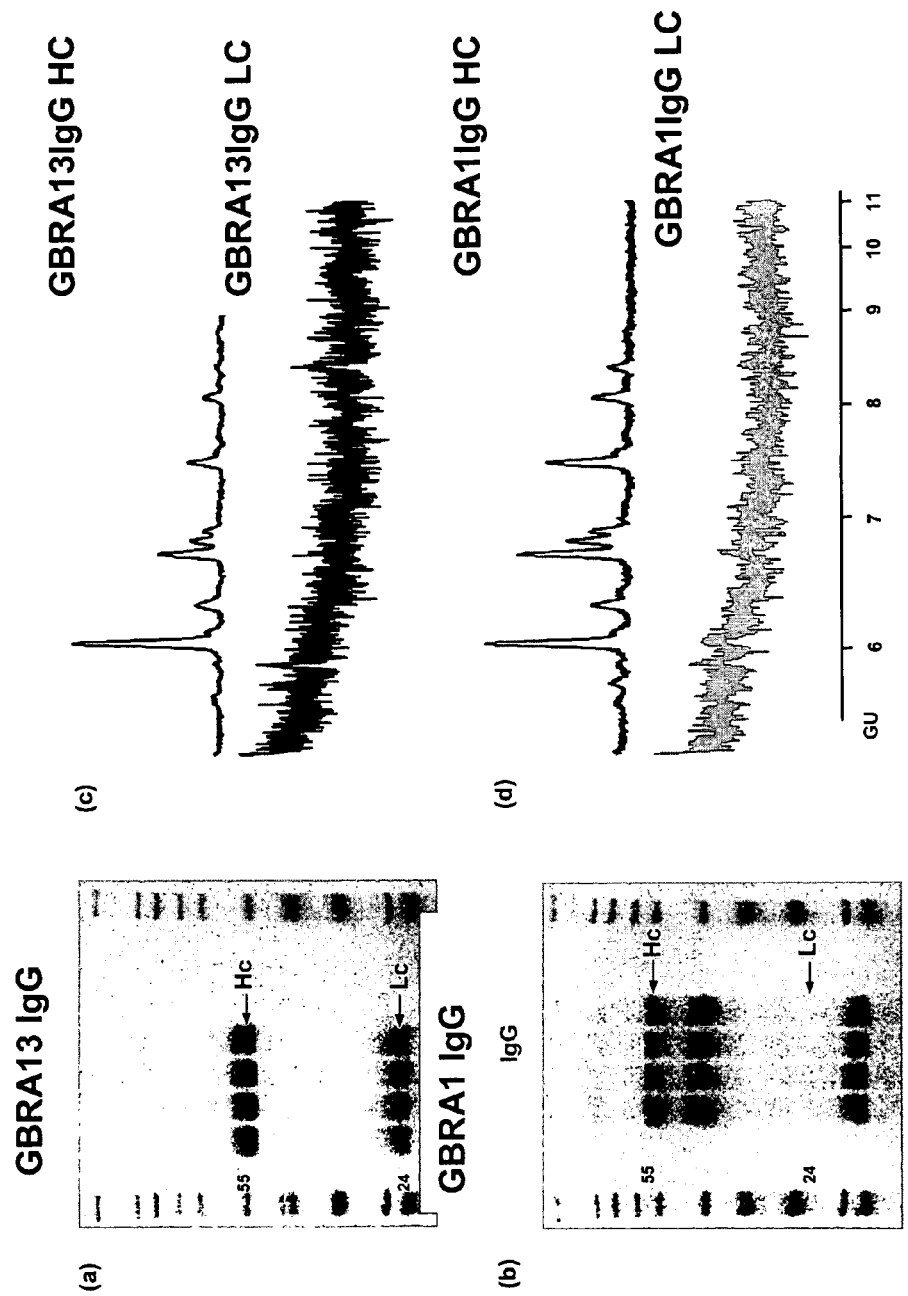
FIG. 6 shows sodium dodecyl sulphate polyacrylamide gel electrophoresis (SDS-PAGE) and NP-HPLC profiles of glycans released from purified immunoglobulin G (IgG) of samples GBRA1 and GBRA13.
Figure 9:
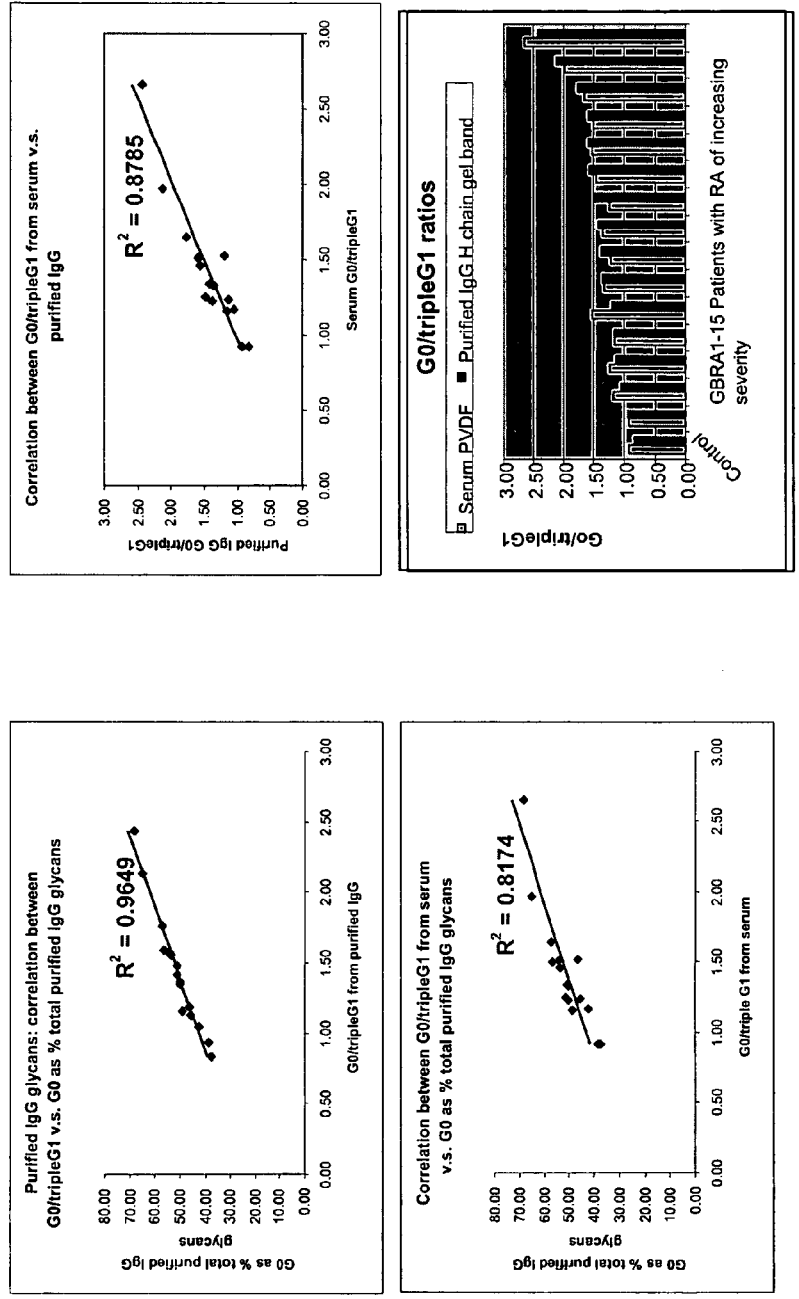
FIG. 9 shows the correlation between a glycosylation marker of rheumatoid arthritis determined in glycans released from total serum (G0/triple-G1 ratio) and the established rheumatoid arthritis diagnostic (determined as a percentage of G0 glycans in the total glycans released from purified IgG).
Figure 10A:
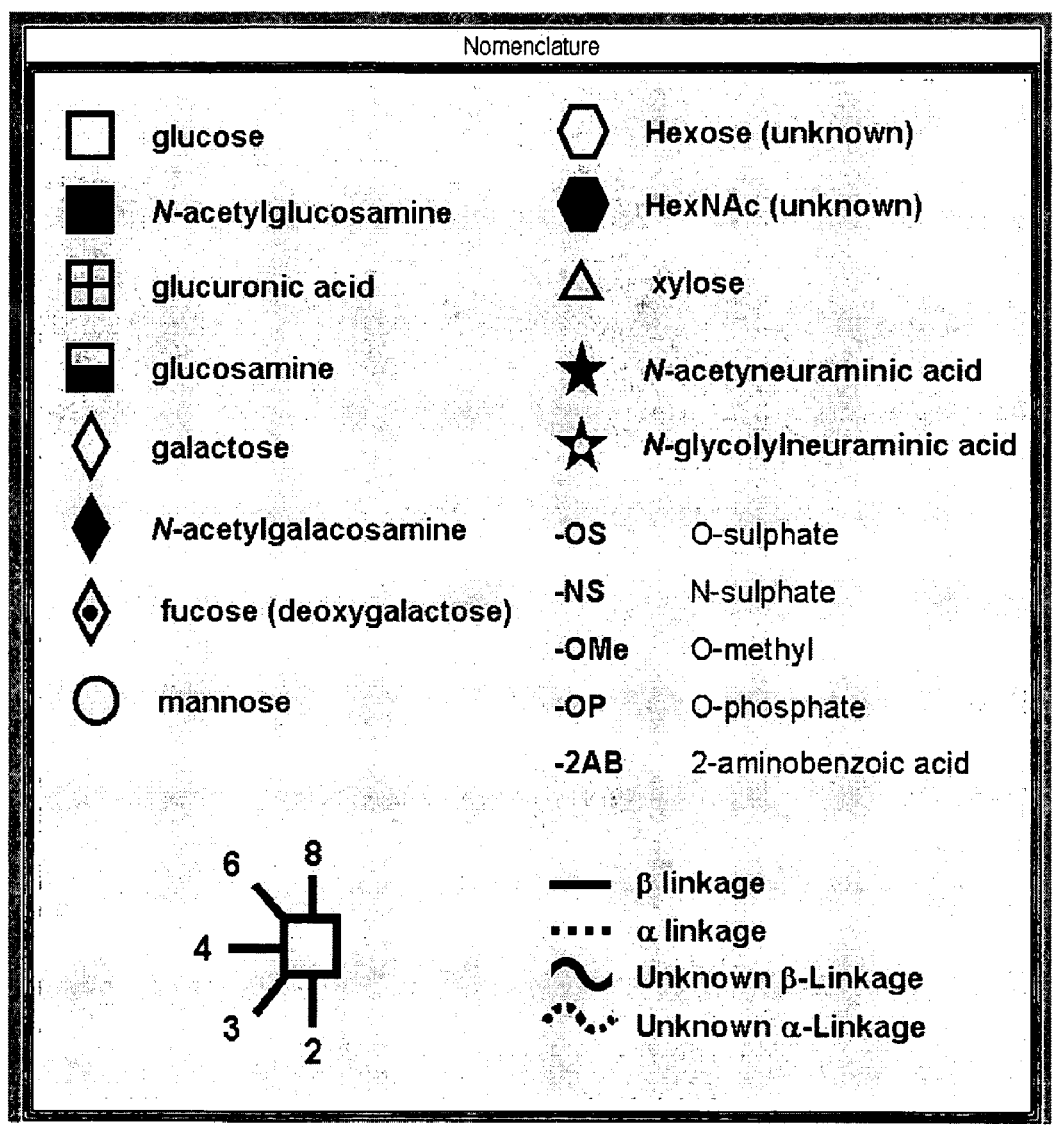
Figure 10B:
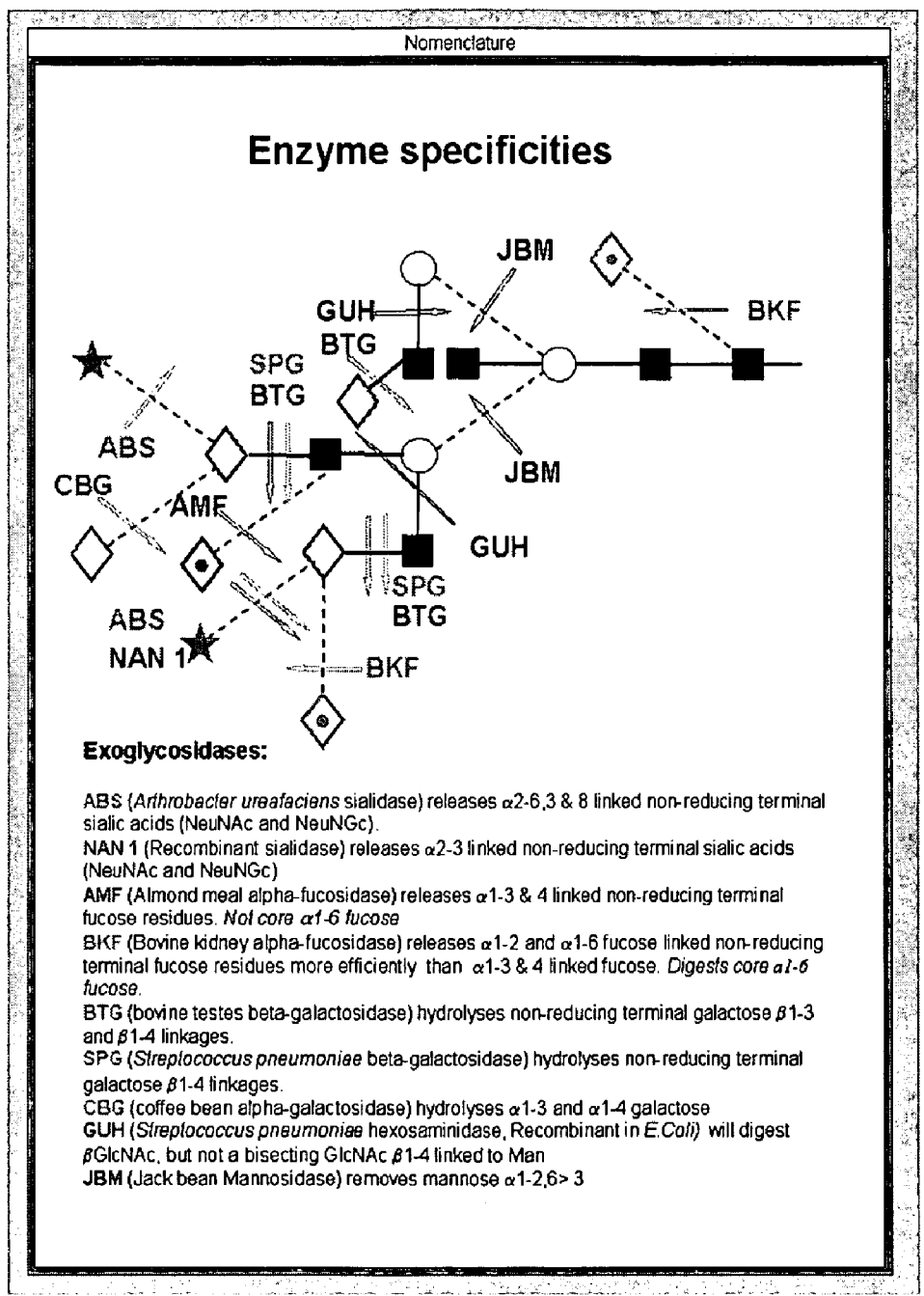
Figure 10F:
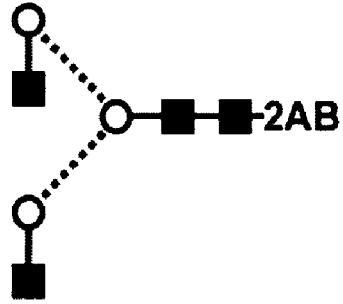
Figure 10G:
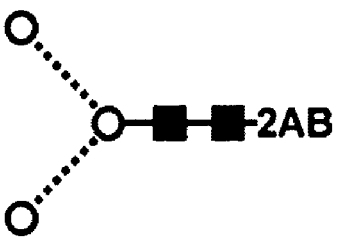

Statistical analysis. All the data for glycan ratios are listed in Table 3. Left top, left bottom, right top panels of FIG. 9 are plots showing correlations between these data. The $R^2$ values were obtained by linear regression analysis using Microsoft Excel. Experimental results. FIG. 6 shows SDS-PAGE and NP-HPLC profiles from samples GBRA13 and GBRA1. In particular, insets (a) and (b) of FIG. 6 provide SDS-PAGE gel pictures of the purified IgGs from the respective samples separated into heavy (H) and light (L) chain bands. Insets (c) and (d) of FIG. 6 provide NP-HPLC profiles for heavy and light chain glycans released from the gel bands shown in (a) and (b) and not subjected to digestion with sialidase and fucosidase. Since no glycans were detected on the light chain, only the heavy chain was required for analysis.

Figure 7:
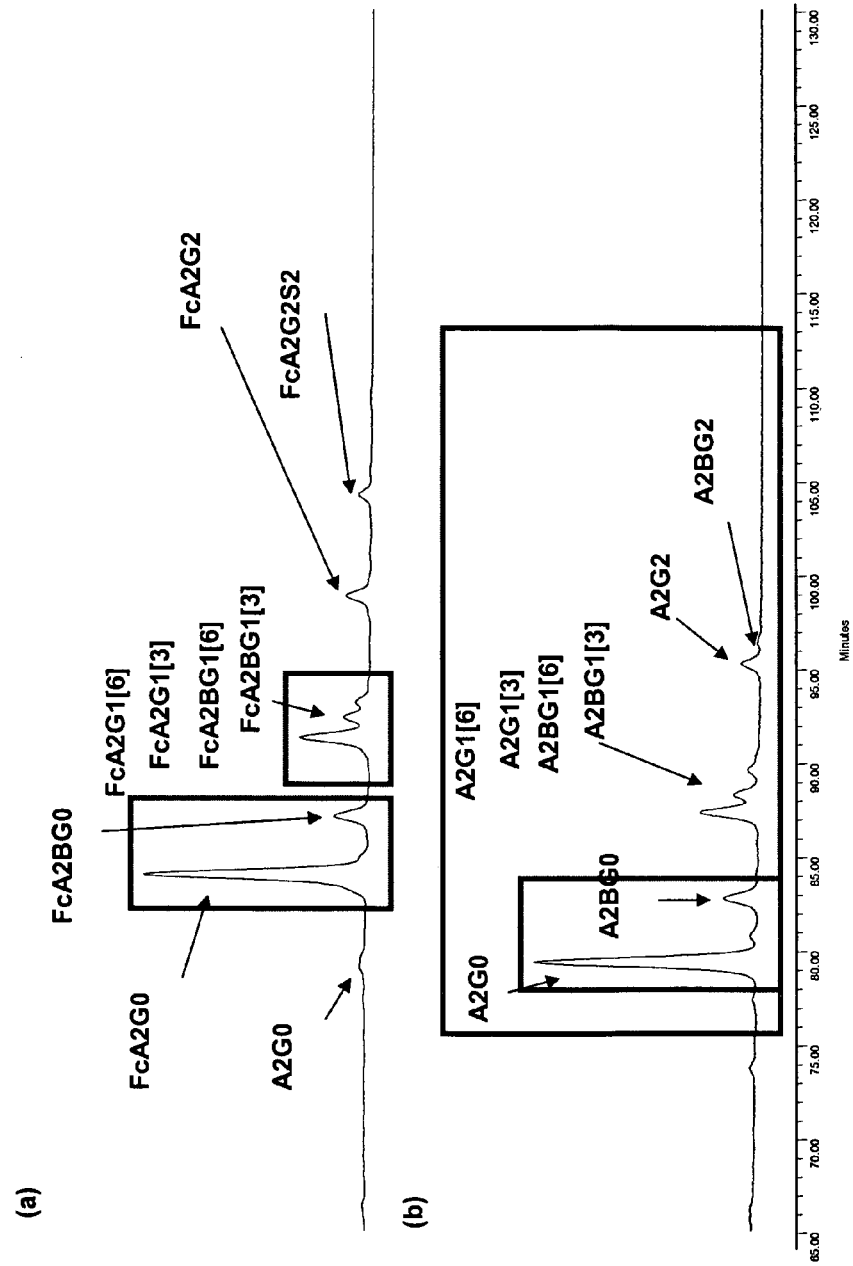
FIG. 7 shows NP-HPLC profiles of glycans released from purified IgG of sample GBRA15.

FIG. 7 illustrates the details of (a) the measurement of the G0/triple-G1 ratio directly from undigested glycans released from purified IgG and (b) the 'classic' measurement of the ratio G0 glycans to the total released from purified IgG and digested with sialidase and fucosidase. In particular, FIG. 7 shows NP-HPLC profiles from the sample GBRA15. Each peak corresponds to certain glycan(s). The peaks in each profile are integrated to give the area under the curve for each peak. In the measurement of the G0/triple-G1 ratio, the area under the peaks corresponding to the G0 glycans (left box of the inset (a) of FIG. 7) are divided by the area under the triplet of peaks corresponding to the G1 glycans (right box of the inset (a) of FIG. 7). As the vast majority of glycans found in these experiments were core fucosylated, only core fucosylated glycans were included in these measurements, i.e. the ratio G0/triple-G1 is actually the peak area of FcA2G0 divided by the peak area of FcA2G1[6]+FcA2G1[3]+FcA2BG1[6]+FcA2BG1[3] (which elutes as a triplet). In the 'classic' measurement, the area under the peaks corresponding to the G0 peaks is divided by the total area under all the peaks in the profile and expressed as a percentage.

Figure 8:
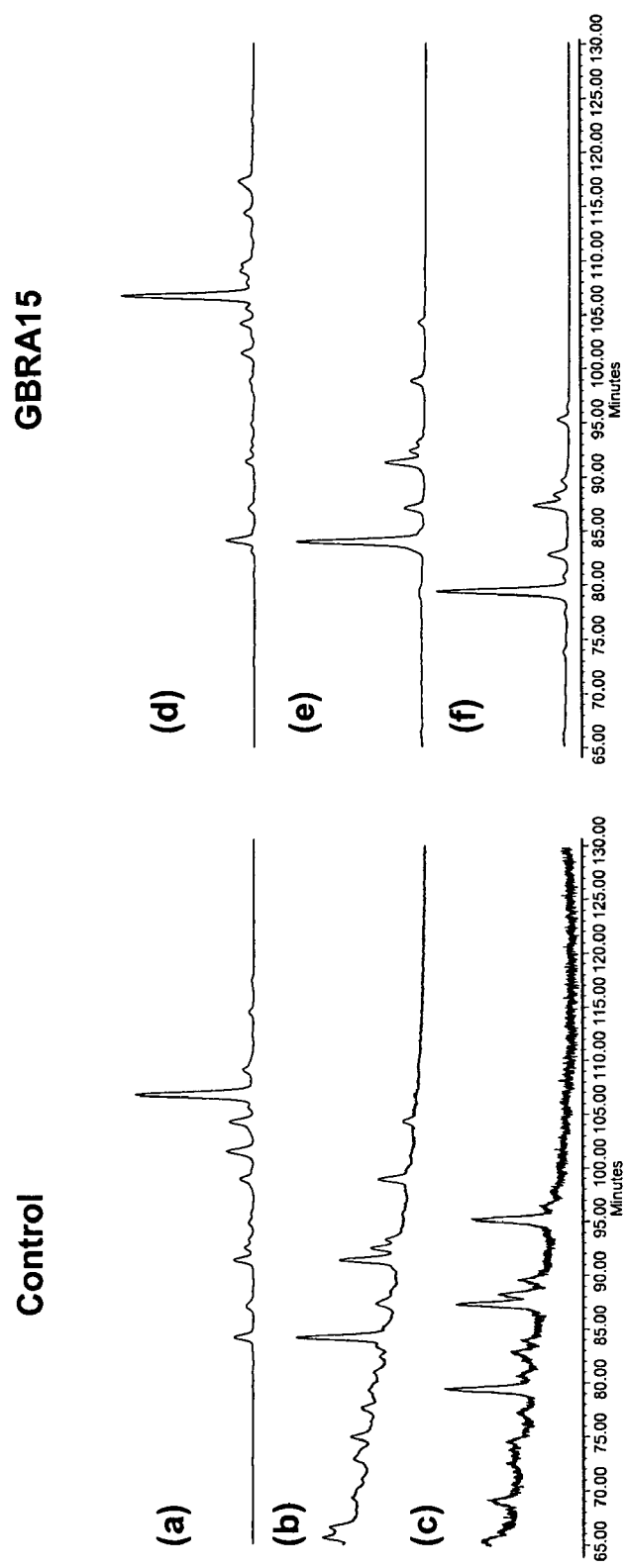
FIG. 8 shows NP-HPLC profiles of control and sample GBRA15.

FIG. 8 illustrates NP-HPLC profiles of control sample and the sample GBRA15. Particularly, insets (a) and (d) show glycans released from whole sera of the respective samples, insets (b) and (e) show undigested heavy chain glycans released from respective purified IgGs, insets (c) and (f) show heavy chain glycans released from respective purified IgGs and digested with sialidase and fucosidase.

Table 3 lists the ratios of the G0 to triple-G1 peak from whole serum and purified IgG from the same serum samples from 15 RA patients and one pooled control. The 'classic' measurement of the amount of G0 glycans as a percentage of the total glycans (G0+G1+G2) from purified IgG is also shown. Comparing the results of the two different measurements taken from purified IgG, a high correlation ($R^2$=0.9649) is found, indicating that the ratio G0/triple-G1 is as a good measurement as the 'classic' measurement of the percentage of G0 glycans in total glycan pool (FIG. 9, left top panel). Comparing the G0/triple-G1 ratio between purified IgG and whole serum glycans gives a correlation of $R^2$=0.8785 (FIG. 9, right top panel), whilst comparing the G0/triple-G1 ratio from whole serum glycans with the percentage G0 glycans from purified IgG gives a correlation of $R^2$=0.8174 (FIG. 9, left bottom panel). FIG. 9, right bottom panel, is a histogram showing the G0/triple-G1 ratios for all serum and IgG samples.

TABLE 3

| Patient i.d. | undigested G0/triple-G1 | | G0 as % of TOTAL digested IgG glycans |
|---|---|---|---|
| | Glycans released from Serum using PVDF | Glycans released from purified IgG using SDS-PAGE | |
| Control | 0.92 | 0.84 | 37.40 |
| GBRA1 | 0.92 | 0.94 | 38.43 |
| GBRA2 | 1.17 | 1.05 | 42.26 |
| GBRA3 | 1.24 | 1.13 | 45.43 |
| GBRA4 | 1.16 | 1.16 | 48.74 |
| GBRA5 | 1.53 | 1.19 | 46.26 |
| GBRA6 | 1.33 | 1.35 | 49.94 |
| GBRA7 | 1.23 | 1.37 | 50.18 |
| GBRA8 | 1.34 | 1.42 | 50.74 |
| GBRA9 | 1.25 | 1.48 | 51.14 |
| GBRA10 | 1.46 | 1.56 | 53.50 |
| GBRA11 | 1.52 | 1.58 | 54.13 |
| GBRA12 | 1.51 | 1.59 | 56.59 |
| GBRA13 | 1.65 | 1.76 | 56.98 |
| GBRA14 | 1.97 | 2.13 | 65.16 |
| GBRA15 | 2.66 | 2.44 | 68.28 |

Conclusion. The use of the high throughput PVDF membrane 96 well plate format with only 5 µl of whole serum being used to obtain glycans for a direct measurement of the G0/triple-G1 ratio has been demonstrated. This procedure replaces the more lengthy procedure of measuring the percentage of G0 glycans in the glycans released from purified IgG determined after exoglycosidase treatment, as an indicator of RA disease state. Thus, to monitor the RA disease state, one can efficiently reduce working hours from sample preparation to results by using the PVDF membrane method with whole serum as well as reducing the amount of material (serum) used.

Measuring Glycan Profiles from Individual or Pooled Protein Spots from 2D-PAGE Inventors also realized that glycoproteins in serum or other body fluid or body tissue from a subject of the disease, such as human or mammal, can contain mixtures of discrete glycoforms that originate from normal cells as well as those altered directly as a result of the disease or are secreted in response to pathogenesis. Using 2D-PAGE gels to separate subsets of glycoforms at the protein level one can identify the disease related spots by their altered glycosylation. The sensitivity of the disease markers can increase as only the disease altered forms are analyzed. This provides the way to determining glycosylation related disease makers and to monitoring their changes with, for example, disease progression or remission or medication.

Accordingly, the present invention provides a method of identifying one or more biomarkers of disease, said method comprising separating a protein pool from a body fluid or a body tissue of a subject of the disease using 2 dimensional electrophoresis into individual spots or trains of spots, each of the individual spots or the spots from the trains comprises one or more proteins of the protein pool; measuring detailed glycoprofiles of glycan pools released from the individual spots or single or pooled spots from a train and identifying out of the measured spots one or more disease associated spots as the one or more biomarkers of disease, where the disease associated spots have altered glycosylation profiles. In some embodiments, the identification of one or more biomarkers can include comparing the glycosylation profiles among the train of spots corresponding to one glycoprotein. In some embodiments, said identifying can comprise identifying one or more proteins that are unique for the disease. The protein pool can comprise all or substantially all of the proteins present in the sample of a body fluid or a body tissue. In some embodiments, substantially all of the proteins can mean all the proteins that are recovered, yet in some embodiments substantially all of the proteins can mean all the proteins except those that are specifically removed. 2 dimensional electrophoresis can be 2 dimensional polyacrylamide gel electrophoresis as described, for example, in Görg, A., and Weiss, W, Methods Mol. Biol, 112, 235-244, 1999 or in Görg, A., Weiss, W., Dunn, M. J., Proteomics, 4, 3665-3685, 2004, both incorporated herein by reference in their entirety. Measuring glycoprofiles can be carried out using chromatographic or other methods described above. Glycans in the glycan pools can be labeled with a fluorescent label such as 2-AB. The N-glycan pool can be released from the individual or pooled spots in the train using PNGase F or other enzymatic or chemical release method discussed above. The method can be directed to identifying disease biomarkers (diseased associated spots) for diseases associated with glycosylation alterations such as rheumatoid arthritis or other autoimmune disease, cancer or congenital disorder of glycosylation. Glycosylation alterations in rheumatoid arthritis patients are disclosed, for example, in U.S. provisional patent application No. 60/674,722 filed Apr. 26, 2005, incorporated herein by reference in its entirety. Glycosylation alteration in cancer patients are disclosed, for example, in U.S. provisional patent application No. 60/674,723 filed Apr. 26, 2005, incorporated herein by reference. In some embodiments, measured spots can correspond to highly abundant glycoproteins such as IgG. In some embodiments, measured spots can correspond to glycoproteins other than IgG. For example, glycoprofiles can be measured from the low abundant spots with quantities of glycoprotein less than about 100 ng, more preferably less than about 10 ng, more preferably less than about 5 ng, more preferably less than about 2 ng, most preferably less than about 1 ng.

The following example illustrates measuring glycoprofiles from individual or pooled spots from a 2D-PAGE gel. However, it should be understood that the present invention is not limited thereto.

EXAMPLE 3

Measuring Glycosylation Profiles from 2D-PAGE Gel Spot(s)

2D-PAGE method. 2D-PAGE was performed essentially as described by Görg, A., and Weiss, W. (1999, Horizontal SDS-PAGE for IPG-Dalt. Methods Mol Biol 112: 235-244), incorporated herein by reference in its entirety. Sample preparation, electrophoresis, staining, scanning and spot excision were carried out in category I; class 100,000 Clean Room conditions. Dry strip cover mineral oil, Immobiline® IPG DryStrips, electrode wicks and the electrophoresis equipment for running the first dimension (reswelling tray, Multiphor II, EPS 3500XL power supply) were all from GE Healthcare (Buckinghamshire, UK). The second dimension running tanks, staining tanks, OGT 1238 fluorescent dye, Apollo linear fluorescence scanner and LIMS system were provided by Oxford GlycoSciences (Abingdon, UK). Melanie II image analysis software (release 2.3) was from Bio-Rad/The Melanie Group (Geneva, Switzerland) but was customized by Oxford GlycoSciences. All chemicals were of the highest purity.

First Dimension: Immobilised pH Gradient-Isoelectric focusing. A healthy control human serum sample was used in this experiment. The protein concentration was determined using the Bicinchoninic acid (BCA) assay method of Smith et. al (Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985). Measurement of protein using bicinchoninic acid. Anal Biochem 150: 76-85) as 72.5 mg/ml. A 500 µg (6.9 µl) aliquot was used.

The sample in 375 µl of 5 M urea, 2 M thiourea, 4% (w/v) 3-[(3-cholamidopropyl)dimethylammonio]-1-propanesulfonate (CHAPS), 65 mM dithiothreitol (DTT), 2 mM tributyl phosphine (TBP), 150 mM NDSB-256 (dimethylbenzylammonium propane sulfonate, non-detergent sulfobetaine-256-NDSB-256, Merck Biosciences Nottingham, UK) and 0.002% (w/v) bromophenol blue was vortex mixed with 0.45% (v/v) of pH 2-4 carrier ampholytes (SERVALYT® SERVA, Heidelberg, Germany), 0.45% (v/v) of pH 9-11 carrier ampholytes and 0.9% (v/v) of pH 3-10 carrier ampholytes and then left at room temperature for 1 hr to ensure complete denaturation and solubilisation, then spun at 16,000 g for 15 min. The supernatant was carefully pipetted into a lane in a reswelling tray. A 3 mm wide, pH 3-10 NL, 18 cm Immobiline® IPG DryStrip was placed face down onto the sample and overlaid with 2 ml of dry strip cover mineral oil. Rehydration was performed for 20 hrs at room temperature.

After rehydration, the strip was briefly drained of excess mineral oil and transferred to the Multiphor II with the gel facing upwards. Electrode wicks 2 cm in length were soaked with 100 µl of water and blotted to ensure that they were damp but not excessively wet. These damp wicks were placed on either end of the IPG strip. Electrode bars were fixed onto the wicks at either end of the IPG strip and mineral oil was poured into the sample tray until the strip was immersed. IEF was carried out at 300 V for 2 h and then 3500 V up to 75 kVh according to Sanchez et al (Sanchez, J. C., Rouge, V., Pisteur, M., Ravier, F., Tonella, L., Moosmayer, M., Wilkins, M. R., and Hochstrasser, D. F. (1997), incorporated herein by reference in its entirety. Improved and simplified in-gel sample application using reswelling of dry immobilized pH gradients). Electrophoresis 18: 324-327 using an EPS 3500XL power supply. The temperature was maintained at 17° C. using a recycling thermostatic water bath.

Second Dimension: SDS-PAGE. Immediately post IEF, the IPG strip was incubated in reducing equilibration solution (4 M urea, 2 M thiourea, 50 mM 2-Amino-2-(hydroxymethyl)-1,3-propanediol (Tris) HCl pH 6.8, 30% (v/v) glycerol, 2% (w/v) SDS, 130 mM DTT, 0.002% (w/v) bromophenol blue) for 15 min at 20° C. The strip was drained of equilibration solution and overlaid onto a 1 mm thick, 20 cm×18 cm, 9-16% T, 2.67% C gradient gel and sealed in place with 90° C., 0.5% (w/v) agarose in 25 mM Tris, 192 mM glycine, 0.1% (w/v) SDS (reservoir buffer). Once the agarose had set, second dimension electrophoresis was carried out.

The reservoir buffer (Laemmli, U. K. (1970). Cleavage of structural proteins during the assembly of the head of bacteriophage T4. Nature 227: 680-685) was used. Electrophoresis was carried out in an electrophoresis tank similar to that described by Amess and Tolkovsky (Amess, B., and Tolkovsky, A. M. (1995). Programmed cell death in sympathetic neurons: a study by two-dimensional polyacrylamide gel electrophoresis using computer image analysis. Electrophoresis 16: 1255-1267). The current was set at 20 mA per gel for 1 h, followed by 40 mA per gel for 4 h. The temperature was maintained at 10° C. using a recycling thermostatic water bath. Electrophoresis was terminated once the bromophenol blue tracking dye had reached the bottom of the gel.

Staining and Image analysis. Prior to fixing, the gels were briefly washed in water to remove running buffer. The proteins on the gels were fixed in 40% (v/v) ethanol, 10% (v/v) acetic acid overnight. The fluorescent dye OGT 1238 was used to stain the gels. The 2D-PAGE gels were imaged (16-bit monochrome fluorescent images, 200 µm resolution) with a 488 nm Apollo linear fluorescence scanner. Then analyzed with a custom version of Melanie II.

Glycan Release from Gel spots. Previously identified glycoproteins, $\alpha 2$ macroglobulin, $\alpha 2$ acid glycoprotein, $\alpha 1$ acid glycoprotein, IgG heavy chain and haptoglobin $\beta$ chain, plus haptoglobin $\alpha 2$ which is known not to be glycosylated and a gel blank were highlighted on the Melanie II software and excised manually using a Dark Reader transilluminator and placed into individual 1.5 ml tubes. The gels were frozen overnight.

The gel pieces were washed with 1 ml of 20 mM sodium bicarbonate ($NaHCO_3$) for 20 min followed by 1 ml of acetonitrile for 10 min. Proteins were reduced by adding 100 µl of 10 mM DTT in 20 mM $NaHCO_3$ and incubating for 10 min at 70° C. The DTT solution was removed and free thiols were alkylated by adding 100 µl of 50 mM iodoacetamide in 20 mM $NaHCO_3$ and incubating in the dark for 30 min. The gel pieces were then washed alternatively with 1 ml of acetonitrile then 1 ml of 20 mM $NaHCO_3$ pH 7, which was repeated twice, then the gel was dried. PNGaseF buffer solution (60 µl of 100 U/ml) was added and incubated overnight at 37° C. The supernatant was recovered along with 3×200 µl water washes (with sonification for 30 mins) followed by an acetonitrile wash, another water wash and a final acetonitrile wash. Samples were filtered through a 0.45 µm LH Millipore filter and dried down for fluorescent labelling. Samples were labeled with 2AB and analyzed by normal phase HPLC.

Figure 12:
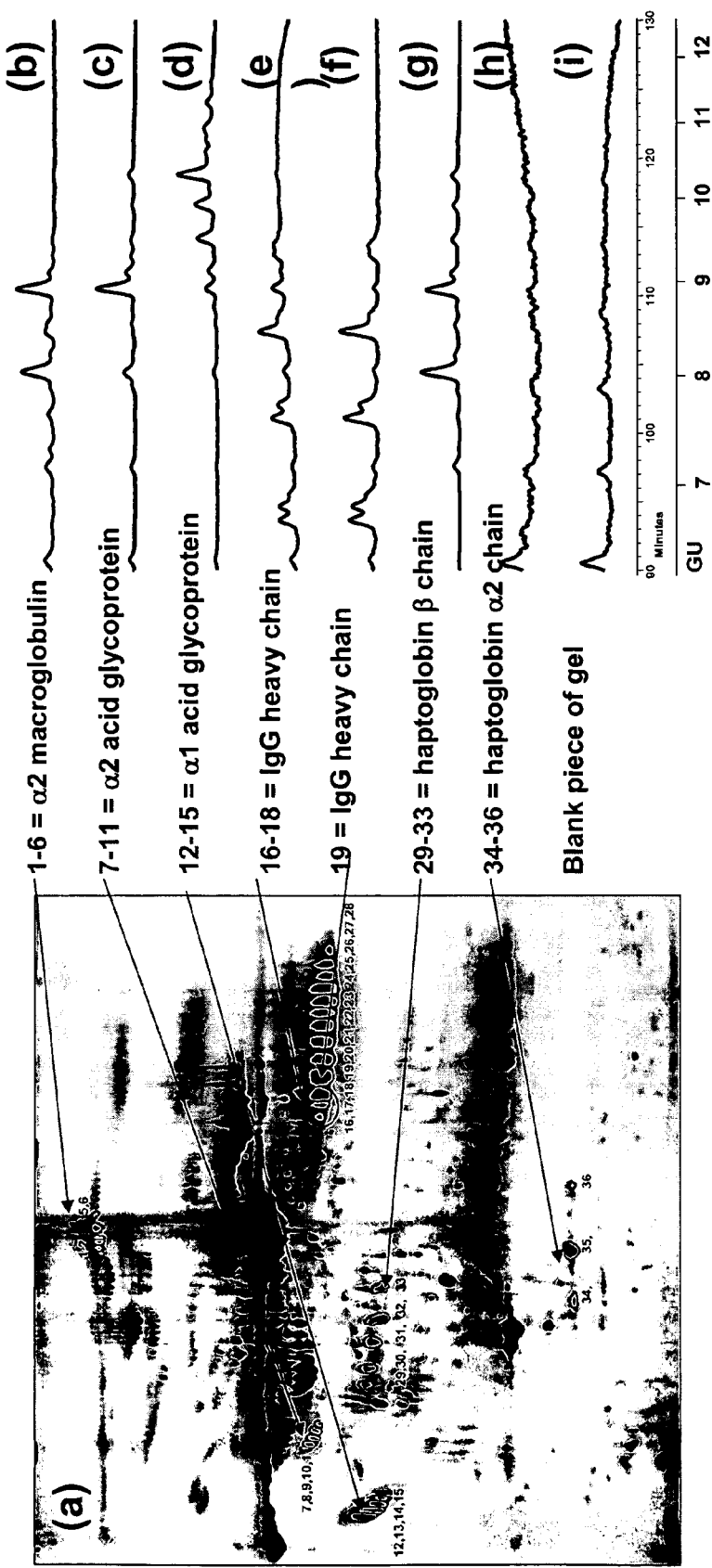
FIG. 12 illustrates measuring glycan profiles from individual or pooled protein spots.

FIG. 12(a) demonstrates 2D-PAGE (2-dimensional polyacrylamide gel electrophoresis) gel from 6.9 µl of control human serum (500 mg of protein), FIG. 12(b-i) shows N-glycan glycoprofiles obtained from individual or pooled protein spots in the 2D-PAGE gel. The marked gel spots were cut out and pooled where they were from the same protein (except for IgG heavy chain when only the first 3 spots were pooled and the fourth spot was analysed as an individual spot). The amount of proteins in the measured gel spots (either individual or pooled) was 20-50 ng. Glycans were released using PNGaseF and 10% of the released glycan pool run on NP-HPLC. The haptoglobin $\alpha 2$ chain, which is not glycosylated, had no detectable glycosylation (h), whereas all of the other proteins showed differing glycosylation.

These data indicate that it is possible to determine the glycosylation of both pooled and individual protein spots separated by 2D-PAGE gel electrophoresis. These data also show that glycosylation can be measured from individual or pooled spots containing less than 2 ng of proteins, since only 10% of the released glycan pool was run on NP-HPLC.

EXAMPLE 4

Breast Cancer

Analysis of Glycosylation Profiles of Glycans Released from whole sera of a breast cancer patient and healthy controls. Glycosylation profiles of glycans released from whole serum of controls and breast cancer patients were compared to detect a potential glycosylation marker differentiating the two groups. In addition to that, total serum glycans from a single breast cancer patient, but at two different stages of malignancy, were analyzed to correlate the detected marker with breast cancer progression.

Samples of serum from breast cancer patient were obtained from a single donor (LD) with her consent before and after mastectomy. The healthy control serum was obtained from pooled blood bank serum.

Glycoproteins in reduced and denatured serum samples were set into gel-blocks, washed and incubated overnight with PNGasF. The released N-glycans were then washed from the bound protein, collected and dried down ready for fluorescent labeling. Released glycans were labeled with 2-aminobenzamide (2-AB) fluorescent label with or without a commercial kit (e.g. Ludger Ltd, Oxford, UK) as described in Bigge, J. C., Patel, T. P., Bruce, J. A., Goulding, P. N., Charles, S. M., and Parekh, R. B. (1995). Nonselective and efficient fluorescent labeling of glycans using 2-amino benzamide and anthranilic acid. Analytical Biochemistry 230: 229-238, incorporated herein by reference in its entirety, and run by normal phase high performance liquid chromatography (NP-HPLC) on a 4.6×250 mm TSK Amide-80 column (Anachem, Luton, UK) using a Waters 2695 separations module equipped with a Waters 2475 fluorescence detector (Waters, Milford, Mass., USA) as described in Guile, G. R., Rudd, P. M., Wing, D. R., Prime, S. B., and Dwek, R. A. (1996). A rapid high-resolution high-performance liquid chromatographic method for separating glycan mixtures and analyzing oligosaccharide profiles. Analytical Biochemistry 240: 210-226, incorporated herein by reference in its entirety. Prior to further NP-HPLC analysis, glycans were digested with a series of exoglycosidases.

FIG. 13A shows glycosylation profiles of undigested glycans released from serum of a healthy control and a breast cancer patient. Sample 1 of the breast cancer patient is taken before surgery and Sample 2 is taken after surgery with liver metastases. Both glycosylation profiles from breast cancer samples demonstrate an increase in the amount of the peak at 10.5 glucose units (GU) compared to the glycosylation profile from the control sample (FIG. 13A). The 10.5 GU peak shifts down to 7.5 GU following digestion with sialidase, β1-3,4,6 galactosidase and α1-2 link specific fucosidase, and has a higher percentage in the patient sample compared to the control (FIG. 13B). The peak at GU 7.5 is then completely digested by the combination of sialidase, β1-4 galactosidase (in place of β1-3,4,6 galactosidase) and α1-3/4 link specific fucosidase in the control and patient samples indicating the presence of outer arm α1-3/4 fucosylation. This demonstrates an increased amount of LewisX epitope in the cancer (FIG. 13C). After surgery the marker decreased from 3.9% to 3.3% suggesting that the prognosis may be poor.

Conclusion: a glycosylation marker of breast cancer was identified by comparing glycosylation profiles of glycans released from whole serum of breast cancer patient and of glycans released from whole serum of a healthy control. Digestion with exoglycosidases amplifies/segregates the glycosylation marker of breast cancer. The glycosylation marker is elevated in disease.

A Longitudinal study of the identified glycosylation marker in one patient. The identified glycosylation marker A3G1F is the outer arm α1-3 linked fucosylated tri-antennary N-linked glycan which is derived from Lewis x or Sialyl Lewis X by treating the N-glycans released from total serum glycoproteins with a combination of sialidase and β-galactosidase which segregates this structure from others. This glycosylation marker is not the native sugar—it is the digestion product—and exoglycosidase digestions enable the amplification and segregation the marker for quantitative HPLC analysis.

Figure 13:
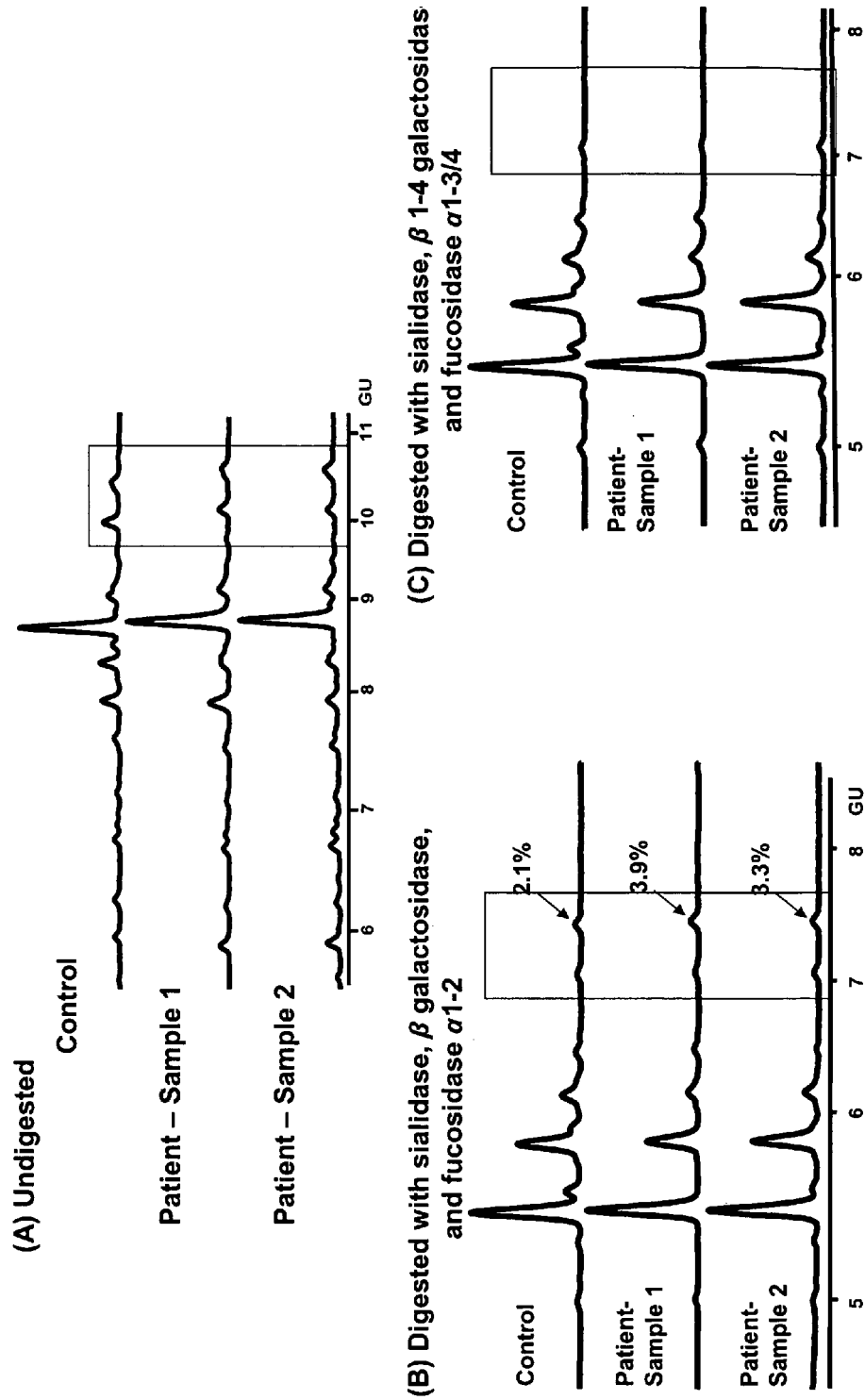
FIG. 13 illustrates determination of a glycosylation marker for breast cancer.
Figure 14:
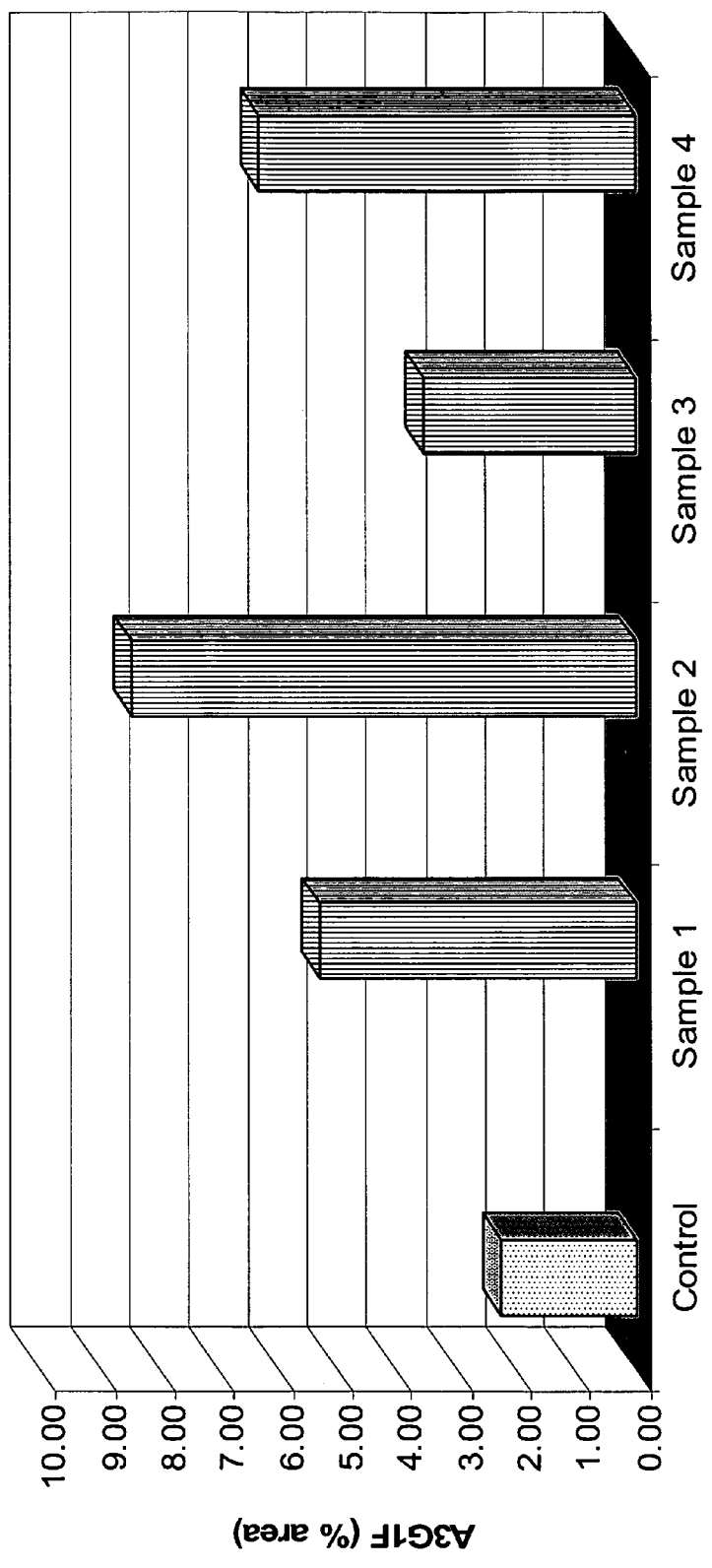
FIG. 14 demonstrates a longitudinal study of A3G3F marker in a single breast cancer patient compared to control.

FIG. 14 presents a longitudinal study of the levels of the glycosylation marker (A3G1F) in the same breast cancer patient as in FIG. 13 at four different stages of breast cancer. The % areas of sLex on the tri-antennary structure in the N-glycan pool released from whole serum was measured after a sialidase, B-galactosidase and α1,2 fucosidase (Abs+Btg+Xmf). All four patient samples have at least a 2-fold increase in the % and the fluctuation shown. Thus, A3G1F glycosylation marker can be used for prognostic applications in breast cancer patients.

Figure 15:
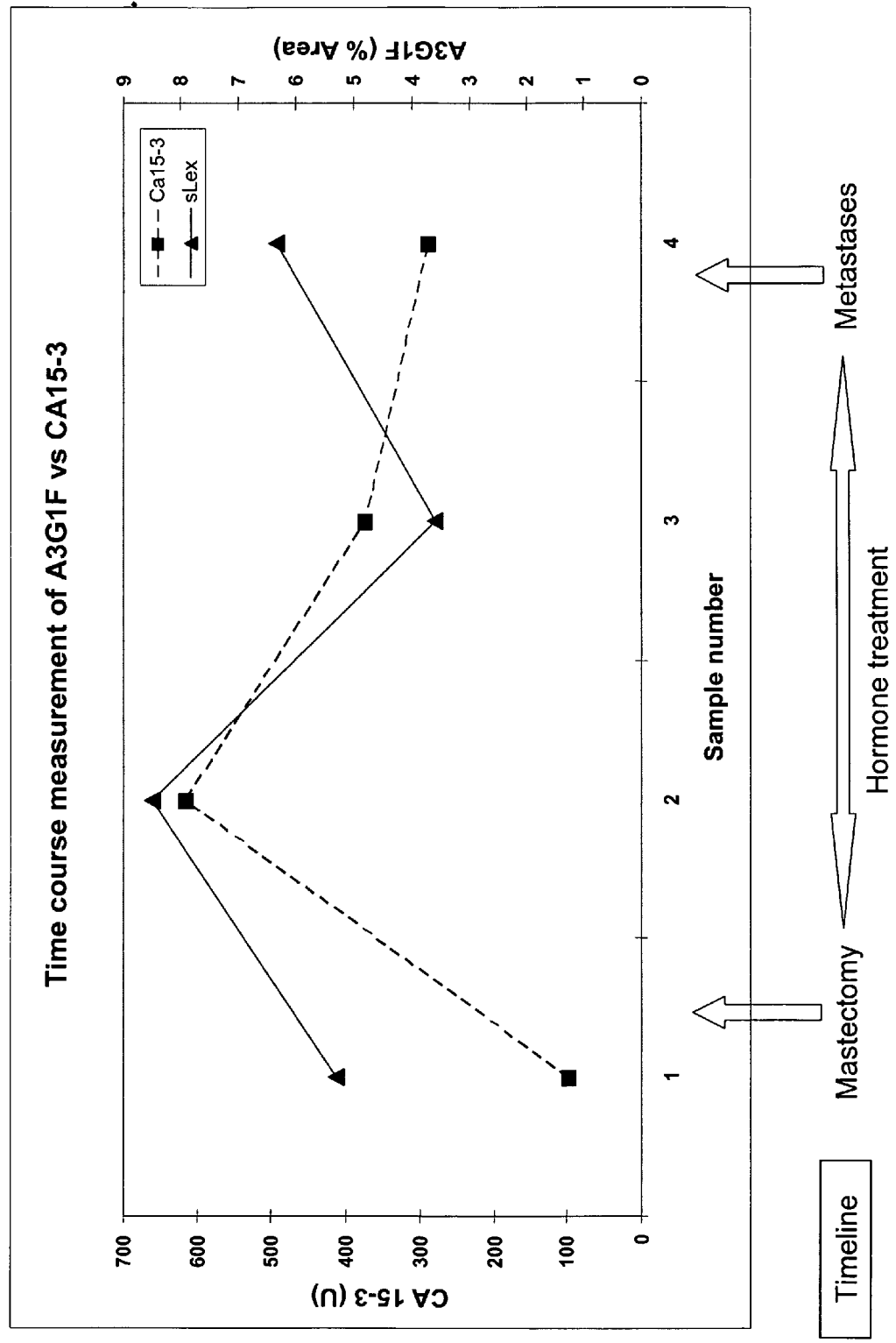
FIG. 15 shows a time course measurement of A3G1F marker vs. CA15-3 marker.

FIG. 15 defines the four stages and compares the levels of glycosylation marker A3G1F with those of carbohydrate antigen 15-3 (CA15-3) protein biomarker. The disease stage at which each sample was collected is shown in a timeline: stage 1: mastectomy, stage 2: mastectomy under hormonal treatment, stage 3: mastectomy under hormonal treatment; stage 4: metastasis detected. At stage 4, when metastasis was detected, the level of A3G1F increases whereas the level of CA15-3 marker was still decreasing. Thus, quantification of the A3G1F glycosylation biomarker may provide an earlier indicator of metastasis.

Identification of Protein Biomarkers. The established A3G1F marker can be used to identify a protein biomarker of breast cancer. The A3G1F is derived mainly from SLex attached to a tri-sialylated tri-antennary N-glycan therefore, one can use an anti-SLex antibody to identify the glycoprotein(s) in Breast Cancer serum which carry such a structure.

Figure 16:
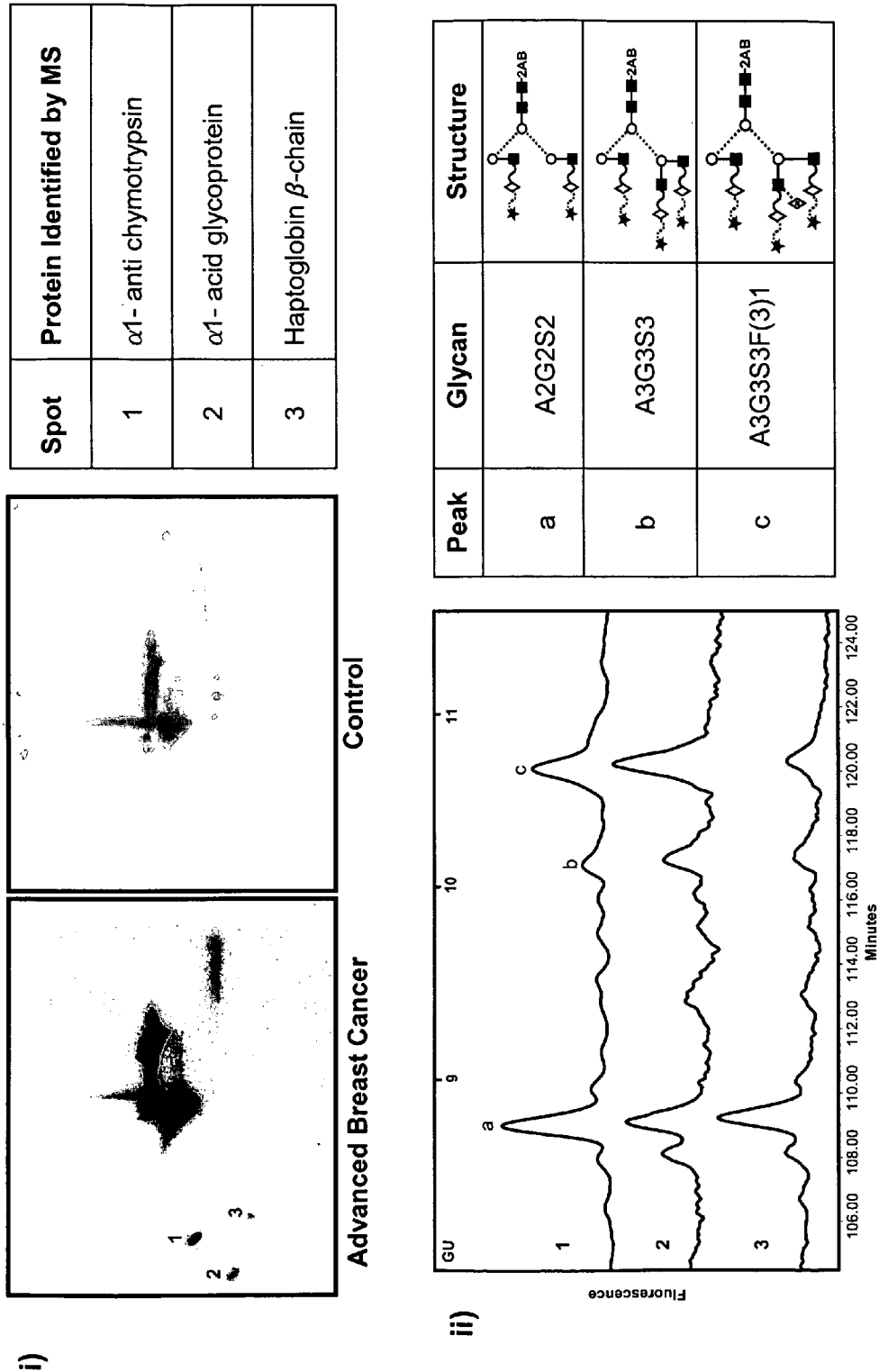
FIG. 16 illustrates identification on 2D-PAGE of glycoproteins carrying the glycan biomarker in breast cancer serum.

Whole serum (80 μg) of control and breast cancer patient were subjected to 2D gel electrophoresis according to the procedure in Example 3 but on mini-gels (1st dimension-7 cm IPG strip pI 3-10, 2nd dimension—8.5×6.5 cm 4-12%) in duplicates. The proteins from one gel of each sample were transferred to a PVDF membrane and blotted using the anti-sialyl Lewis X antibody (KM93, CalBiochem). These western blots with KM93 highlighted the glycoproteins carrying the SLex epitope. FIG. 16(i) shows selected highlighted spots on the blot for control and breast cancer samples. The breast cancer sample presented in FIG. 16(i) is the sample from the same patient at stage 4 as in FIGS. 14&15. Three highlighted protein spots on the gel for breast cancer sample in FIG. 16i have been identified by mass spectrometry as 1-α1 anti chymotrypsin, 2-α1 acid glycoprotein, 3-haptoglobin B chain and/or Complement C3.

N-glycans were released from each of the three spots by PNGaseF digestion and subjected to detailed glycosylation analysis by HPLC. The glycosylation profiles from each of the three glycoproteins were found to have the sialyl Lewis x structure, see FIG. 16(ii).

Thus, measuring glycoprofile from 2D-gel spot(s) can enable the identification of aberrantly glycosylated protein glycoforms in breast cancer serum as biomarkers for prognosis and diagnosis of patients.

EXAMPLE 5

Ovarian Cancer

Analysis of Glycans Released from Whole sera of Ovarian cancer patients and corresponding healthy controls. Glycosylation profiles of glycans released from whole serum of healthy control and ovarian cancer patient were compared to detect a potential glycosylation marker differentiating the two groups.

Samples of tumor serum were obtained from a patient with advanced malignant tumor. The healthy control serum was obtained from pooled blood bank serum. The procedure identical to the one in Example 4 was used for preparation of glycans for glycosylation analysis.

Figure 17:
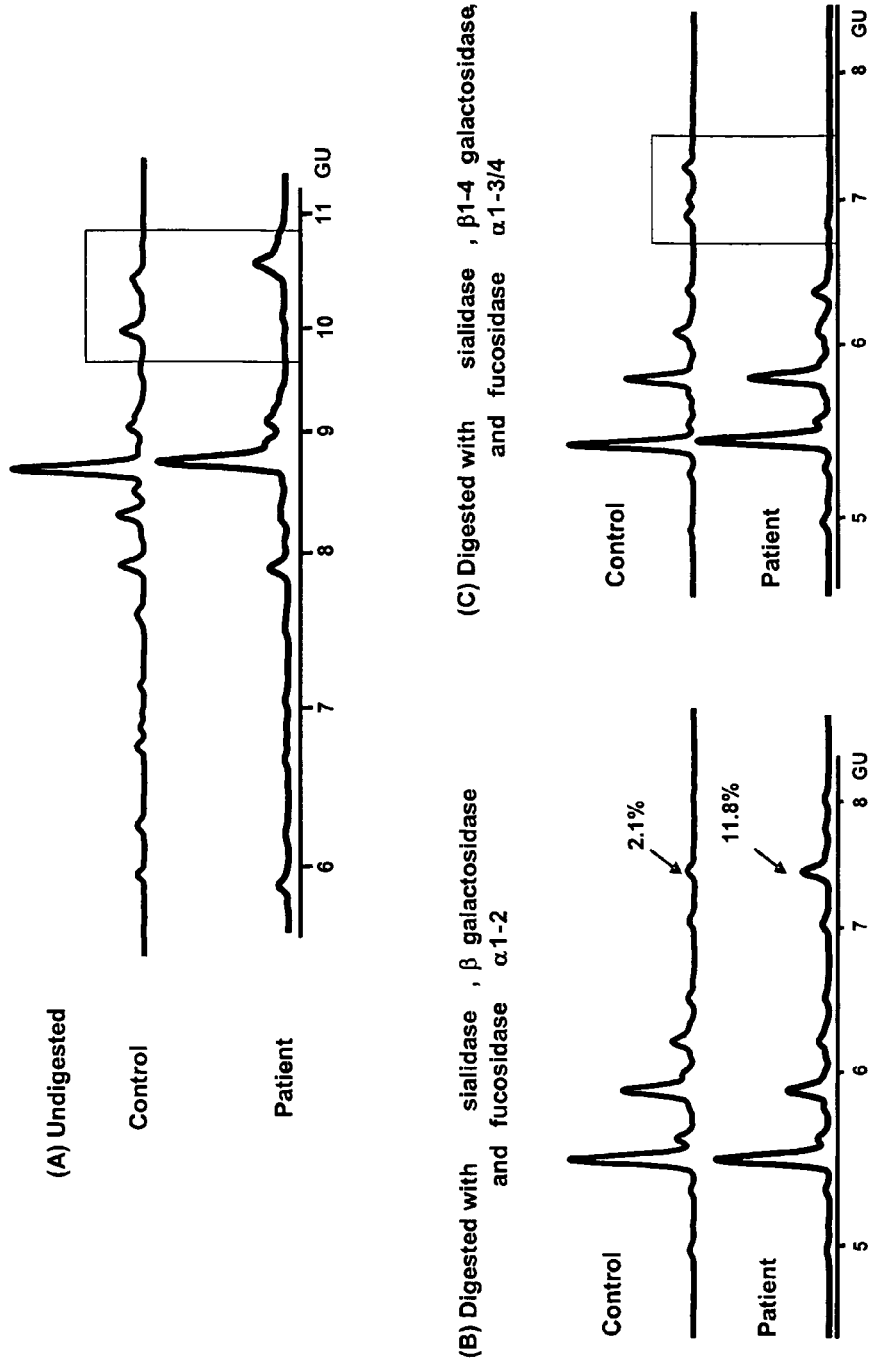
FIG. 17 illustrates determination of a glycosylation marker for ovarian cancer.

Resulting glycosylation profiles are presented on FIG. 17. In particular, FIG. 17A demonstrates the glycosylation profiles of undigested glycans, FIG. 17B demonstrates the glycosylation profiles of glycans digested with sialidase, β1-3,4,6 galactosidase and a 1-2 link specific fucosidase, while FIG. 17C demonstrates the glycosylation profiles of glycans further digested with sialidase, β1-4 galactosidase (in place of β1-3,4,6 galactosidase) and α1-3/4 link specific fucosidase. For undigested glycans, a difference between glycosylation profiles from ovarian cancer sample and from healthy control sample was observed in the region of ~9.5 to ~11 GU (FIG. 17A). In particular, a peak was observed ~10.5 GU in the ovarian cancer patient which was smaller in the control sample. Upon digestion with sialidase, β1-3,4,6 galactosidase and α1-2 link specific fucosidase, the ~10.5 GU peak shifted to ~7.5 GU (FIG. 17B). The 7.5 GU peak has a higher percentage (~11.8%) in the ovarian cancer sample than in the control sample. The peak at GU 7.5 is then completely digested by the combination of sialidase, β1-4 galactosidase (in place of β1-3,4,6 galactosidase) and α1'-3/4 link specific fucosidase in the patient samples indicating the presence of outer arm α1-3 fucose (i.e. Lewis x epitope) (FIG. 17C).

Conclusion: a glycosylation marker of ovarian cancer was identified by comparing glycosylation profiles of glycans released from whole serum of ovarian cancer patient and of glycans released from whole serum of a healthy control. Digestion with exoglycosidases amplifies/segregates the glycosylation marker of ovarian cancer.

Glycosylation Analysis from Whole Serum 2D Gel Spots

Figure 18:
FIG. 18 shows 2-dimensional electrophoresis of serum highlighting the train of spots containing haptoglobin β-chain.
Figure 19:
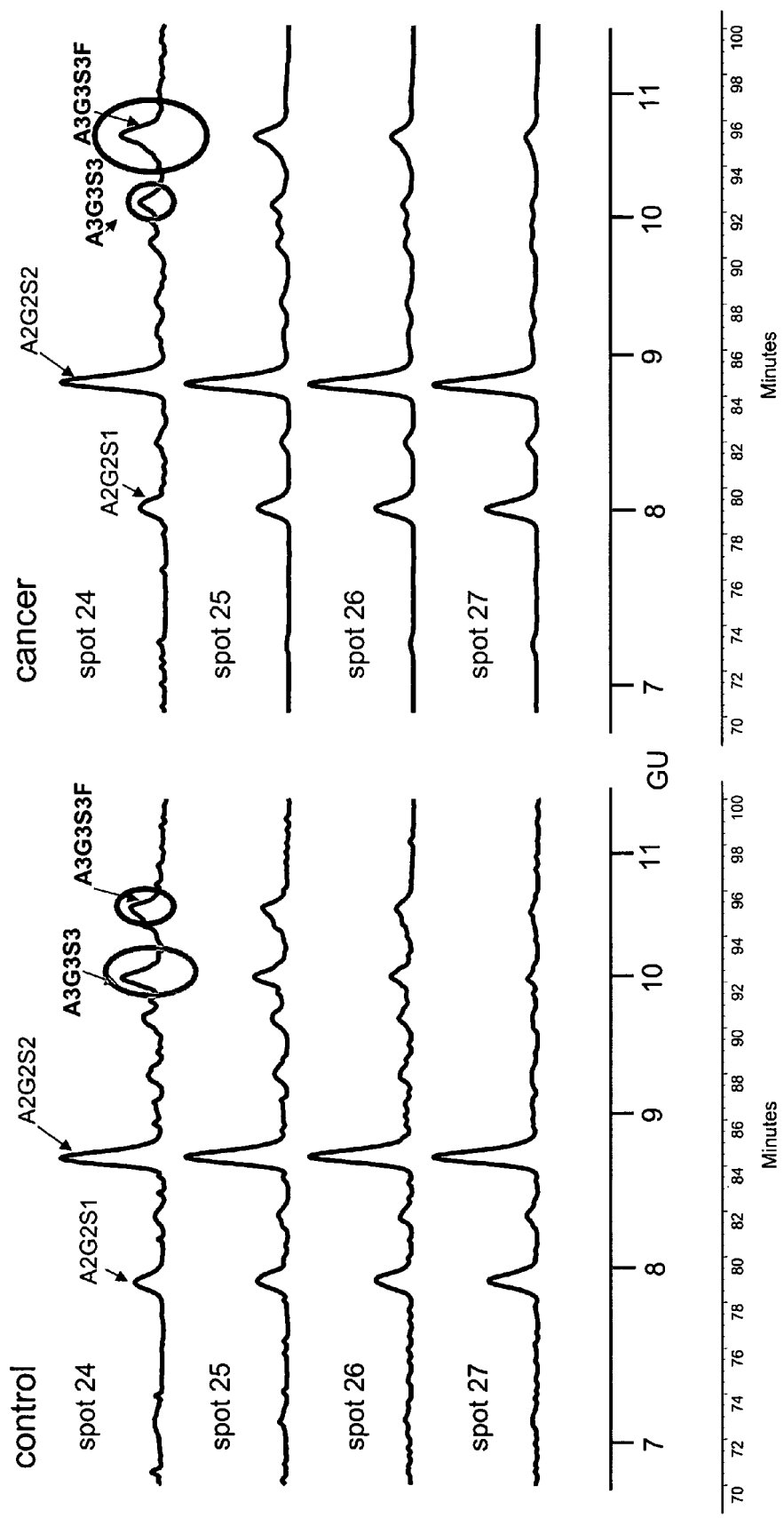
FIG. 19 illustrates glycosylation analysis of the train of spots from haptoglobin β-chain (FIG. 18) showing that different sub-populations of glycoprotein (glycoforms) are present in each spot of the train. The analysis was carried out directly from the gel spots.

Whole serum (80 µg) of control and ovarian cancer patient were subjected to 2D gel electrophoresis according to the procedure in Example 4. FIG. 18 shows 2D gel electrophoresis of serum highlighting the train of haptoglobin β-chain spots which were excised for glycosylation analysis. Since less than 2 µg of haptoglobin in total were loaded in the gels, each spot in the train contains less than 400 ng of protein. FIG. 19 shows NP-HPLC glycosylation profiles obtained from spots 24-27 of haptoglobin β chain train for control and ovarian cancer samples. The ratio of A3G3S3F to A3G3S3 is higher in the ovarian cancer haptoglobin β-chain spots, particularly for spot 24, compared to respective control spots.

Conclusion: glycosylation profiles can be determined from each individual spot from a train of spots on 2D-gel. Glycosylation marker(s) of ovarian cancer can be identified and quantified by measuring glycosylation profiles of glycans released from individual spots of 2D gel.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

ADDITIONAL EMBODIMENTS

1. A method of determining one or more glycosylation markers of disease comprising
    obtaining a diseased sample and a control sample, wherein the diseased sample is a sample from a subject diagnosed with disease and the control sample is a sample from a healthy control;
    releasing a diseased glycan pool of total glycoproteins from the diseased sample and a control glycan pool of total glycoproteins from the control sample without purifying the glycoproteins and without exposing the diseased sample and the control sample to hydrazinolysis wherein the total glycoproteins from the disease and the total glycoproteins from the control sample are immobilized in a high throughput format;
    measuring a diseased glycoprofile of the diseased glycan pool and a control glycoprofile of the control glycan pool using chromatography, mass spectrometry or a combination thereof;
    comparing the diseased glycoprofile and the control glycoprofiles to determine said one or more glycosylation markers of disease.

2. The method of embodiment 1, wherein comparing the diseased glycoprofile and the control glycoprofile comprises comparing peak ratios in the diseased glycoprofile and in the control glycoprofile.

3. The method of embodiment 1, further comprising selecting a best glycosylation marker out of said one or more glycosylation markers of disease, wherein the best glycosylation marker has a highest correlation with one or more parameters of the subject diagnosed with disease.

4. The method of embodiment 3, wherein the parameters of the subject diagnosed with disease are diagnosis, disease stage, disease severity, age, sex, medical history, response to therapy or a combination thereof.

5. The method of embodiment 3, wherein the parameter is diagnosis.

6. The method of embodiment 1, wherein the disease is cancer, autoimmune disease or congenital disorder of glycosylation.

7. The method of embodiment 6, wherein the cancer is pancreatic cancer, prostate cancer, breast cancer, hepatocellular carcinoma, ovary cancer, bladder cancer, renal cancer, colon cancer, stomach cancer or lung cancer.

8. The method of embodiment 6, wherein the autoimmune disease is rheumatoid arthritis, osteoarthritis, juvenile chronic arthritis, systematic lupus erythematosus, Sjögren's syndrome, ankylosing spondylitis, psoriatic arthritis, multiple sclerosis, inflammatory bowel disease, graft-vs-host disease or scleroderma.

9. The method of embodiment 1, further comprising digesting the diseased glycan pool and the control glycan pool with none, one or more exoglycosidases.

10. The method of embodiment 9, wherein said digesting is sequential digesting.

11. The method of embodiment 9, wherein said digesting the diseased glycan pool and the control glycan pool is digesting with an array comprising with one or more glycosidases.

12. The method of embodiment 1, wherein the diseased glycan pool and the control glycan pool are pools of N-linked glycans.

13. The method of embodiment 1, wherein the diseased glycan pool and the control glycan pool are pools of O-linked glycans.

14. The method of embodiment 1, wherein the total glycoproteins from the diseased sample and the total glycoproteins from the control sample are immobilized in a gel.

15. The method of embodiment 14, wherein said releasing comprises releasing from the gel without separating the gel into bands.

16. The method of embodiment 1, wherein the total glycoproteins from the diseased sample and the total glycoproteins from the control sample are immobilized on polyvinyldene fluoride membranes.

17. The method of embodiment 16, wherein said releasing is releasing by ammonia-based β-elimination from the polyvinyldene fluoride membranes.

18. The method of embodiment 1, further comprising labeling glycans in the diseased glycan pool and the control glycan pool with a radioactive or a fluorescent label.

19. The method of embodiment 18, wherein the fluorescent label is 2-aminopyridine, 2-aminobenzamide, 2-aminoanthranilic acid, 2-aminoacridone or 8-aminonaphthalene-1,3, 6-trisulfonic acid.

20. The method of embodiment 19, wherein the fluorescent label is 2-aminobenzamide.

21. The method of embodiment 1, wherein the diseased sample and the control sample are samples of a body fluid.

22. The method of embodiment 21, wherein the body fluid is whole serum, blood plasma, urine, seminal fluid or saliva.

23. The method of embodiment 21, wherein the body fluid is whole serum.

24. The method of embodiment 1, wherein measuring the diseased glycoprofile and the control glycoprofile comprises building a diseased database and a control database, wherein the diseased database comprises glycan structures present in the diseased glycan pools and the control database comprises glycan structures present in the control glycan pool.

25. A method for diagnosing and monitoring disease in a subject comprising
obtaining a sample of body fluid or a body tissue of the subject;
releasing a glycan pool of total glycoproteins from the sample without purifying the glycoproteins and exposing the sample to hydrazinolysis;
measuring a glycoprofile of the glycan pool.

26. The method of embodiment 25, further comprising determining a clinical status of the subject from a level of a glycosylation marker of disease in the glycoprofile.

27. The method of embodiment 25, wherein the disease is cancer, autoimmune disease or congenital disorder of glycosylation.

28. The method of embodiment 27, wherein the cancer is pancreatic cancer, prostate cancer, breast cancer, hepatocellular carcinoma, ovarian cancer, bladder cancer, renal cancer, colon cancer, stomach cancer or lung cancer.

29. The method of embodiment 27, wherein the autoimmune disease is rheumatoid arthritis, osteoarthritis, juvenile chronic arthritis, systematic lupus erythematosus, Sjögren's syndrome, ankylosing spondylitis, psoriatic arthritis, multiple sclerosis, inflammatory bowel disease, graft-vs-host disease or scleroderma.

30. The method of embodiment 25, wherein the body fluid is whole serum, blood plasma, urine, seminal fluid or saliva.

31. The method of embodiment 25, wherein the body fluid is whole serum.

32. The method of embodiment 25, wherein releasing a glycan pool comprises preparing a gel from the sample.

33. The method of embodiment 32, wherein the glycan pool is a pool of N-linked glycans and releasing a glycan pool further comprises releasing the pool of N-glycans from the gel using PNGase F enzyme.

34. The method of embodiment 25, wherein releasing the glycan pool comprises attaching the total glycoproteins to polyvinyldene fluoride membranes.

35. The method of embodiment 34, wherein the glycan pool is a pool of N-glycans and releasing the glycan pool further comprises incubating the polyvinyldene fluoride membranes with PNGaseF enzyme.

36. The method of embodiment 34, wherein releasing the glycan pool further comprises chemically releasing the glycan pool by β-elimination.

37. The method of embodiment 34, wherein releasing the glycan pool further comprises releasing the glycan pool by ammonia-based β-elimination.

38. The method of embodiment 25, further comprising digesting the glycans with one or more exoglycosidase.

39. The method of embodiment 25, further comprising sequential digesting the glycans with one or more exoglycosidase.

40. The method of embodiment 25, further comprising digesting the glycans with an array comprising more than one exoglycosidase.

41. The method of embodiment 25, further comprising digesting the glycans with an array comprising more than one exoglycosidase.

42. The method of embodiment 25, wherein measuring the glycoprofile is carried out by chromatography, mass spectrometry or a combination thereof.

43. A method for optimizing a dosage of a existing therapeutic agent against disease comprising
obtaining a first sample of a body fluid or a body tissue from a diseased subject before administering the therapeutic agent to the patient;
obtaining a second sample of a body fluid or a body tissue from the diseased subject after administering the therapeutic agent to the patient;
releasing glycans of glycoproteins from the first and the second samples without purifying the glycoproteins and without exposing the first and the second sample to hydrazinolysis;
measuring a first glycoprofile of the glycans from the first sample and a second glycoprofile of the glycans from the second sample;
comparing a level of a glycosylation marker of the disease in the first glycoprofile and the second glycoprofile.

44. A method of testing a new therapy or a new therapeutic agent for treating disease comprising
obtaining a first sample of a body fluid or a body tissue from a diseased subject before exposing the patient to the new therapy or the new therapeutic agent;
obtaining a second sample of a body fluid or a body tissue from the diseased subject after exposing the patient to the new therapy or the new therapeutic agent;
releasing glycans of glycoproteins from the first and the second samples without purifying the glycoproteins and without exposing the first and the second samples to hydrazinolysis;
measuring a first glycoprofile of the glycans from the first sample and a second glycoprofile of the glycans from the second sample;
comparing a level of a glycosylation marker of the disease in the first glycoprofile and the second glycoprofile.

45. A database of disease comprising
glycan structures in a diseased glycan pool of total glycoproteins in a diseased sample from a subject diagnosed with disease, wherein the diseased glycan pool is released from the diseased sample without purifying the glycoproteins and without exposing the sample to hydrazinolysis.

46. The database of claim 45, wherein the glycans are N-glycans.

47. The database of claim 45, wherein the glycans are O-glycans.

48. The database of claim 45, further comprising glycan structures in a control glycan pool of total glycoproteins in a control sample from a healthy control, wherein the control glycan pool is released from the diseased sample without purifying the glycoproteins and without exposing the sample to hydrazinolysis.

49. The database of claim 45, wherein the disease is cancer, autoimmune disease or congenital disorder of glycosylation.

50. The database of claim 49, wherein the cancer is pancreatic cancer, prostate cancer, breast cancer, hepatocellular carcinoma, ovary cancer, bladder cancer, renal cancer, colon cancer, stomach cancer or lung cancer.

51. The database of claim 49, wherein the autoimmune disease is rheumatoid arthritis, osteoarthritis, juvenile chronic arthritis, systematic lupus erythematosus, Sjögren's syndrome, ankylosing spondylitis, psoriatic arthritis, multiple sclerosis, inflammatory bowel disease, graft-vs-host disease or scleroderma.

52. A method of glycan releasing from a sample of a subject comprising
immobilizing one or more glycoproteins of the sample in a gel;
releasing the glycans of the one or more glycoproteins from the gel without separating the gel into bands.

53. The method of embodiment 53, wherein the one or more glycoproteins are total glycoproteins of the sample.

54. The method of embodiment 52, wherein the one or more glycoproteins are purified glycoproteins.

55. The method of embodiment 52, wherein the gel is polyacrylamide gel.

56. The method of embodiment 52, wherein releasing a glycan pool is carried out using one or more enzymes.

57. The method of embodiment 56, wherein the glycans are N-glycans and wherein the enzyme is PNGaseF.

58. A method of glycan releasing from a sample of a subject comprising
immobilizing one or more glycoproteins of the sample on a protein binding membrane;
releasing glycans of the one or more glycoproteins using a β-elimination.

59. The method of embodiment 58, wherein the one or more glycoproteins are total glycoproteins of the sample.

60. The method of embodiment 58, wherein the one or more glycoproteins are one or more purified glycoproteins.

61. The method of embodiment 58, wherein the membrane is a polyvinyldene fluoride membrane.

62. The method of embodiment 58, wherein the β-elimination is an ammonia-based β-elimination.

63. A method of identifying one or glycoprotein biomarkers of a disease comprising
determining a glycosylation marker of the disease by a detailed quantitative analysis of a glycan pool of total glycoproteins in a body fluid or a body tissue, wherein the glycan pool is released without purifying the glycoproteins and without exposing the body fluid or the body tissue to hydrazinolysis;
extracting the one or more glycoprotein biomarkers of the disease from the total glycoproteins, wherein the one or more glycoprotein biomarkers display the glycosylation marker of the disease.

64. The method of embodiment 63, wherein said extracting is carried out using lectins or monoclonal antibodies.

65. A method of identifying one or more biomarkers of disease, said method comprising
separating a protein pool from a body fluid or a body tissue of a subject of the disease using 2 dimensional electrophoresis into individual spots or trains of spots, each of the individual spots and each of the spots in the trains comprises one or more proteins from the protein pool;
measuring detailed glycoprofiles of glycan pools released from the individual spots or single or pooled spots in an individual train of the trains and identifying out of the measured spots one or more disease associated spots as said one or more biomarkers of disease, said disease associated spots have corresponding glycosylation profiles altered.

66. The method of embodiment 65, wherein, said identifying comprises comparing the glycosylation profiles corresponding to the spots associated with one or more particular glycoproteins in the protein pool.

67. The method of embodiment 65, wherein said measuring comprises using chromatography.

68. The method of embodiment 65, wherein said measuring comprises labeling glycans of the glycan pools with a fluorescent label, said fluorescent label is 2-aminopyridine, 2-aminobenzamide, 2-aminoanthranilic acid, 2-aminoacridone or 8-aminonaphthalene-1,3,6-trisulfonic acid.

69. The method of embodiment 65, wherein the body fluid is whole serum, blood plasma, urine, seminal fluid or saliva.

70. The method of embodiment 65, wherein said glycan pools are N-glycan pools.

71. The method of embodiment 69, wherein said N-glycan pools are released using PNGase F enzyme.

72. The method of embodiment 65, wherein said measuring is carried by a technique capable of measuring a glycosylation profile corresponding to a spot containing less than about 100 nanogramms of protein.

73. The method of embodiment 65, wherein said measuring is carried by a technique capable of measuring a glycosylation profile corresponding to a spot containing less than about 10 nanogramms of protein.

74. The method of embodiment 65, wherein said measuring is carried by a technique capable of measuring a glycosylation profile corresponding to a spot containing less than about 5 nanogramms of protein.

75. The method of embodiment 65, wherein said measuring is carried by a technique capable of measuring a glycosylation profile corresponding to a spot containing less than about 2 nanogramms of protein.

76. The method of embodiment 65, wherein the disease is cancer, autoimmune disease or congenital disorder of glycosylation.

77. The method of embodiment 76, wherein the cancer is pancreatic cancer, prostate cancer, breast cancer, hepatocellular carcinoma, ovary cancer, bladder cancer, renal cancer, colon cancer, stomach cancer or lung cancer.

78. The method of embodiment 76, wherein the autoimmune disease is rheumatoid arthritis, osteoarthritis, juvenile chronic arthritis, systematic lupus erythematosus, Sjögren's syndrome, ankylosing spondylitis, psoriatic arthritis, multiple sclerosis, inflammatory bowel disease, graft-vs-host disease or scleroderma.

79. The method of embodiment 65, wherein the subject is a human being.

What is claimed is:

1. A method of identifying and/or quantifying one or more differences in glycosylation between a biological sample affected by a physiological condition and a control sample, comprising
(A) obtaining the biological sample, wherein the biological sample contains a plurality of different types of glycoproteins;
(B) immobilizing total glycoproteins from the biological sample on a protein binding membrane or in a gel; then
(C) releasing glycans of the total glycoproteins immobilized on the protein binding membrane or in the gel without exposing the glycoproteins to hydrazinolysis and without the glycoproteins having been separated into bands prior to said releasing; then (D) washing the protein binding membrane or the gel to separate the released glycans from parent proteins immobilized on the protein binding membrane or in the gel;

(E) measuring a glycosylation profile of the glycans; and (F) comparing the glycosylation profile with a glycosylation profile of the control sample to determine the one or more differences in glycosylation between the biological sample affected by the physiological condition and the control sample.

2. The method of claim 1, wherein the biological sample is a biological sample from a mammal.

3. The method of claim 2, wherein the mammal is a human.

4. The method of claim 2, wherein the biological sample is a sample of a body fluid or a body tissue.

5. The method of claim 4, wherein the body fluid is whole serum.

6. The method of claim 2, wherein the physiological condition is a disease or a stage of disease.

7. The method of claim 1, wherein said immobilizing comprises immobilizing the total glycoproteins in the gel and releasing glycans from the total glycoproteins immobilized on the gel without separating the glycoproteins into bands.

8. The method of claim 1, wherein said immobilizing is in a high-throughput format.

9. The method of claim 1, wherein the glycans are N-linked glycans.

10. The method of claim 1, wherein the glycans are O-linked glycans.

11. The method of claim 1, further comprising labeling glycans with a fluorescent label.

12. The method of claim 11, wherein the fluorescent label is 2-aminobenzamide.

13. The method of claim 1, further comprising selecting the difference having a highest correlation with one or more parameters of the biological sample.

14. The method of claim 1, further comprising segregating and/or amplifying the one or more differences by digesting the released glycans with one or more exoglycosidases prior to measuring the glycosylation profile.

15. The method of claim 14, wherein said digesting is performed sequentially.

16. The method of claim 14, wherein said digesting is digesting with an array comprising one or more exoglycosidases.

17. The method of claim 14, further comprising interpreting the difference using a database.

18. The method of claim 14, wherein the difference comprises one or more digested glycans.

19. The method of claim 1, further comprising monitoring the physiological condition by measuring a level of the difference in a sample of a new subject.

20. The method of claim 1, wherein said immobilizing is immobilizing on the protein binding membrane.

21. The method of claim 1, further comprising using the one or more differences to diagnose, prognosticate and/or monitor the physiological condition.

22. The method of claim 1, wherein the measuring is measuring by quantitative high performance liquid chromatography, mass spectrometry or a combination thereof.

23. A method of releasing glycans comprising
immobilizing one or more glycoproteins of a glycoprotein-containing sample in a gel;
releasing glycans of the one or more immobilized glycoproteins from the gel without exposing the one or more immobilized glycoproteins to hydrazinolysis and without the one or more immobilized glycoproteins having been separated into bands on the gel prior to said releasing; and
washing the gel to separate the released glycans from parent proteins immobilized on the gel.

24. The method of claim 23, further comprising digesting the released glycans with one or more exoglycosidase(s) and then measuring a glycosylation profile of the digested glycans, wherein said digesting segregates and/or amplifies one or more glycosylation markers in the released glycans.

25. A method of releasing glycans comprising
immobilizing one or more glycoproteins of a glycoprotein-containing sample on a protein binding membrane, without having separated the one or more immobilized glycoproteins into bands on a gel;
releasing glycans of the one or more immobilized glycoproteins on the protein binding membrane without exposing the one or more immobilized glycoproteins to hydrazinolysis; and
washing the protein binding membrane to separate the released glycans from parent proteins immobilized on the protein binding membrane.

26. The method of claim 25, further comprising digesting the released glycans with one or more exoglycosidase(s) and then measuring a glycosylation profile of the digested glycans, wherein said digesting segregates and/or amplifies one or more glycosylation markers in the released glycans.

27. A method for diagnosing and monitoring a disease comprising (A) obtaining a glycoprotein-containing sample of a body fluid or a body tissue of a subject in need thereof;

(B) immobilizing total glycoproteins from the sample on a protein binding membrane or in a gel, without having separated the one or more immobilized glycoproteins into bands on a gel;

(C) releasing a glycan pool of the total glycoproteins immobilized on the protein binding membrane or in the gel without exposing the glycoproteins to hydrazinolysis and without separating the glycoproteins into bands prior to said releasing;

(D) washing the protein binding membrane or the gel to separate the released glycans from parent proteins immobilized on the protein binding membrane or in the gel;

(E) measuring a glycosylation profile of the glycan pool for one or more previously identified and quantified glycosylation marker(s) of the disease; and (F) determining a clinical status of the subject from the one or more glycosylation marker(s) of the disease in the glycosylation profile.

28. The method of claim 27, further comprising segregating and/or amplifying the one or more glycosylation marker(s) by digesting the released glycans with one or more exoglycosidase(s) prior to the measuring the glycosylation profile.

* * * * *